United States Patent
Hosse et al.

(10) Patent No.: US 10,745,470 B2
(45) Date of Patent: Aug. 18, 2020

(54) MODIFIED ANTI-TENASCIN ANTIBODIES AND METHODS OF USE

(71) Applicant: Hoffmann-La Roche Inc., Little Falls, NJ (US)

(72) Inventors: Ralf Hosse, Schlieren (CH); Ekkehard Moessner, Schlieren (CH); Pablo Umana, Schlieren (CH)

(73) Assignee: Hoffmann-La Roche Inc., Little Falls, NJ (US)

(*) Notice: Subject to any disclaimer, the term of this patent is extended or adjusted under 35 U.S.C. 154(b) by 85 days.

(21) Appl. No.: 16/186,418

(22) Filed: Nov. 9, 2018

(65) Prior Publication Data

US 2019/0169277 A1 Jun. 6, 2019

Related U.S. Application Data

(63) Continuation of application No. PCT/EP2017/060869, filed on May 8, 2017.

(30) Foreign Application Priority Data

May 11, 2016 (EP) .................................. 16169239

(51) Int. Cl.
*A61P 35/00* (2006.01)
*C07K 16/18* (2006.01)
*C12N 15/85* (2006.01)
*A61K 38/00* (2006.01)

(52) U.S. Cl.
CPC ............. *C07K 16/18* (2013.01); *A61P 35/00* (2018.01); *C12N 15/85* (2013.01); *A61K 38/00* (2013.01); *C07K 2317/21* (2013.01); *C07K 2317/31* (2013.01); *C07K 2317/33* (2013.01); *C07K 2317/55* (2013.01); *C07K 2317/565* (2013.01); *C07K 2317/73* (2013.01); *C07K 2317/92* (2013.01); *C12N 2015/8518* (2013.01)

(58) Field of Classification Search
None
See application file for complete search history.

(56) References Cited

U.S. PATENT DOCUMENTS 7,968,685 B2* 6/2011 Brack .................... C07K 16/28
530/387.1

FOREIGN PATENT DOCUMENTS

| EP | 1173766 B1 | 9/2004 |
|---|---|---|
| EP | 1817345 B1 | 5/2009 |
| WO | 2006/050834 A2 | 5/2006 |
| WO | 2006/050834 A3 | 5/2006 |
| WO | 2009/089998 A1 | 7/2009 |
| WO | 2012/020038 A1 | 2/2012 |

OTHER PUBLICATIONS

Balza, E., et al., "Production and characterization of monoclonal antibodies specific for different epitopes of human tenascin" FEBS Lett 332(1-2):39-43 (Oct. 1, 1993).
Borsi, L., et al., "Expression of different tenascin isoforms in normal, hyperplastic and neoplastic human breast tissues" Int J Cancer 52(5):688-692 (Nov. 11, 1992).
Brack et al., "Tumor-Targeting Properties of Novel Antibodies Specific to the Large Isoform of Tenascin-C" Clin Cancer Res 12(10):3200-3208 (May 15, 2006).
Carnemolla et al., "Comparison of human tenascin expression in normal, Simian-Virus-40-transformed and tumor-derived cell lines" Eur J Biochem 205(2):561-567 (Apr. 15, 1992).
Chiquet-Ehrismann, R., et al., "Tenascins: regulation and putative functions during pathological stress" J Pathol 200(4):488-499 (Jul. 1, 2003).
Hanamura et al., "Expression of fibronectin and tenascin-C mRNA by myofibroblasts, vascular cells and epithelial cells in human colon adenomas and carcinomas" Int J Cancer 73(1):10-15 (Aug. 31, 1997).
Hsia, H., et al., "Meet the Tenascins: Multifunctional and Mysterious" J Biol Chem 280(29):26641-26644 (Jul. 22, 2005).
"International Preliminary Report on Patentability—PCT/EP2017/060869": pp. 1-10 (dated Nov. 13, 2018).
"International Search Report—PCT/EP2017/060869 dated Aug. 8, 2017": pp. 1-7 (Aug. 8, 2017).
Joester, A., et al., "Evidence for Combinatorial Variability of Tenascin-C Isoforms and Developmental Regulation in the Mouse Central Nervous System" J Biol Chem 274(24): 17144-17151 (Jun. 11, 1999).
Orend, G., et al., "Tenascin-C induced signaling in cancer" Cancer Lett 244(2): 143-163 (Dec. 8, 2006).
Silacci, M., et al., "Human monoclonal antibodies to domain C of tenascin-C selectively target solid tumors in vivo" Protein Eng Des Sel 19(10):471-478 (Oct. 19, 2006).
Wang, Yu-Cai, et al., "Generation and Identification of Monoclonal Antibodies Against FNIII Domain D of Human Tenascin-C" Hybridoma 29(1):13-16 (Jan. 31, 2010).
Yoshida et al., "Co-expression of tenascin and fibronectin in epithelial and stromal cells of benign lesions and ductal carcinomas in the human breast" J Pathol 182(4):421-428 (Mar. 6, 1997).

* cited by examiner

Primary Examiner — Meera Natarajan

(57) ABSTRACT

The present invention relates to improved antibodies specific for Tenascin-C (TnC), in particular domain specific anti-TnC antibodies with improved cross-species reactivity. In addition, the invention relates to polynucleotides encoding such antibodies, and vectors and host cells comprising such polynucleotides. The invention further relates to methods for producing the antibodies and methods of using them in the treatment of disease.

24 Claims, 4 Drawing Sheets

Specification includes a Sequence Listing.

SEQUENCE LISTING

<160> NUMBER OF SEQ ID NOS: 93

<210> SEQ ID NO 1
<211> LENGTH: 3102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: huTNC

<400> SEQUENCE: 1

| | | | | | |
|---|---|---|---|---|---|
| atgtcccta | tactaggtta | ttggaaaatt | aagggccttg | tgcaacccac | tcgacttctt | 60 |
| ttggaatatc | ttgaagaaaa | atatgaagag | catttgtatg | agcgcgatga | aggtgataaa | 120 |
| tggcgaaaca | aaaagtttga | attgggtttg | gagtttccca | atcttcctta | ttatattgat | 180 |
| ggtgatgtta | aattaacaca | gtctatggcc | atcatacgtt | atatagctga | caagcacaac | 240 |
| atgttgggtg | gttgtccaaa | agagcgtgca | gagatttcaa | tgcttgaagg | agcggttttg | 300 |
| gatattagat | acggtgtttc | gagaattgca | tatagtaaag | actttgaaac | tctcaaagtt | 360 |
| gattttctta | gcaagctacc | tgaaatgctg | aaaatgttcg | aagatcgttt | atgtcataaa | 420 |
| acatatttaa | atggtgatca | tgtaacccat | cctgacttca | tgttgtatga | cgctcttgat | 480 |
| gttgttttat | acatggaccc | aatgtgcctg | gatgcgttcc | caaaattagt | ttgttttaaa | 540 |
| aaacgtattg | aagctatccc | acaaattgat | aagtacttga | atccagcaa | gtatatagca | 600 |
| tggccttgc | agggctggca | agccacgttt | ggtggtggcg | accatcctcc | aaaatcggat | 660 |
| ggttcaacta | gtggttctgg | tcatcaccat | caccatcact | ccgcgggtct | ggtgccacgc | 720 |
| ggtagtactg | caattggtat | gaaagaaacc | gctgctgcta | aattcgaacg | ccagcacatg | 780 |
| gacagcccag | atctgggtac | cggtggtggc | tccggtattg | agggacgcgg | gtccatggga | 840 |
| tatcggggat | ccgagctgga | caccccaag | gacctgcagg | tgtccgagac | agccgagaca | 900 |
| agcctgaccc | tgctgtggaa | accccctg | gccaagttcg | accggtacag | actgaactac | 960 |
| agcctgccca | ctggacagtg | ggtcggcgtg | cagctgcccc | ggaacaccac | ctcctacgtg | 1020 |
| ctgcggggcc | tggaacccgg | ccaggaatac | aacgtcctgc | tgacggccga | gaagggccgg | 1080 |
| cacaagagca | agcccgccag | agtgaaggcc | agcaccgagc | aggcccccga | gctggaaaac | 1140 |
| ctgaccgtga | ccgaagtggg | ctgggacggc | tgcggctga | actggaccgc | ggctgaccag | 1200 |
| gcctatgagc | actttatcat | tcaggtgcag | gaggccaaca | aggtggaggc | agctcggaac | 1260 |
| ctcaccgtgc | ctggcagcct | tcgggctgtg | gacataccgg | gcctcaaggc | tgctacgcct | 1320 |
| tatacagtct | ccatctatgg | ggtgatccag | ggctatagaa | caccagtgct | ctctgctgag | 1380 |
| gcctccacag | gcgaaacacc | gaacctgggc | gaagtggtgg | tggcggaagt | gggttgggat | 1440 |
| gcgctgaaac | tgaactggac | cgcgccggaa | ggcgcgtatg | aatatttttt | catccaggtg | 1500 |
| caggaagcgg | ataccgttga | agcggcgcag | aacctgaccg | ttccgggcgg | tctgcgtagc | 1560 |
| accgatctgc | cggcctgaa | agcggcgacc | cattatacca | ttaccatccg | tggggtgacc | 1620 |
| caggacttct | ctaccacccc | tctgagcgtg | gaggtgctga | ccgaggaggt | acccgacatg | 1680 |
| ggcaacctga | ccgtgaccga | ggtgtcctgg | acgccctgc | ggctgaactg | gaccaccccc | 1740 |
| gacggcacct | acgaccagtt | cacaatccag | gtgcaggaag | ccgaccaggt | ggaagaagca | 1800 |
| cataatctga | ccgttccggg | tagcctgcgt | agcatggaaa | ttccgggtct | gcgtgcaggc | 1860 |
| accccgtata | ccgttaccct | gcatggtgaa | gttcgtggtc | atagcacccg | tccgctggca | 1920 |

```
gttgaagttg ttaccgaaga tctgccgcag ctgggtgatc tggcagttag cgaagttggt    1980
tgggatggtc tgcgtctgaa ttggaccgca gcagataatg catatgaaca ttttgtgatc    2040
caggtgcaag aggtgaataa agttgaagca gcccagaatc tgaccctgcc tggttcactg    2100
cgtgcagttg atattccggg actcgaggca gcaaccccgt atcgtgttag catttatggt    2160
gttattcgcg gttatcgtac accggttctg agcgcagaag caagcaccgc aaaagaaccg    2220
gaaattggta atctgaacgt gagcgatatt acaccggaat catttaatct gagctggatg    2280
gcaaccgatg gtatttttga aacctttacc atcgagatca tcgatagcaa tcgtctgctg    2340
gaaaccgtgg aatataatat tagcggtgca gaacgtaccg cacatattag cggtctgcct    2400
ccgagcaccg attttattgt ttatctgagc ggtctggcac cgagcattcg taccaaaacc    2460
attagcgcaa ccgcaaccac cgaagcactg ccgctgctgg aaaatctgac cattagcgat    2520
attaacccgt atggttttac cgtttcatgg atggcaagcg aaaatgcatt tgatagcttt    2580
ctggttacag ttgtggatag cggtaaactg ctggacccgc aagaatttac cctgagcggc    2640
acccagcgca aactggaact gcgtggtctg attaccggta ttggttatga agttatggtg    2700
agcggtttta cccagggtca tcagaccaaa ccgctgcgtg cagaaattgt taccgaagca    2760
atgggtagcc cgaaagaagt tattttttcc gatatcaccg agaattcggc aaccgttagc    2820
tggcgtgcac cgaccgcaca ggttgaaagc tttcgtatta cctatgttcc gattaccggt    2880
ggcaccccga gcatggttac agttgatggc accaaaaccc agaccgtct ggttaaactg    2940 attccgggtg ttgaatatct ggttagcatt attgccatga aaggctttga agaaagcgaa    3000
ccggttagcg gtagctttac cacagctagc ggcctgaacg acatcttcga ggctcagaaa    3060
atcgaatggc acgaaggtac ccatcaccat caccaccact aa    3102
```

<210> SEQ ID NO 2
<211> LENGTH: 2566
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: muTNC
<400> SEQUENCE: 2

```
tatgtccccT atactaggtt attggaaaat taagggcctt gtgcaaccca ctcgacttct     60
tttggaatat cttgaagaaa aatatgaaga gcatttgtat gagcgcgatg aaggtgataa    120
atggcgaaac aaaaagtttg aattgggttt ggagtttccc aatcttcctt attatattga    180
tggtgatgtt aaattaacac agtctatggc catcatacgt tatatagctg acaagcacaa    240
catgtttggg ggttgtccaa agagcgtgca gagatttcaa atgcttgaag gagcggtttt    300
ggatattaga tacggtgttt cgagaattgc atatagtaaa gactttgaaa ctctcaaagt    360 tgatttctt agcaagctac ctgaaatgct gaaaatgttc gaagatcgtt tatgtcataa    420
aacatattta aatggtgatc atgtaaccca tcctgacttc atgttgtatg cgctcttga    480 tgttgttttta tacatggacc caatgtgcct ggatgcgttc ccaaaattag tttgttttaa    540
aaaacgtatt gaagctatcc cacaaattga taagtacttg aaatccagca agtatatagc    600 atggccttttg cagggctggc aagccacgtt tggtggtggc gaccatcctc caaaatcgga    660
tggttcaact agtggttctg gtcatcacca tcaccatcac tccgcgggtc tggtgccacg    720
cggtagtact gcaattggta tgaaagaaac cgctgctgct aaattcgaac gccagcacat    780
```

```
ggacagccca gatctgggta ccggtggtgg ctccggtatt gagggacgcg ggtccatggg      840
atatcgggga tccgagctgg acaccccaa ggacctgcag gtgtccgaga cagccgagac       900
aagcctgacc ctgctgtgga aaccccct ggccaagttc gaccggtaca gactgaacta       960
cagcctgccc actggacagt gggtcggcgt gcagctgccc cggaacacca cctcctacgt    1020 gctgcgggc ctggaacccg ccaggaata caacgtcctg ctgacggccg agaagggccg     1080
gcacaagagc aagcccgcca gagtgaaggc cagcaccgag gaagtgccca gcctggaaaa    1140
cctgaccgtg accgaggccg gctgggacgg cctgcggctg aactggaccg ccgacgacct    1200
ggcctacgag tacttcgtga tccaggtgca ggaagccaac aacgtcgaga cagcccacaa    1260
cttcaccgtg cccggcaacc tgagagccgc cgacatcccc ggcctgaagg tggccacatc    1320
ctaccgggtg tccatctacg gcgtggccag gggctaccgg accccgtgc tgtccgccga    1380 gacaagcacc ggcaccacgc cgaacctggg cgaagtgacc gtggcggaag tgggttggga    1440
tgcgctgacc ctgaattgga ccgcaccgga aggcgcgtat aaaaactttt tcatccaggt    1500
gctggaagcg ataccaccc agaccgtgca gaacctgacc gtgccgggtg gtctgcgtag    1560
cgtagatctg cctggtctga aagcagcaac ccgctattac attaccctgc gtggtgttac    1620
ccaggatttt ggcaccgcac cgctgagcgt tgaagttctg accgaggatc tgccgcagct    1680
gggtggtctg agcgttaccg aagttagttg ggatggtctg accctgaatt ggaccaccga    1740
tgatctggca tataaacatt ttgtggtgca ggttcaagag gccaataatg ttgaagcagc    1800
acagaatctg accgttccgg gtagcctgcg tgcagttgat attccgggac tgaaagccga    1860 tacccgtat cgtgttagca tttatggtgt tattcagggt tatcgtaccc cgatgctgag    1920
caccgatgtt agcacagcac gtgaaccgga aattggtaat ctgaatgtta gtgatgtgac    1980
cccgaaatca tttaatctga gctggaccgc aaccgatgtt attttgata tgtttaccat    2040 tgaaattatt gatagcaatc gcctgctgca gaccgcagaa cataacatta gcggtgcaga    2100
acgtaccgca catattagcg gtctgcctcc gagcaccgat tttattgttt atctgagcgg    2160
tattgcaccg agcattcgta ccaaaaccat tagcaccacc gcaaccaccg aagcactgac    2220
cgcaatgggt agcccgaaag aagtgatttt tagcgatatt accgaaaata gcgccaccgt    2280
ttcatggcgt gcaccgaccg cacaggttga aagctttcgt attacctatg ttccgattac    2340
cggtggcacc ccgagcatgg ttaccgttga tggcaccaaa acccagaccc gtctggttaa    2400
actgattccg ggtgttgaat atctggttag cattattgcc atgaaaggct ttgaagaaag    2460
cgaaccggtt agcggtagct ttaccacagc tagcggcctg aacgacatct tcgaggctca    2520
gaaaatcgaa tggcacgaag gtacccatca ccatcaccac cactaa                   2566
```

<210> SEQ ID NO 3
<211> LENGTH: 2565
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cynoTNC

<400> SEQUENCE: 3

```
atgtcccta tactaggtta ttggaaaatt aagggccttg tgcaacccac tcgacttctt        60
ttggaatatc ttgaagaaaa atatgaagag catttgtatg agcgcgatga aggtgataaa      120
tggcgaaaca aaaagtttga attgggtttg gagtttccca atcttcctta ttatattgat      180
```

```
ggtgatgtta aattaacaca gtctatggcc atcatacgtt atatagctga caagcacaac    240
atgttgggtg gttgtccaaa agagcgtgca gagatttcaa tgcttgaagg agcggttttg    300
gatattagat acgtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg gatgcgttcc caaaattagt ttgtttaaa     540 aaacgtattg aagctatccc acaaattgat aagtacttga atccagcaa gtatatagca    600 tggcctttgc agggctggca agccacgttt ggtggtggcg accatcctcc aaaatcggat    660
ggttcaacta gtggttctgg tcatcaccat caccatcact ccgcgggtct ggtgccacgc    720
ggtagtactg caattggtat gaaagaaacc gctgctgcta aattcgaacg ccagcacatg    780
gacagcccag atctgggtac cggtggtggc tccggtattg agggacgcgg gtccatggga    840
tatcggggat ccgaactgga taccccgaaa gatctgcgtg ttagcgaaac cgcagaaacc    900
agcctgaccc tgttttggaa aacaccgctg gcaaaatttg atcgttatcg tctgaattat    960
agcctgccga ccggtcagtg ggttggtgtt cagctgcctc gtaataccac cagttatgtt   1020
ctgcgtggtc tggaacccgg gtcaagaatat aacgttctgc tgaccgcaga aaaaggtcgt   1080
cataaaagca aaccggcacg tgttaaagca agcaccgaac aggcaccgga actggaaaat   1140
ctgaccgtta ccgaagttgg ctgggatggc ctgcgcctga actggacggc tgcggaccag   1200
gcctacgaac acttcgttat ccaggtgcaa gaagccaaca agtagaagc cgctcagaat    1260 ctgacggttc cgggaaatct gcgtgcagtt gatattccgg gtctgaaagc gcaaccccg    1320 tataccgtta gcatttatgg tgttattcag ggttatcgta caccggttct gagtgccgaa   1380
gccagcaccg tgaaacccc gaatctgggt gaagttatgg ttagcgaagt gggctgggat    1440
gcactgaaac tgaattggac agttccggaa ggtgcctatg aatacttttt cattcaggtt   1500
caagaagcgg ataccgttga agccgctcag aatcataccg ttccgggtgg tctgcgtagc   1560
accgatctgc ctggcctgaa agccgctacc cattacacca ttaccattcg tggtgttacc   1620
caggatttta gcaccacacc gctgagcgtt gaagttctga cagaagaact gccgcagctg   1680
ggtgatctgg cagttagcga agttggttgg gatggtctgc gtctgaattg gaccgcagca   1740
gatcaggcat atgaacattt tgttatccag gtgcaagaag tgaacaaagt tgaagcagca   1800
cagaatctga ccgttccggg tagcctgcgt gcagttgata ttccgggtct gaaagcagca   1860
accccgtata ccgttagcat ttatggtgtt attcgcggtt atcgtacacc ggttctgagc   1920
gcagaagcaa gcaccgcaaa agaaccggaa attggtaatc tgaacgtgag cgatattaca   1980
ccggaaagtt ttagcctgag ctggaccgca accgatggta tttttgaaac ctttaccatc   2040
gagatcatcg atagcaatcg tctgctggaa atcgtggaat ataacattag cggtgcagaa   2100
cgtaccgcac atattagcgg tctgcctccg agcaccgatt ttattgttta tctgagcggt   2160
ctggcaccga gctttcgtac caaaaccatt agcgcaaccg caaccaccga agcactgacc   2220
gcaatgggta gcccgaaaga agtgattttt agcgatatta ccgaaaatag cgccaccgtt   2280
tcatggcgtg caccgaccgc acaggttgaa agctttcgta ttacctatgt tccgattacc   2340
ggtggcaccc cgagcatggt taccgtggat ggcaccaaaa cccagacccg tctggttaaa   2400
ctggttccgg gtgttgaata tctggtgaat atcattgcca tgaaaggctt tgaagaaagc   2460
gaaccggtta gcggtagctt taccaccgct agcggcctga cgacatctt cgaggctcag   2520 aaaatcgaat ggcacgaagg taccatcac catcaccacc actaa                    2565
```

-continued

```
<210> SEQ ID NO 4
<211> LENGTH: 1033
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: huTNC

<400> SEQUENCE: 4

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Gly Ser Thr Ser
    210                 215                 220

Gly Ser Gly His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Ile Glu Gly Arg Gly Ser Met Gly Tyr Arg Gly Ser Glu Leu Asp Thr
        275                 280                 285

Pro Lys Asp Leu Gln Val Ser Glu Thr Ala Glu Thr Ser Leu Thr Leu
    290                 295                 300

Leu Trp Lys Thr Pro Leu Ala Lys Phe Asp Arg Tyr Arg Leu Asn Tyr
305                 310                 315                 320

Ser Leu Pro Thr Gly Gln Trp Val Gly Val Gln Leu Pro Arg Asn Thr
                325                 330                 335

Thr Ser Tyr Val Leu Arg Gly Leu Glu Pro Gly Gln Glu Tyr Asn Val
            340                 345                 350
```

```
Leu Leu Thr Ala Glu Lys Gly Arg His Lys Ser Lys Pro Ala Arg Val
        355                 360                 365

Lys Ala Ser Thr Glu Gln Ala Pro Glu Leu Glu Asn Leu Thr Val Thr
    370                 375                 380

Glu Val Gly Trp Asp Gly Leu Arg Leu Asn Trp Thr Ala Ala Asp Gln
385                 390                 395                 400

Ala Tyr Glu His Phe Ile Ile Gln Val Gln Glu Ala Asn Lys Val Glu
                405                 410                 415

Ala Ala Arg Asn Leu Thr Val Pro Gly Ser Leu Arg Ala Val Asp Ile
            420                 425                 430

Pro Gly Leu Lys Ala Ala Thr Pro Tyr Thr Val Ser Ile Tyr Gly Val
        435                 440                 445

Ile Gln Gly Tyr Arg Thr Pro Val Leu Ser Ala Glu Ala Ser Thr Gly
    450                 455                 460

Glu Thr Pro Asn Leu Gly Glu Val Val Ala Glu Val Gly Trp Asp
465                 470                 475                 480

Ala Leu Lys Leu Asn Trp Thr Ala Pro Glu Gly Ala Tyr Glu Tyr Phe
                485                 490                 495

Phe Ile Gln Val Gln Glu Ala Asp Thr Val Glu Ala Ala Gln Asn Leu
                500                 505                 510

Thr Val Pro Gly Gly Leu Arg Ser Thr Asp Leu Pro Gly Leu Lys Ala
            515                 520                 525

Ala Thr His Tyr Thr Ile Thr Ile Arg Gly Val Thr Gln Asp Phe Ser
        530                 535                 540

Thr Thr Pro Leu Ser Val Glu Val Leu Thr Glu Val Pro Asp Met
545                 550                 555                 560

Gly Asn Leu Thr Val Thr Glu Val Ser Trp Asp Ala Leu Arg Leu Asn
                565                 570                 575

Trp Thr Thr Pro Asp Gly Thr Tyr Asp Gln Phe Thr Ile Gln Val Gln
            580                 585                 590

Glu Ala Asp Gln Val Glu Glu Ala His Asn Leu Thr Val Pro Gly Ser
        595                 600                 605

Leu Arg Ser Met Glu Ile Pro Gly Leu Arg Ala Gly Thr Pro Tyr Thr
    610                 615                 620

Val Thr Leu His Gly Glu Val Arg Gly His Ser Thr Arg Pro Leu Ala
625                 630                 635                 640

Val Glu Val Val Thr Glu Asp Leu Pro Gln Leu Gly Asp Leu Ala Val
                645                 650                 655

Ser Glu Val Gly Trp Asp Gly Leu Arg Leu Asn Trp Thr Ala Ala Asp
            660                 665                 670

Asn Ala Tyr Glu His Phe Val Ile Gln Val Gln Glu Val Asn Lys Val
        675                 680                 685

Glu Ala Ala Gln Asn Leu Thr Leu Pro Gly Ser Leu Arg Ala Val Asp
690                 695                 700

Ile Pro Gly Leu Glu Ala Ala Thr Pro Tyr Arg Val Ser Ile Tyr Gly
705                 710                 715                 720

Val Ile Arg Gly Tyr Arg Thr Pro Val Leu Ser Ala Glu Ala Ser Thr
                725                 730                 735

Ala Lys Glu Pro Glu Ile Gly Asn Leu Asn Val Ser Asp Ile Thr Pro
            740                 745                 750

Glu Ser Phe Asn Leu Ser Trp Met Ala Thr Asp Gly Ile Phe Glu Thr
        755                 760                 765
```

Phe Thr Ile Glu Ile Ile Asp Ser Asn Arg Leu Leu Glu Thr Val Glu
            770                 775                 780

Tyr Asn Ile Ser Gly Ala Glu Arg Thr Ala His Ile Ser Gly Leu Pro
785                 790                 795                 800

Pro Ser Thr Asp Phe Ile Val Tyr Leu Ser Gly Leu Ala Pro Ser Ile
            805                 810                 815

Arg Thr Lys Thr Ile Ser Ala Thr Ala Thr Thr Glu Ala Leu Pro Leu
            820                 825                 830

Leu Glu Asn Leu Thr Ile Ser Asp Ile Asn Pro Tyr Gly Phe Thr Val
            835                 840                 845

Ser Trp Met Ala Ser Glu Asn Ala Phe Asp Ser Phe Leu Val Thr Val
850                 855                 860

Val Asp Ser Gly Lys Leu Leu Asp Pro Gln Glu Phe Thr Leu Ser Gly
865                 870                 875                 880

Thr Gln Arg Lys Leu Glu Leu Arg Gly Leu Ile Thr Gly Ile Gly Tyr
                885                 890                 895

Glu Val Met Val Ser Gly Phe Thr Gln Gly His Gln Thr Lys Pro Leu
            900                 905                 910

Arg Ala Glu Ile Val Thr Glu Ala Met Gly Ser Pro Lys Glu Val Ile
            915                 920                 925

Phe Ser Asp Ile Thr Glu Asn Ser Ala Thr Val Ser Trp Arg Ala Pro
930                 935                 940

Thr Ala Gln Val Glu Ser Phe Arg Ile Thr Tyr Val Pro Ile Thr Gly
945                 950                 955                 960

Gly Thr Pro Ser Met Val Thr Val Asp Gly Thr Lys Thr Gln Thr Arg
            965                 970                 975

Leu Val Lys Leu Ile Pro Gly Val Glu Tyr Leu Val Ser Ile Ile Ala
            980                 985                 990

Met Lys Gly Phe Glu Glu Ser Glu Pro Val Ser Gly Ser Phe Thr Thr
            995                 1000                1005

Ala Ser Gly Leu Asn Asp Ile Phe Glu Ala Gln Lys Ile Glu Trp
   1010                1015                1020

His Glu Gly Thr His His His His His His
   1025                1030

<210> SEQ ID NO 5
<211> LENGTH: 854
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: muTNC

<400> SEQUENCE: 5

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

```
Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Gly Ser Thr Ser
    210                 215                 220

Gly Ser Gly His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Ile Glu Gly Arg Gly Ser Met Gly Tyr Arg Gly Ser Glu Leu Asp Thr
        275                 280                 285

Pro Lys Asp Leu Gln Val Ser Glu Thr Ala Glu Thr Ser Leu Thr Leu
    290                 295                 300

Leu Trp Lys Thr Pro Leu Ala Lys Phe Asp Arg Tyr Arg Leu Asn Tyr
305                 310                 315                 320

Ser Leu Pro Thr Gly Gln Trp Val Gly Val Gln Leu Pro Arg Asn Thr
                325                 330                 335

Thr Ser Tyr Val Leu Arg Gly Leu Glu Pro Gly Gln Glu Tyr Asn Val
            340                 345                 350

Leu Leu Thr Ala Glu Lys Gly Arg His Lys Ser Lys Pro Ala Arg Val
        355                 360                 365

Lys Ala Ser Thr Glu Glu Val Pro Ser Leu Glu Asn Leu Thr Val Thr
    370                 375                 380

Glu Ala Gly Trp Asp Gly Leu Arg Leu Asn Trp Thr Ala Asp Asp Leu
385                 390                 395                 400

Ala Tyr Glu Tyr Phe Val Ile Gln Val Gln Glu Ala Asn Asn Val Glu
                405                 410                 415

Thr Ala His Asn Phe Thr Val Pro Gly Asn Leu Arg Ala Ala Asp Ile
            420                 425                 430

Pro Gly Leu Lys Val Ala Thr Ser Tyr Arg Val Ser Ile Tyr Gly Val
        435                 440                 445

Ala Arg Gly Tyr Arg Thr Pro Val Leu Ser Ala Glu Thr Ser Thr Gly
    450                 455                 460

Thr Thr Pro Asn Leu Gly Glu Val Thr Val Ala Glu Val Gly Trp Asp
465                 470                 475                 480

Ala Leu Thr Leu Asn Trp Thr Ala Pro Glu Gly Ala Tyr Lys Asn Phe
                485                 490                 495

Phe Ile Gln Val Leu Glu Ala Asp Thr Thr Gln Thr Val Gln Asn Leu
```

```
                500             505             510
Thr Val Pro Gly Gly Leu Arg Ser Val Asp Leu Pro Gly Leu Lys Ala
            515                 520             525

Ala Thr Arg Tyr Tyr Ile Thr Leu Arg Gly Val Thr Gln Asp Phe Gly
        530                 535             540

Thr Ala Pro Leu Ser Val Glu Val Leu Thr Glu Asp Leu Pro Gln Leu
545                 550             555                 560

Gly Gly Leu Ser Val Thr Glu Val Ser Trp Asp Gly Leu Thr Leu Asn
                565             570             575

Trp Thr Thr Asp Asp Leu Ala Tyr Lys His Phe Val Gln Val Gln
            580             585             590

Glu Ala Asn Asn Val Glu Ala Ala Gln Asn Leu Thr Val Pro Gly Ser
            595             600             605

Leu Arg Ala Val Asp Ile Pro Gly Leu Lys Ala Asp Thr Pro Tyr Arg
        610                 615             620

Val Ser Ile Tyr Gly Val Ile Gln Gly Tyr Arg Thr Pro Met Leu Ser
625                 630             635             640

Thr Asp Val Ser Thr Ala Arg Glu Pro Glu Ile Gly Asn Leu Asn Val
            645             650             655

Ser Asp Val Thr Pro Lys Ser Phe Asn Leu Ser Trp Thr Ala Thr Asp
            660             665             670

Gly Ile Phe Asp Met Phe Thr Ile Glu Ile Asp Ser Asn Arg Leu
        675             680             685

Leu Gln Thr Ala Glu His Asn Ile Ser Gly Ala Glu Arg Thr Ala His
    690                 695             700

Ile Ser Gly Leu Pro Pro Ser Thr Asp Phe Ile Val Tyr Leu Ser Gly
705             710                 715             720

Ile Ala Pro Ser Ile Arg Thr Lys Thr Ile Ser Thr Thr Ala Thr Thr
            725             730             735

Glu Ala Leu Thr Ala Met Gly Ser Pro Lys Glu Val Ile Phe Ser Asp
        740             745             750

Ile Thr Glu Asn Ser Ala Thr Val Ser Trp Arg Ala Pro Thr Ala Gln
        755             760             765

Val Glu Ser Phe Arg Ile Thr Tyr Val Pro Ile Thr Gly Gly Thr Pro
    770             775             780

Ser Met Val Thr Val Asp Gly Thr Lys Thr Gln Thr Arg Leu Val Lys
785             790             795             800

Leu Ile Pro Gly Val Glu Tyr Leu Val Ser Ile Ile Ala Met Lys Gly
                805             810             815

Phe Glu Glu Ser Glu Pro Val Ser Gly Ser Phe Thr Thr Ala Ser Gly
            820             825             830

Leu Asn Asp Ile Phe Glu Ala Gln Lys Ile Glu Trp His Glu Gly Thr
            835             840             845

His His His His His His
    850

<210> SEQ ID NO 6
<211> LENGTH: 854
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cynoTNC
```

<400> SEQUENCE: 6

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
    210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Ser Gly Gly
            260                 265                 270

Ile Glu Gly Arg Gly Ser Met Gly Tyr Arg Gly Ser Glu Leu Asp Thr
        275                 280                 285

Pro Lys Asp Leu Arg Val Ser Glu Thr Ala Glu Thr Ser Leu Thr Leu
    290                 295                 300

Phe Trp Lys Thr Pro Leu Ala Lys Phe Asp Arg Tyr Arg Leu Asn Tyr
305                 310                 315                 320

Ser Leu Pro Thr Gly Gln Trp Val Gly Val Gln Leu Pro Arg Asn Thr
                325                 330                 335

Thr Ser Tyr Val Leu Arg Gly Leu Glu Pro Gly Gln Glu Tyr Asn Val
            340                 345                 350

Leu Leu Thr Ala Glu Lys Gly Arg His Lys Ser Lys Pro Ala Arg Val
        355                 360                 365

Lys Ala Ser Thr Glu Gln Ala Pro Glu Leu Glu Asn Leu Thr Val Thr
    370                 375                 380

Glu Val Gly Trp Asp Gly Leu Arg Leu Asn Trp Thr Ala Ala Asp Gln
385                 390                 395                 400

Ala Tyr Glu His Phe Val Ile Gln Val Gln Glu Ala Asn Lys Val Glu
                405                 410                 415
```

Ala Ala Gln Asn Leu Thr Val Pro Gly Asn Leu Arg Ala Val Asp Ile
            420                 425                 430

Pro Gly Leu Lys Ala Ala Thr Pro Tyr Thr Val Ser Ile Tyr Gly Val
        435                 440                 445

Ile Gln Gly Tyr Arg Thr Pro Val Leu Ser Ala Glu Ala Ser Thr Gly
    450                 455                 460

Glu Thr Pro Asn Leu Gly Glu Val Met Val Ser Glu Val Gly Trp Asp
465                 470                 475                 480

Ala Leu Lys Leu Asn Trp Thr Val Pro Glu Gly Ala Tyr Glu Tyr Phe
                485                 490                 495

Phe Ile Gln Val Gln Glu Ala Asp Thr Val Glu Ala Ala Gln Asn His
            500                 505                 510

Thr Val Pro Gly Gly Leu Arg Ser Thr Asp Leu Pro Gly Leu Lys Ala
        515                 520                 525

Ala Thr His Tyr Thr Ile Thr Ile Arg Gly Val Thr Gln Asp Phe Ser
    530                 535                 540

Thr Thr Pro Leu Ser Val Glu Val Leu Thr Glu Glu Leu Pro Gln Leu
545                 550                 555                 560

Gly Asp Leu Ala Val Ser Glu Val Gly Trp Asp Gly Leu Arg Leu Asn
                565                 570                 575

Trp Thr Ala Ala Asp Gln Ala Tyr Glu His Phe Val Ile Gln Val Gln
            580                 585                 590

Glu Val Asn Lys Val Glu Ala Ala Gln Asn Leu Thr Val Pro Gly Ser
        595                 600                 605

Leu Arg Ala Val Asp Ile Pro Gly Leu Lys Ala Ala Thr Pro Tyr Thr
    610                 615                 620

Val Ser Ile Tyr Gly Val Ile Arg Gly Tyr Arg Thr Pro Val Leu Ser
625                 630                 635                 640

Ala Glu Ala Ser Thr Ala Lys Glu Pro Glu Ile Gly Asn Leu Asn Val
                645                 650                 655

Ser Asp Ile Thr Pro Glu Ser Phe Ser Leu Ser Trp Thr Ala Thr Asp
            660                 665                 670

Gly Ile Phe Glu Thr Phe Thr Ile Glu Ile Ile Asp Ser Asn Arg Leu
        675                 680                 685

Leu Glu Ile Val Glu Tyr Asn Ile Ser Gly Ala Glu Arg Thr Ala His
    690                 695                 700

Ile Ser Gly Leu Pro Pro Ser Thr Asp Phe Ile Val Tyr Leu Ser Gly
705                 710                 715                 720

Leu Ala Pro Ser Phe Arg Thr Lys Thr Ile Ser Ala Thr Ala Thr Thr
                725                 730                 735

Glu Ala Leu Thr Ala Met Gly Ser Pro Lys Glu Val Ile Phe Ser Asp
            740                 745                 750

Ile Thr Glu Asn Ser Ala Thr Val Ser Trp Arg Ala Pro Thr Ala Gln
        755                 760                 765

Val Glu Ser Phe Arg Ile Thr Tyr Val Pro Ile Thr Gly Gly Thr Pro
    770                 775                 780

Ser Met Val Thr Val Asp Gly Thr Lys Thr Gln Thr Arg Leu Val Lys
785                 790                 795                 800

Leu Val Pro Gly Val Glu Tyr Leu Val Asn Ile Ile Ala Met Lys Gly
                805                 810                 815

Phe Glu Glu Ser Glu Pro Val Ser Gly Ser Phe Thr Ala Ser Gly
            820                 825                 830

Leu Asn Asp Ile Phe Glu Ala Gln Lys Ile Glu Trp His Glu Gly Thr
            835                 840                 845

His His His His His His
    850

<210> SEQ ID NO 7
<211> LENGTH: 1033
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GST huTNC fn5 A1234 BC fn6 B

<400> SEQUENCE: 7

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
    210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Ile Glu Gly Arg Gly Ser Met Gly Tyr Arg Gly Ser Glu Leu Asp Thr
        275                 280                 285

Pro Lys Asp Leu Gln Val Ser Glu Thr Ala Glu Thr Ser Leu Thr Leu
    290                 295                 300

Leu Trp Lys Thr Pro Leu Ala Lys Phe Asp Arg Tyr Arg Leu Asn Tyr
305                 310                 315                 320

-continued

Ser Leu Pro Thr Gly Gln Trp Val Gly Val Gln Leu Pro Arg Asn Thr
            325                 330                 335

Thr Ser Tyr Val Leu Arg Gly Leu Glu Pro Gly Gln Glu Tyr Asn Val
        340                 345                 350

Leu Leu Thr Ala Glu Lys Gly Arg His Lys Ser Lys Pro Ala Arg Val
    355                 360                 365

Lys Ala Ser Thr Glu Gln Ala Pro Glu Leu Glu Asn Leu Thr Val Thr
370                 375                 380

Glu Val Gly Trp Asp Gly Leu Arg Leu Asn Trp Thr Ala Ala Asp Gln
385                 390                 395                 400

Ala Tyr Glu His Phe Ile Ile Gln Val Gln Glu Ala Asn Lys Val Glu
                405                 410                 415

Ala Ala Arg Asn Leu Thr Val Pro Gly Ser Leu Arg Ala Val Asp Ile
            420                 425                 430

Pro Gly Leu Lys Ala Ala Thr Pro Tyr Thr Val Ser Ile Tyr Gly Val
        435                 440                 445

Ile Gln Gly Tyr Arg Thr Pro Val Leu Ser Ala Glu Ala Ser Thr Gly
    450                 455                 460

Glu Thr Pro Asn Leu Gly Glu Val Val Val Ala Glu Val Gly Trp Asp
465                 470                 475                 480

Ala Leu Lys Leu Asn Trp Thr Ala Pro Glu Gly Ala Tyr Glu Tyr Phe
                485                 490                 495

Phe Ile Gln Val Gln Glu Ala Asp Thr Val Glu Ala Ala Gln Asn Leu
                500                 505                 510

Thr Val Pro Gly Gly Leu Arg Ser Thr Asp Leu Pro Gly Leu Lys Ala
        515                 520                 525

Ala Thr His Tyr Thr Ile Thr Ile Arg Gly Val Thr Gln Asp Phe Ser
    530                 535                 540

Thr Thr Pro Leu Ser Val Glu Val Leu Thr Glu Glu Val Pro Asp Met
545                 550                 555                 560

Gly Asn Leu Thr Val Thr Glu Val Ser Trp Asp Ala Leu Arg Leu Asn
                565                 570                 575

Trp Thr Thr Pro Asp Gly Thr Tyr Asp Gln Phe Thr Ile Gln Val Gln
        580                 585                 590

Glu Ala Asp Gln Val Glu Glu Ala His Asn Leu Thr Val Pro Gly Ser
    595                 600                 605

Leu Arg Ser Met Glu Ile Pro Gly Leu Arg Ala Gly Thr Pro Tyr Thr
610                 615                 620

Val Thr Leu His Gly Glu Val Arg Gly His Ser Thr Arg Pro Leu Ala
625                 630                 635                 640

Val Glu Val Val Thr Glu Asp Leu Pro Gln Leu Gly Asp Leu Ala Val
                645                 650                 655

Ser Glu Val Gly Trp Asp Gly Leu Arg Leu Asn Trp Thr Ala Ala Asp
        660                 665                 670

Asn Ala Tyr Glu His Phe Val Ile Gln Val Gln Glu Val Asn Lys Val
    675                 680                 685

Glu Ala Ala Gln Asn Leu Thr Leu Pro Gly Ser Leu Arg Ala Val Asp
690                 695                 700

Ile Pro Gly Leu Glu Ala Thr Pro Tyr Arg Val Ser Ile Tyr Gly
705                 710                 715                 720

Val Ile Arg Gly Tyr Arg Thr Pro Val Leu Ser Ala Glu Ala Ser Thr
                725                 730                 735

Ala Lys Glu Pro Glu Ile Gly Asn Leu Asn Val Ser Asp Ile Thr Pro

```
                    740                 745                 750
Glu Ser Phe Asn Leu Ser Trp Met Ala Thr Asp Gly Ile Phe Glu Thr
                755                 760                 765

Phe Thr Ile Glu Ile Ile Asp Ser Asn Arg Leu Leu Glu Thr Val Glu
            770                 775                 780

Tyr Asn Ile Ser Gly Ala Glu Arg Thr Ala His Ile Ser Gly Leu Pro
785                 790                 795                 800

Pro Ser Thr Asp Phe Ile Val Tyr Leu Ser Gly Leu Ala Pro Ser Ile
                805                 810                 815

Arg Thr Lys Thr Ile Ser Ala Thr Ala Thr Thr Glu Ala Leu Pro Leu
            820                 825                 830

Leu Glu Asn Leu Thr Ile Ser Asp Ile Asn Pro Tyr Gly Phe Thr Val
                835                 840                 845

Ser Trp Met Ala Ser Glu Asn Ala Phe Asp Ser Phe Leu Val Thr Val
            850                 855                 860

Val Asp Ser Gly Lys Leu Leu Asp Pro Gln Glu Phe Thr Leu Ser Gly
865                 870                 875                 880

Thr Gln Arg Lys Leu Glu Leu Arg Gly Leu Ile Thr Gly Ile Gly Tyr
                885                 890                 895

Glu Val Met Val Ser Gly Phe Thr Gln Gly His Gln Thr Lys Pro Leu
            900                 905                 910

Arg Ala Glu Ile Val Thr Glu Ala Met Gly Ser Pro Lys Glu Val Ile
                915                 920                 925

Phe Ser Asp Ile Thr Glu Asn Ser Ala Thr Val Ser Trp Arg Ala Pro
            930                 935                 940

Thr Ala Gln Val Glu Ser Phe Arg Ile Thr Tyr Val Pro Ile Thr Gly
945                 950                 955                 960

Gly Thr Pro Ser Met Val Thr Val Asp Gly Thr Lys Thr Gln Thr Arg
                965                 970                 975

Leu Val Lys Leu Ile Pro Gly Val Glu Tyr Leu Val Ser Ile Ile Ala
            980                 985                 990

Met Lys Gly Phe Glu Glu Ser Glu Pro Val Ser Gly Ser Phe Thr Thr
                995                 1000                1005

Ala Ser Gly Leu Asn Asp Ile Phe Glu Ala Gln Lys Ile Glu Trp
        1010                1015                1020

His Glu Gly Thr His His His His His His
        1025                1030

<210> SEQ ID NO 8
<211> LENGTH: 854
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GST huTNCfn5 mu A124 BC hu fn6 B

<400> SEQUENCE: 8

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
```

```
                50                  55                  60
Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
                115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
                195                 200                 205

Thr Phe Gly Gly Asp His Pro Pro Lys Ser Asp Gly Ser Thr Ser
210                 215                 220

Gly Ser Gly His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Ser Gly
                260                 265                 270

Ile Glu Gly Arg Gly Ser Met Gly Tyr Arg Gly Ser Glu Leu Asp Thr
                275                 280                 285

Pro Lys Asp Leu Gln Val Ser Glu Thr Ala Glu Thr Ser Leu Thr Leu
                290                 295                 300

Leu Trp Lys Thr Pro Leu Ala Lys Phe Asp Arg Tyr Arg Leu Asn Tyr
305                 310                 315                 320

Ser Leu Pro Thr Gly Gln Trp Val Gly Val Gln Leu Pro Arg Asn Thr
                325                 330                 335

Thr Ser Tyr Val Leu Arg Gly Leu Glu Pro Gly Gln Glu Tyr Asn Val
                340                 345                 350

Leu Leu Thr Ala Glu Lys Gly Arg His Lys Ser Lys Pro Ala Arg Val
                355                 360                 365

Lys Ala Ser Thr Glu Glu Val Pro Ser Leu Glu Asn Leu Thr Val Thr
370                 375                 380

Glu Ala Gly Trp Asp Gly Leu Arg Leu Asn Trp Thr Ala Asp Asp Leu
385                 390                 395                 400

Ala Tyr Glu Tyr Phe Val Ile Gln Val Gln Glu Ala Asn Asn Val Glu
                405                 410                 415

Thr Ala His Asn Phe Thr Val Pro Gly Asn Leu Arg Ala Ala Asp Ile
                420                 425                 430

Pro Gly Leu Lys Val Ala Thr Ser Tyr Arg Val Ser Ile Tyr Gly Val
                435                 440                 445

Ala Arg Gly Tyr Arg Thr Pro Val Leu Ser Ala Glu Thr Ser Thr Gly
                450                 455                 460

Thr Thr Pro Asn Leu Gly Glu Val Thr Val Ala Glu Val Gly Trp Asp
465                 470                 475                 480
```

Ala Leu Thr Leu Asn Trp Thr Ala Pro Glu Gly Ala Tyr Lys Asn Phe
            485                 490                 495

Phe Ile Gln Val Leu Glu Ala Asp Thr Thr Gln Thr Val Gln Asn Leu
        500                 505                 510

Thr Val Pro Gly Gly Leu Arg Ser Val Asp Leu Pro Gly Leu Lys Ala
        515                 520                 525

Ala Thr Arg Tyr Tyr Ile Thr Leu Arg Gly Val Thr Gln Asp Phe Gly
        530                 535                 540

Thr Ala Pro Leu Ser Val Glu Val Leu Thr Glu Asp Leu Pro Gln Leu
545                 550                 555                 560

Gly Gly Leu Ser Val Thr Glu Val Ser Trp Asp Gly Leu Thr Leu Asn
            565                 570                 575

Trp Thr Thr Asp Asp Leu Ala Tyr Lys His Phe Val Val Gln Val Gln
            580                 585                 590

Glu Ala Asn Asn Val Glu Ala Ala Gln Asn Leu Thr Val Pro Gly Ser
            595                 600                 605

Leu Arg Ala Val Asp Ile Pro Gly Leu Lys Ala Asp Thr Pro Tyr Arg
    610                 615                 620

Val Ser Ile Tyr Gly Val Ile Gln Gly Tyr Arg Thr Pro Met Leu Ser
625                 630                 635                 640

Thr Asp Val Ser Thr Ala Arg Glu Pro Glu Ile Gly Asn Leu Asn Val
            645                 650                 655

Ser Asp Val Thr Pro Lys Ser Phe Asn Leu Ser Trp Thr Ala Thr Asp
            660                 665                 670

Gly Ile Phe Asp Met Phe Thr Ile Glu Ile Asp Ser Asn Arg Leu
            675                 680                 685

Leu Gln Thr Ala Glu His Asn Ile Ser Gly Ala Glu Arg Thr Ala His
    690                 695                 700

Ile Ser Gly Leu Pro Pro Ser Thr Asp Phe Ile Val Tyr Leu Ser Gly
705                 710                 715                 720

Ile Ala Pro Ser Ile Arg Thr Lys Thr Ile Ser Thr Thr Ala Thr Thr
            725                 730                 735

Glu Ala Leu Thr Ala Met Gly Ser Pro Lys Glu Val Ile Phe Ser Asp
            740                 745                 750

Ile Thr Glu Asn Ser Ala Thr Val Ser Trp Arg Ala Pro Thr Ala Gln
            755                 760                 765

Val Glu Ser Phe Arg Ile Thr Tyr Val Pro Ile Thr Gly Gly Thr Pro
    770                 775                 780

Ser Met Val Thr Val Asp Gly Thr Lys Thr Gln Thr Arg Leu Val Lys
785                 790                 795                 800

Leu Ile Pro Gly Val Glu Tyr Leu Val Ser Ile Ala Met Lys Gly
            805                 810                 815

Phe Glu Glu Ser Glu Pro Val Ser Gly Ser Phe Thr Thr Ala Ser Gly
            820                 825                 830

Leu Asn Asp Ile Phe Glu Ala Gln Lys Ile Glu Trp His Glu Gly Thr
            835                 840                 845

His His His His His His
    850

<210> SEQ ID NO 9
<211> LENGTH: 668
<212> TYPE: PRT
<213> ORGANISM: Artificial Sequence
<220> FEATURE:

-continued

<223> OTHER INFORMATION: Description of Artificial Sequence: Synthetic
      polypeptide
<220> FEATURE:
<223> OTHER INFORMATION: GST TNC hu fn5 B-C fn6 B

<400> SEQUENCE: 9

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
    210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Ile Glu Gly Arg Gly Ser Met Gly Tyr Arg Gly Ser Glu Leu Asp Thr
        275                 280                 285

Pro Lys Asp Leu Gln Val Ser Glu Thr Ala Glu Thr Ser Leu Thr Leu
    290                 295                 300

Leu Trp Lys Thr Pro Leu Ala Lys Phe Asp Arg Tyr Arg Leu Asn Tyr
305                 310                 315                 320

Ser Leu Pro Thr Gly Gln Trp Val Gly Val Gln Leu Pro Arg Asn Thr
                325                 330                 335

Thr Ser Tyr Val Leu Arg Gly Leu Glu Pro Gly Gln Glu Tyr Asn Val
            340                 345                 350

Leu Leu Thr Ala Glu Lys Gly Arg His Lys Ser Lys Pro Ala Arg Val
        355                 360                 365

Lys Ala Ser Thr Ala Lys Glu Pro Glu Ile Gly Asn Leu Asn Val Ser
    370                 375                 380

```
Asp Ile Thr Pro Glu Ser Phe Asn Leu Ser Trp Met Ala Thr Asp Gly
385                 390                 395                 400

Ile Phe Glu Thr Phe Thr Ile Glu Ile Ile Asp Ser Asn Arg Leu Leu
                405                 410                 415

Glu Thr Val Glu Tyr Asn Ile Ser Gly Ala Glu Arg Thr Ala His Ile
            420                 425                 430

Ser Gly Leu Pro Pro Ser Thr Asp Phe Ile Val Tyr Leu Ser Gly Leu
        435                 440                 445

Ala Pro Ser Ile Arg Thr Lys Thr Ile Ser Ala Thr Ala Thr Thr Glu
450                 455                 460

Ala Leu Pro Leu Leu Glu Asn Leu Thr Ile Ser Asp Ile Asn Pro Tyr
465                 470                 475                 480

Gly Phe Thr Val Ser Trp Met Ala Ser Glu Asn Ala Phe Asp Ser Phe
                485                 490                 495

Leu Val Thr Val Val Asp Ser Gly Lys Leu Leu Asp Pro Gln Glu Phe
                500                 505                 510

Thr Leu Ser Gly Thr Gln Arg Lys Leu Glu Leu Arg Gly Leu Ile Thr
            515                 520                 525

Gly Ile Gly Tyr Glu Val Met Val Ser Gly Phe Thr Gln Gly His Gln
530                 535                 540

Thr Lys Pro Leu Arg Ala Glu Ile Val Thr Ala Met Gly Ser Pro Lys
545                 550                 555                 560

Glu Val Ile Phe Ser Asp Ile Thr Glu Asn Ser Ala Thr Val Ser Trp
                565                 570                 575

Arg Ala Pro Thr Ala Gln Val Glu Ser Phe Arg Ile Thr Tyr Val Pro
            580                 585                 590

Ile Thr Gly Gly Thr Pro Ser Met Val Thr Val Asp Gly Thr Lys Thr
        595                 600                 605

Gln Thr Arg Leu Val Lys Leu Ile Pro Gly Val Glu Tyr Leu Val Ser
610                 615                 620

Ile Ile Ala Met Lys Gly Phe Glu Glu Ser Glu Pro Val Ser Gly Ser
625                 630                 635                 640

Phe Thr Thr Ala Ser Gly Leu Asn Asp Ile Phe Glu Ala Gln Lys Ile
                645                 650                 655

Glu Trp His Glu Gly Thr His His His His His His
                660                 665
```

<210> SEQ ID NO 10
<211> LENGTH: 853
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GST huTNC fn5 A1234 fn6 B

<400> SEQUENCE: 10

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60
```

```
Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Ile Glu Gly Arg Gly Ser Met Gly Tyr Arg Gly Ser Glu Leu Asp Thr
        275                 280                 285

Pro Lys Asp Leu Gln Val Ser Glu Thr Ala Glu Thr Ser Leu Thr Leu
290                 295                 300

Leu Trp Lys Thr Pro Leu Ala Lys Phe Asp Arg Tyr Arg Leu Asn Tyr
305                 310                 315                 320

Ser Leu Pro Thr Gly Gln Trp Val Gly Val Gln Leu Pro Arg Asn Thr
                325                 330                 335

Thr Ser Tyr Val Leu Arg Gly Leu Glu Pro Gly Gln Glu Tyr Asn Val
            340                 345                 350

Leu Leu Thr Ala Glu Lys Gly Arg His Lys Ser Lys Pro Ala Arg Val
        355                 360                 365

Lys Ala Ser Thr Glu Gln Ala Pro Glu Leu Glu Asn Leu Thr Val Thr
370                 375                 380

Glu Val Gly Trp Asp Gly Leu Arg Leu Asn Trp Thr Ala Ala Asp Gln
385                 390                 395                 400

Ala Tyr Glu His Phe Ile Ile Gln Val Gln Glu Ala Asn Lys Val Glu
                405                 410                 415

Ala Ala Arg Asn Leu Thr Val Pro Gly Ser Leu Arg Ala Val Asp Ile
            420                 425                 430

Pro Gly Leu Lys Ala Ala Thr Pro Tyr Thr Val Ser Ile Tyr Gly Val
        435                 440                 445

Ile Gln Gly Tyr Arg Thr Pro Val Leu Ser Ala Glu Ala Ser Thr Gly
450                 455                 460

Glu Thr Pro Asn Leu Gly Glu Val Val Val Ala Glu Val Gly Trp Asp
465                 470                 475                 480

Ala Leu Lys Leu Asn Trp Thr Ala Pro Glu Gly Ala Tyr Glu Tyr Phe
```

```
                485             490             495
Phe Ile Gln Val Gln Glu Ala Asp Thr Val Glu Ala Ala Gln Asn Leu
                500             505             510

Thr Val Pro Gly Gly Leu Arg Ser Thr Asp Leu Pro Gly Leu Lys Ala
            515             520             525

Ala Thr His Tyr Thr Ile Thr Ile Arg Gly Val Thr Gln Asp Phe Ser
        530             535             540

Thr Thr Pro Leu Ser Val Glu Val Leu Thr Glu Glu Val Pro Asp Met
545             550             555             560

Gly Asn Leu Thr Val Thr Glu Val Ser Trp Asp Ala Leu Arg Leu Asn
                565             570             575

Trp Thr Thr Pro Asp Gly Thr Tyr Asp Gln Phe Thr Ile Gln Val Gln
                580             585             590

Glu Ala Asp Gln Val Glu Ala His Asn Leu Thr Val Pro Gly Ser
            595             600             605

Leu Arg Ser Met Glu Ile Pro Gly Leu Arg Ala Gly Thr Pro Tyr Thr
            610             615             620

Val Thr Leu His Gly Glu Val Arg Gly His Ser Thr Arg Pro Leu Ala
625             630             635             640

Val Glu Val Val Thr Glu Asp Leu Pro Gln Leu Gly Asp Leu Ala Val
                645             650             655

Ser Glu Val Gly Trp Asp Gly Leu Arg Leu Asn Trp Thr Ala Ala Asp
            660             665             670

Asn Ala Tyr Glu His Phe Val Ile Gln Val Gln Glu Val Asn Lys Val
            675             680             685

Glu Ala Ala Gln Asn Leu Thr Leu Pro Gly Ser Leu Arg Ala Val Asp
690             695             700

Ile Pro Gly Leu Glu Ala Ala Thr Pro Tyr Arg Val Ser Ile Tyr Gly
705             710             715             720

Val Ile Arg Gly Tyr Arg Thr Pro Val Leu Ser Ala Glu Ala Ser Thr
            725             730             735

Ala Lys Glu Ala Met Gly Ser Pro Lys Glu Val Ile Phe Ser Asp Ile
            740             745             750

Thr Glu Asn Ser Ala Thr Val Ser Trp Arg Ala Pro Thr Ala Gln Val
        755             760             765

Glu Ser Phe Arg Ile Thr Tyr Val Pro Ile Thr Gly Gly Thr Pro Ser
    770             775             780

Met Val Thr Val Asp Gly Thr Lys Thr Gln Thr Arg Leu Val Lys Leu
785             790             795             800

Ile Pro Gly Val Glu Tyr Leu Val Ser Ile Ile Ala Met Lys Gly Phe
            805             810             815

Glu Glu Ser Glu Pro Val Ser Gly Ser Phe Thr Ala Ser Gly Leu
        820             825             830

Asn Asp Ile Phe Glu Ala Gln Lys Ile Glu Trp His Glu Gly Thr His
            835             840             845

His His His His His
        850

<210> SEQ ID NO 11
<211> LENGTH: 400
<212> TYPE: PRT
<213> ORGANISM: Artificial Sequence
<220> FEATURE:
<223> OTHER INFORMATION: Description of Artificial Sequence: Synthetic
      polypeptide
```

<220> FEATURE:
<223> OTHER INFORMATION: huTNC A4 B

<400> SEQUENCE: 11

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
    210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Ile Glu Gly Arg Gly Ser Met Gly Tyr Arg Gly Ser Glu Asp Leu Pro
        275                 280                 285

Gln Leu Gly Asp Leu Ala Val Ser Glu Val Gly Trp Asp Gly Leu Arg
    290                 295                 300

Leu Asn Trp Thr Ala Ala Asp Asn Ala Tyr Glu His Phe Val Ile Gln
305                 310                 315                 320

Val Gln Glu Val Asn Lys Val Glu Ala Ala Gln Asn Leu Thr Leu Pro
                325                 330                 335

Gly Ser Leu Arg Ala Val Asp Ile Pro Gly Leu Glu Ala Ala Thr Pro
            340                 345                 350

Tyr Arg Val Ser Ile Tyr Gly Val Ile Arg Gly Tyr Arg Thr Pro Val
        355                 360                 365

Leu Ser Ala Glu Ala Ser Thr Ala Ser Gly Leu Asn Asp Ile Phe Glu
    370                 375                 380

Ala Gln Lys Ile Glu Trp His Glu Gly Thr His His His His His His
385                 390                 395                 400
```

<210> SEQ ID NO 12
<211> LENGTH: 400
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: huTNC A1 B

<400> SEQUENCE: 12

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Gly Ser Thr Ser
    210                 215                 220

Gly Ser Gly His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Ser Gly
            260                 265                 270

Ile Glu Gly Arg Gly Ser Met Gly Tyr Arg Gly Ser Glu Gln Ala Pro
        275                 280                 285

Glu Leu Glu Asn Leu Thr Val Thr Glu Val Gly Trp Asp Gly Leu Arg
    290                 295                 300

Leu Asn Trp Thr Ala Ala Asp Gln Ala Tyr Glu His Phe Ile Ile Gln
305                 310                 315                 320

Val Gln Glu Ala Asn Lys Val Glu Ala Ala Arg Asn Leu Thr Val Pro
                325                 330                 335

Gly Ser Leu Arg Ala Val Asp Ile Pro Gly Leu Lys Ala Ala Thr Pro
            340                 345                 350

```
Tyr Thr Val Ser Ile Tyr Gly Val Ile Gln Gly Tyr Arg Thr Pro Val
        355                 360                 365

Leu Ser Ala Glu Ala Ser Thr Ala Ser Gly Leu Asn Asp Ile Phe Glu
    370                 375                 380

Ala Gln Lys Ile Glu Trp His Glu Gly Thr His His His His His His
385                 390                 395                 400
```

<210> SEQ ID NO 13
<211> LENGTH: 1614
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: pRJH33 library template DP88-4 library;
      complete Fab coding region comprising PelB leader sequence + Vk1_5
      kappa V-domain + CL constant domain for light chain and PelB +
      VH1_69 V-domain + CH1 constant domain for heavy chain)

<400> SEQUENCE: 13

```
atgaaatacc tattgcctac ggcagccgct ggattgttat tactcgcggc ccagccggcc      60
atggccgaca tccagatgac ccagtctcct tccaccctgt ctgcatctgt aggagaccgt     120
gtcaccatca cttgccgtgc cagtcagagt attagtagct ggttggcctg tatcagcag     180 aaaccaggga agcccctaa gctcctgatc tatgatgcct ccagtttgga aagtggggtc     240
ccatcacgtt tcagcggcag tggatccggg acagaattca ctctcaccat cagcagcttg     300
cagcctgatg attttgcaac ttattactgc aacagtata atagttattc tacgtttggc     360
cagggcacca agtcgagat caagcgtacg gtggctgcac catctgtctt catcttcccg     420
ccatctgatg agcagttgaa atctggaact gcctctgttg tgtgcctgct gaataacttc     480
tatcccagag aggccaaagt acagtggaag gtggataacg ccctccaatc gggtaactcc     540
caggagagtg tcacagagca ggacagcaag gacagcacct acagcctcag cagcaccctg     600
acgctgagca agcagacta cgagaaacac aaagtctacg cctgcgaagt cacccatcag     660
ggcctgagct cgcccgtcac aaagagcttc aacaggggag agtgtggagc cgcagaacaa     720
aaactcatct cagaagagga tctgaatgga gccgcagact acaaggacga cgacgacaag     780
ggtgccgcat aataaggcgc gccaattcta tttcaaggag acagtcatat gaaatacctg     840
ctgccgaccg ctgctgctgg tctgctgctc ctcgctgccc agccggcgat ggcccaggtg     900
caattggtgc agtctggggc tgaggtgaag aagcctgggt cctcggtgaa ggtctcctgc     960
aaggcctccg gaggcacatt cagcagctac gctataagct gggtgcgaca ggcccctgga    1020
caagggctcg agtggatggg agggatcatc cctatctttg gtacagcaaa ctacgcacag    1080
aagttccagg gcagggtcac cattactgca gacaaatcca cgagcacagc ctacatggag    1140
ctgagcagcc tgagatctga ggacaccgcc gtgtattact gtgcgagact atccccaggc    1200
ggttactatg ttatggatgc ctggggccaa gggaccaccg tgaccgtctc ctcagctagc    1260
accaaaggcc catcggtctt cccccctggca ccctcctcca agagcacctc tgggggcaca    1320
gcggccctgg gctgcctggt caaggactac ttccccgaac cggtgacggt gtcgtggaac    1380
tcaggcgccc tgaccagcgg cgtgcacacc ttcccggctg tcctacagtc ctcaggactc    1440
tactccctca gcagcgtggt gaccgtgccc tccagcagct tgggcaccca gacctacatc    1500
tgcaacgtga atcacaagcc cagcaacacc aaggtggaca gaaagttga gcccaaatct    1560 tgtgacgcgg ccgcaagcac tagtgcccat caccatcacc atcacgccgc ggca          1614
```

<210> SEQ ID NO 14
<211> LENGTH: 723
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Fab light chain V1_5

<400> SEQUENCE: 14

```
gacatccaga tgacccagtc tccttccacc ctgtctgcat ctgtaggaga ccgtgtcacc      60
atcacttgcc gtgccagtca gagtattagt agctggttgg cctggtatca gcagaaacca     120
gggaaagccc ctaagctcct gatctatgat gcctccagtt tggaaagtgg ggtcccatca     180
cgtttcagcg gcagtggatc cgggacagaa ttcactctca ccatcagcag cttgcagcct     240
gatgattttg caacttatta ctgccaacag tataatagtt attctacgtt tggccagggc     300
accaaagtcg agatcaagcg tacggtggct gcaccatctg tcttcatctt cccgccatct     360
gatgagcagt tgaaatctgg aactgcctct gttgtgtgcc tgctgaataa cttctatccc     420
agagaggcca aagtacagtg gaaggtggat aacgccctcc aatcgggtaa ctcccaggag     480
agtgtcacag agcaggacag caaggacagc acctacagcc tcagcagcac cctgacgctg     540
agcaaagcag actacgagaa acacaaagtc tacgcctgcg aagtcaccca tcagggcctg     600
agctcgcccg tcacaaagag cttcaacagg ggagagtgtg agccgcagac aaaaaactc     660
atctcagaag aggatctgaa tggagccgca gactacaagg acgacgacga caagggtgcc     720
gca                                                                    723
```

<210> SEQ ID NO 15
<211> LENGTH: 720
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Fab heavy chain VH1_69

<400> SEQUENCE: 15

```
caggtgcaat tggtgcagtc tggggctgag gtgaagaagc ctgggtcctc ggtgaaggtc      60
tcctgcaagg cctccggagg cacattcagc agctacgcta taagctgggt gcgacaggcc     120
cctggacaag gctcgagtg gatgggaggg atcatcccta tctttggtac agcaaactac     180
gcacagaagt tccagggcag ggtcaccatt actgcagaca aatccacgag cacagcctac     240
atggagctga gcagcctgag atctgaggac accgccgtgt attactgtgc gagactatcc     300
ccaggcggtt actatgttat ggatgcctgg ggccaaggga ccaccgtgac cgtctcctca     360
gctagcacca aaggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaaag tggacaagaa agttgagccc     660
aaatcttgtg acgcggccgc aagcactagt gcccatcacc atcaccatca cgccgcggca     720
```

<210> SEQ ID NO 16

<211> LENGTH: 241
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Fab light chain Vk1_5

<400> SEQUENCE: 16

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Gly Ala Ala Glu Gln Lys Leu Ile Ser Glu Glu
    210                 215                 220

Asp Leu Asn Gly Ala Ala Asp Tyr Lys Asp Asp Asp Lys Gly Ala
225                 230                 235                 240

Ala

<210> SEQ ID NO 17
<211> LENGTH: 240
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Fab heavy chain VH1_69 (DP88)

<400> SEQUENCE: 17

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

```
Gly Ile Ile Pro Ile Phe Gly Thr Ala Asn Tyr Ala Gln Lys Phe
 50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Leu Ser Pro Gly Gly Tyr Tyr Val Met Asp Ala Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Ala Ala Ala Ser Thr Ser Ala His His His His His His Ala Ala Ala
225                 230                 235                 240

<210> SEQ ID NO 18
<211> LENGTH: 1605
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: pRJH53 library template of lambda-DP47 library
      Vl3_19/VH3_23

<400> SEQUENCE: 18
atgaaatacc tattgcctac ggcagccgct ggattgttat tactcgcggc ccagccggcc      60
atggcctcgt ctgagctgac tcaggaccct gctgtgtctg tggccttggg acagacagtc     120
aggatcacat gccaaggaga cagcctcaga agttattatg caagctggta ccagcagaag     180
ccaggacagg cccctgtact tgtcatctat ggtaaaaaca accggccctc agggatccca     240
gaccgattct ctggctccag ctcaggaaac acagcttcct tgaccatcac tggggctcag     300
gcggaagatg aggctgacta ttactgtaac tcccgtgata gtagcggtaa tcatgtggta     360
ttcggcggag ggaccaagct gaccgtccta ggacaaccca aggctgcccc cagcgtgacc     420
ctgttccccc cagcagcga ggaattgcag gccaacaagg ccaccctggt ctgcctgatc     480
agcgacttct acccaggcgc cgtgaccgtg gcctggaagg ccgacagcag ccccgtgaag     540
gccggcgtgg agaccaccac ccccagcaag cagagcaaca caagtacgc cgccagcagc     600 tacctgagcc tgaccccga gcagtggaag agccacaggt cctacagctg ccaggtgacc     660
cacgagggca gcaccgtgga aaaaccgtg gcccccaccg agtgcagcgg agccgcagaa     720
caaaaactca tctcagaaga ggatctgaat ggagccgcag actacaagga cgacgacgac     780
aagggtgccg cataataagg cgcgccaatt ctatttcaag agacagtca tatgaaatac     840
```

```
ctgctgccga ccgctgctgc tggtctgctg ctcctcgctg cccagccggc gatggccgag    900
gtgcaattgc tggagtctgg gggaggcttg gtacagcctg gggggtccct gagactctcc    960
tgtgcagcct ccggattcac ctttagcagt tatgccatga gctgggtccg ccaggctcca   1020
gggaaggggc tggagtgggt ctcagctatt agtggtagtg gtggtagcac atactacgca   1080
gactccgtga agggccggtt caccatctcc agagacaatt ccaagaacac gctgtatctg   1140
cagatgaaca gcctgagagc cgaggacacg gccgtatatt actgtgcgaa accgtttccg   1200
tattttgact actggggcca aggaaccctg gtcaccgtct cgagtgctag caccaaaggc   1260
ccatcggtct tccccctggc accctcctcc aagagcacct ctgggggcac agcggccctg   1320
ggctgcctgg tcaaggacta cttccccgaa ccggtgacgg tgtcgtggaa ctcaggcgcc   1380
ctgaccagcg gcgtgcacac cttcccggct gtcctacagt cctcaggact ctactccctc   1440
agcagcgtgg tgaccgtgcc ctccagcagc ttgggcaccc agacctacat ctgcaacgtg   1500
aatcacaagc ccagcaacac caaagtggac aagaaagttg agcccaaatc ttgtgacgcg   1560
gccgcaagca ctagtgccca tcaccatcac catcacgccg cggca                  1605

<210> SEQ ID NO 19
<211> LENGTH: 726
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Fab light chain Vl3_19

<400> SEQUENCE: 19
tcgtctgagc tgactcagga ccctgctgtg tctgtggcct tgggacagac agtcaggatc     60
acatgccaag agacagcct cagaagttat tatgcaagct ggtaccagca gaagccagga    120
caggcccctg tacttgtcat ctatggtaaa aacaaccggc cctcagggat cccagaccga    180
ttctctggct ccagctcagg aaacacagct tccttgacca tcactggggc tcaggcggaa    240
gatgaggctg actattactg taactcccgt gatagtagcg gtaatcatgt ggtattcggc    300
ggagggacca agctgaccgt cctaggacaa cccaaggctg cccccagcgt gaccctgttc    360
ccccccagca gcgaggaatt gcaggccaac aaggccaccc tggtctgcct gatcagcgac    420
ttctacccag gcgccgtgac cgtggcctgg aaggccgaca gcagccccgt gaaggccggc    480
gtggagacca ccacccccag caagcagagc aacaacaagt acgccgccag cagctacctg    540
agcctgaccc ccgagcagtg gaagagccac aggtcctaca gctgccaggt gacccacgag    600
ggcagcaccg tggagaaaac cgtggccccc accgagtgca gcggagccgc agaacaaaaa    660
ctcatctcag aagaggatct gaatggagcc gcagactaca aggacgacga cgacaagggt    720
gccgca                                                              726

<210> SEQ ID NO 20
<211> LENGTH: 708
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Fab heavy chain VH3_23

<400> SEQUENCE: 20
gaggtgcaat tgctggagtc tgggggaggc ttggtacagc ctggggggtc cctgagactc     60
```

-continued

```
tcctgtgcag cctccggatt cacctttagc agttatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcagatga acagcctgag agccgaggac acggccgtat attactgtgc gaaaccgttt    300
ccgtattttg actactgggg ccaaggaacc ctggtcaccg tctcgagtgc tagcaccaaa    360
ggcccatcgg tcttccccct ggcacccctcc tccaagagca cctctggggg cacagcggcc    420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tggtgaccgt gccctccagc agcttgggca cccagaccta catctgcaac    600
gtgaatcaca agcccagcaa caccaaagtg gacaagaaag ttgagcccaa atcttgtgac    660
gcggccgcaa gcactagtgc ccatcaccat caccatcacg ccgcggca                 708
```

<210> SEQ ID NO 21
<211> LENGTH: 242
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Fab light chain Vl3_19

<400> SEQUENCE: 21

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser Gly Ala Ala Glu Gln Lys Leu Ile Ser Glu
    210                 215                 220

Glu Asp Leu Asn Gly Ala Ala Asp Tyr Lys Asp Asp Asp Asp Lys Gly

<210> SEQ ID NO 22
<211> LENGTH: 236
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Fab heavy chain VH3_23 (DP47)

<400> SEQUENCE: 22

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Pro Phe Pro Tyr Phe Asp Tyr Trp Gly Gln Gly Thr Leu Val
            100                 105                 110
Thr Val Ser Ser Ala Ser Thr Lys Gly Pro Ser Val Phe Pro Leu Ala
        115                 120                 125
Pro Ser Ser Lys Ser Thr Ser Gly Gly Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
        195                 200                 205
Lys Val Asp Lys Lys Val Glu Pro Lys Ser Cys Asp Ala Ala Ala Ser
    210                 215                 220
Thr Ser Ala His His His His His Ala Ala Ala
225                 230                 235
```

<210> SEQ ID NO 23
<211> LENGTH: 324
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 18D4 VL

<400> SEQUENCE: 23

```
gacatccaga tgacccagtc tccatccacc ctgtctgcat ctgtaggaga ccgtgtcacc      60
atcacttgcc gtgccagtca gagtattagt agctggttgg cctggtatca gcagaaacca     120
```

```
gggaaagccc ctaagctcct gatctatgat gcctccagtt tggaaagtgg ggtcccatca    180
cgtttcagcg gcagtggatc cgggacagaa ttcactctca ccatcagcag cttgcagcct    240
gatgattttg caacttatta ctgccaacag aataagaagt ttccttcggg gacgtttggc    300
cagggcacca aagtcgagat caag                                           324
```

<210> SEQ ID NO 24
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 18D4 VH

<400> SEQUENCE: 24

```
caggtgcaat tggtgcagtc tggggctgag gtgaagaagc ctgggtcctc ggtgaaggtc    60
tcctgcaagg cctccggagg cacattcagc agctacgcta taagctgggt gcgacaggcc   120
cctggacaag ggctcgagtg gatgggaggg atcatcccta tctttggtac agcaaactac   180
gcacagaagt tccagggcag ggtcaccatt actgcagaca aatccacgag cacagcctac   240
atggagctga gcagcctgag atctgaggac accgccgtgt attactgtgc gaaaggtaac   300
ttctacggtg gtctggacta ctggggccaa gggaccaccg tgaccgtctc ctca         354
```

<210> SEQ ID NO 25
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 11C7 VL

<400> SEQUENCE: 25

```
tcgtctgagc tgactcagga ccctgctgtg tctgtggcct tgggacagac agtcagggtc    60
acatgccaag agacagcct cagaagttat tatgcaagct ggtaccagca gaagccagga   120
caggcccctg tacttgtcat ctatggtaaa acaaccggc cctcagggat cccagaccga    180
ttctctggct ccagctcagg aaacacagct tccttgacca tcactgggc tcaggcggaa    240 gatgaggctg actattactg taactccatt aatagtactc gtaatgaggt attcggcgga    300
gggaccaagc tgaccgtcct a                                              321
```

<210> SEQ ID NO 26
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 11C7 VH

<400> SEQUENCE: 26

```
gaggtgcaat tgttggagtc tgggggaggc ttggtacagc ctgggggtc cctgagactc    60 tcctgtgcag cctccggatt cacctttagc agttatgcca tgagctgggt ccgccaggct   120
ccagggaagg ggctggagtg ggtctcagct attagcggta gtggtggtag cacatactac   180
gcagactccg tgaagggccg gttcaccatc tccaaagaca attccaagaa cacgctgtat   240
```

```
ctgcagatga acagcctgag agccgaggac acggccgtat attactgtgc gaaaacttct    300
ccgcgtgttc cgctggacta ctggggccaa ggaaccctgg tcaccgtctc gagt          354
```

<210> SEQ ID NO 27
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 18D4 VL

<400> SEQUENCE: 27

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Asn Lys Lys Phe Pro Ser
                85                  90                  95

Gly Thr Phe Gly Gln Gly Thr Lys Val Glu Ile Lys
            100                 105
```

<210> SEQ ID NO 28
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 18D4 VH

<400> SEQUENCE: 28

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Gly Asn Phe Tyr Gly Gly Leu Asp Tyr Trp Gly Gln Gly Thr
            100                 105                 110

Thr Val Thr Val Ser Ser
        115
```

<210> SEQ ID NO 29
<211> LENGTH: 107
<212> TYPE: PRT

```
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 11C7 VL

<400> SEQUENCE: 29

Ser Ser Glu Leu Thr Gln Asp Pro Ala Val Ser Val Ala Leu Gly Gln
1               5                   10                  15

Thr Val Arg Val Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ile Asn Ser Thr Arg Asn Glu
                85                  90                  95

Val Phe Gly Gly Gly Thr Lys Leu Thr Val Leu
            100                 105

<210> SEQ ID NO 30
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 11C7 VH

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Lys Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Ser Pro Arg Val Pro Leu Asp Tyr Trp Gly Gln Gly Thr
            100                 105                 110

Leu Val Thr Val Ser Ser
        115

<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 18D4 LCDR1

<400> SEQUENCE: 31
```
cgtgccagtc agagtattag tagctggttg gcc                                    33

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 18D4 LCDR2

<400> SEQUENCE: 32
gatgcctcca gtttggaaag t                                                21

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 18D4 LCDR3

<400> SEQUENCE: 33
caacagaata agaagtttcc ttcggggacg                                       30

<210> SEQ ID NO 34
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 11C7 LCDR1

<400> SEQUENCE: 34
caaggagaca gcctcagaag ttattatgca agc                                   33

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 11C7 LCDR2

<400> SEQUENCE: 35
ggtaaaaaca accggccctc a                                                21

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 11C7 LCDR3

<400> SEQUENCE: 36
aactccatta atagtactcg taatgaggta                                       30

```
<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 18D4 LCDR1

<400> SEQUENCE: 37

Arg Ala Ser Gln Ser Ile Ser Ser Trp Leu Ala
1               5                   10

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 18D4 LCDR2

<400> SEQUENCE: 38

Asp Ala Ser Ser Leu Glu Ser
1               5

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 18D4 LCDR3

<400> SEQUENCE: 39

Gln Gln Asn Lys Lys Phe Pro Ser Gly Thr
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 11C7 LCDR1

<400> SEQUENCE: 40

Gln Gly Asp Ser Leu Arg Ser Tyr Tyr Ala Ser
1               5                   10

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 11C7 LCDR2

<400> SEQUENCE: 41

Gly Lys Asn Asn Arg Pro Ser
1               5
```

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 11C7 LCDR3

<400> SEQUENCE: 42

Asn Ser Ile Asn Ser Thr Arg Asn Glu Val
1               5                   10

<210> SEQ ID NO 43
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 18D4 HCDR1

<400> SEQUENCE: 43
agctacgcta taagc                                                15

<210> SEQ ID NO 44
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 18D4 HCDR2

<400> SEQUENCE: 44
gggatcatcc ctatctttgg tacagcaaac tacgcacaga gttccaggg c          51

<210> SEQ ID NO 45
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 18D4 HCDR3

<400> SEQUENCE: 45
ggtaacttct acggtggtct ggactac                                    27

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 11C7 HCDR1

<400> SEQUENCE: 46
ggattcacct ttagcagtta tgccatgagc                                 30

<210> SEQ ID NO 47
<211> LENGTH: 51

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 11C7 HCDR2

<400> SEQUENCE: 47
gctattagcg gtagtggtgg tagcacatac tacgcagact ccgtgaaggg c           51

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 11C7 HCDR3

<400> SEQUENCE: 48
acttctccgc gtgttccgct ggactac                                      27

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 18D4 HCDR1

<400> SEQUENCE: 49

Ser Tyr Ala Ile Ser
1               5

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 18D4 HCDR2

<400> SEQUENCE: 50

Gly Ile Ile Pro Ile Phe Gly Thr Ala Asn Tyr Ala Gln Lys Phe Gln
1               5                   10                  15

Gly

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 18D4 HCDR3

<400> SEQUENCE: 51

Gly Asn Phe Tyr Gly Gly Leu Asp Tyr
1               5

<210> SEQ ID NO 52
```

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 11C7 HCDR1

<400> SEQUENCE: 52

Gly Phe Thr Phe Ser Ser Tyr Ala Met Ser
1               5                   10

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 11C7 HCDR2

<400> SEQUENCE: 53

Ala Ile Ser Gly Ser Gly Gly Ser Thr Tyr Tyr Ala Asp Ser Val Lys
1               5                   10                  15

Gly

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 11C7 HCDR3

<400> SEQUENCE: 54

Thr Ser Pro Arg Val Pro Leu Asp Tyr
1               5

<210> SEQ ID NO 55
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 18D4 Light chain

<400> SEQUENCE: 55
gacatccaga tgacccagtc tccatccacc ctgtctgcat ctgtaggaga ccgtgtcacc        60
atcacttgcc gtgccagtca gagtattagt agctggttgg cctggtatca gcagaaacca       120
gggaaagccc ctaagctcct gatctatgat gcctccagtt tggaaagtgg ggtcccatca       180
cgtttcagcg gcagtggatc cgggacagaa ttcactctca ccatcagcag cttgcagcct       240
gatgattttg caacttatta ctgccaacag aataagaagt ttccttcggg acgtttggc        300 cagggcacca aagtcgagat caagcgtacg gtggctgcac catctgtctt catcttcccg       360
ccatctgatg agcagttgaa atctggaact gcctctgttg tgtgcctgct gaataacttc       420
tatcccagag aggccaaagt acagtggaag gtggataacg ccctccaatc gggtaactcc       480
caggagagtg tcacagagca ggacagcaag gacagcacct acagcctcag cagcacccty       540

```
acgctgagca aagcagacta cgagaaacac aaagtctacg cctgcgaagt cacccatcag      600
ggcctgagct cgcccgtcac aaagagcttc aacaggggag agtgt                      645
```

<210> SEQ ID NO 56
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 18D4 Heavy chain

<400> SEQUENCE: 56

```
caggtgcaat tggtgcagtc tggggctgag gtgaagaagc ctgggtcctc ggtgaaggtc        60
tcctgcaagg cctccggagg cacattcagc agctacgcta taagctgggt gcgacaggcc      120
cctggacaag ggctcgagtg gatgggaggg atcatcccta tctttggtac agcaaactac      180
gcacagaagt tccagggcag ggtcaccatt actgcagaca atccacgag cacagcctac       240 atggagctga gcagcctgag atctgaggac accgccgtgt attactgtgc gaaaggtaac      300
ttctacggtg tctggacta ctggggccaa gggaccaccg tgaccgtctc ctcagctagc       360
accaagggcc catcggtctt ccccctggca ccctcctcca gagcacctc tgggggcaca       420 gcggccctgg gctgcctggt caaggactac ttccccgaac cggtgacggt gtcgtggaac      480
tcaggcgccc tgaccagcgg cgtgcacacc ttcccggctg tcctacagtc ctcaggactc      540
tactccctca gcagcgtggt gaccgtgccc tccagcagct gggcaccca gacctacatc       600 tgcaacgtga atcacaagcc cagcaacacc aaggtggaca gaaagttga gcccaaatct      660 tgtgacaaaa ctcacacatg cccaccgtgc ccagcacctg aactcctggg gggaccgtca     720
gtcttcctct tccccccaaa acccaaggac accctcatga tctcccggac ccctgaggtc      780
acatgcgtgg tggtggacgt gagccacgaa gaccctgagg tcaagttcaa ctggtacgtg      840
gacggcgtgg aggtgcataa tgccaagaca aagccgcggg aggagcagta caacagcacg      900
taccgtgtgg tcagcgtcct caccgtcctg caccaggact ggctgaatgg caaggagtac     960
aagtgcaagg tctccaacaa agccctccca gcccccatcg agaaaccat ctccaaagcc     1020 aaagggcagc cccgagaacc acaggtgtac accctgcccc catcccggga tgagctgacc     1080
aagaaccagg tcagcctgac ctgcctggtc aaaggcttct atcccagcga catcgccgtg     1140
gagtgggaga gcaatgggca gccggagaac aactacaaga ccacgcctcc cgtgctggac     1200
tccgacggct ccttcttcct ctacagcaag ctcaccgtgg acaagagcag gtggcagcag     1260
gggaacgtct tctcatgctc cgtgatgcat gaggctctgc acaaccacta cacgcagaag     1320
agcctctccc tgtctccggg taaa                                            1344
```

<210> SEQ ID NO 57
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 11C7 Light chain

<400> SEQUENCE: 57

```
tcgtctgagc tgactcagga ccctgctgtg tctgtggcct gggacagac agtcagggtc        60 acatgccaag agacagcct cagaagttat tatgcaagct ggtaccagca gaagccagga      120
```

```
caggccnctg tacttgtcat ctatggtaaa acaaccggc cctcagggat cccagaccga      180
ttctctggct ccagctcagg aaacacagct tccttgacca tcactggggc tcaggcggaa      240
gatgaggctg actattactg taactccatt aatagtactc gtaatgaggt attcggcgga      300
gggaccaagc tgaccgtcct aggtcaaccc aaggctgccc ccagcgtgac cctgttcccc      360
cccagcagcg aggaactgca ggccaacaag gccaccctgg tctgcctgat cagcgacttc      420
tacccaggcg ccgtgaccgt ggcctggaag gccgacagca gccccgtgaa ggccggcgtg      480
gagaccacca cccccagcaa gcagagcaac aacaagtacg ccgccagcag ctacctgagc      540
ctgacccccg agcagtggaa gagccacagg tcctacagct gccaggtgac ccacgagggc      600
agcaccgtgg agaaaaccgt ggccccace gagtgcagc                              639
```

<210> SEQ ID NO 58
<211> LENGTH: 1344
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 11C7 Heavy chain

<400> SEQUENCE: 58

```
gaggtgcaat tgttggagtc tgggggaggc ttggtacagc ctgggggtc cctgagactc       60 tcctgtgcag cctccggatt caccttagc agttatgcca tgagctgggt ccgccaggct      120
ccagggaagg ggctggagtg gtctcagct attagcggta gtggtggtag cacatactac      180
gcagactccg tgaagggccg gttcaccatc tccaaagaca attccaagaa cacgctgtat      240
ctgcagatga acagcctgag agccgaggac acggccgtat attactgtgc gaaaacttct      300
ccgcgtgttc cgctggacta ctggggccaa ggaaccctgg tcaccgtctc gagtgctagc      360
accaagggcc catcggtctt ccccctggca ccctcctcca agagcacctc tgggggcaca      420
gcggccctgg gctgcctggt caaggactac ttccccgaac cggtgacggt gtcgtggaac      480
tcaggcgccc tgaccagcgg cgtgcacacc ttcccggctg tcctacagtc ctcaggactc      540
tactccctca gcagcgtggt gaccgtgccc tccagcagct gggcaccca gacctacatc      600 tgcaacgtga atcacaagcc cagcaacacc aaggtggaca gaaagttga gcccaaatct      660 tgtgacaaaa ctcacacatg cccaccgtgc ccagcacctg aactcctggg gggaccgtca      720
gtcttcctct tccccccaaa acccaaggac accctcatga tctcccggac ccctgaggtc      780
acatgcgtgg tggtggacgt gagccacgaa gaccctgagg tcaagttcaa ctggtacgtg      840
gacggcgtgg aggtgcataa tgccaagaca aagccgcggg aggagcagta caacagcacg      900
taccgtgtgg tcagcgtcct caccgtcctg caccaggact ggctgaatgg caaggagtac      960
aagtgcaagg tctccaacaa agccctccca gcccccatcg agaaaaccat ctccaaagcc     1020
aaagggcagc ccgagaacc acaggtgtac accctgcccc catcccggga tgagctgacc     1080
aagaaccagg tcagcctgac ctgcctggtc aaaggcttct atcccagcga catcgccgtg     1140
gagtgggaga gcaatgggca gccggagaac aactacaaga ccacgcctcc cgtgctggac     1200
tccgacggct ccttcttcct ctacagcaag ctcaccgtgg acaagagcag gtggcagcag     1260
gggaacgtct tctcatgctc cgtgatgcat gaggctctgc acaaccacta cacgcagaag     1320
agcctctccc tgtctccggg taaa                                           1344
```

```
<210> SEQ ID NO 59
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 18D4 Light chain

<400> SEQUENCE: 59

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Asn Lys Lys Phe Pro Ser
                85                  90                  95

Gly Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 60
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 18D4 Heavy chain

<400> SEQUENCE: 60

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60
```

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Gly Asn Phe Tyr Gly Gly Leu Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 61
<211> LENGTH: 213
<212> TYPE: PRT
<213> ORGANISM: Artificial Sequence
<220> FEATURE:
<223> OTHER INFORMATION: Description of Artificial Sequence: Synthetic -continued polypeptide
<220> FEATURE:
<223> OTHER INFORMATION: 11C7 Light chain

<400> SEQUENCE: 61

Ser Ser Glu Leu Thr Gln Asp Pro Ala Val Ser Val Ala Leu Gly Gln
1               5                   10                  15

Thr Val Arg Val Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ile Asn Ser Thr Arg Asn Glu
                85                  90                  95

Val Phe Gly Gly Gly Thr Lys Leu Thr Val Leu Gly Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 62
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 11C7 Heavy chain

<400> SEQUENCE: 62

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Lys Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Ser Pro Arg Val Pro Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 63
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 18D4 Heavy chain PGLALA

<400> SEQUENCE: 63

```
caggtgcaat tggtgcagtc tggggctgag gtgaagaagc ctgggtcctc ggtgaaggtc       60
tcctgcaagg cctccggagg cacattcagc agctacgcta taagctgggt gcgacaggcc      120
cctggacaag ggctcgagtg gatgggaggg atcatccta tctttggtac agcaaactac       180
gcacagaagt tccagggcag ggtcaccatt actgcagaca atccacgag acagcctac         240
atggagctga gcagcctgag atctgaggac accgccgtgt attactgtgc gaaaggtaac      300
ttctacggtg gtctggacta ctggggccaa gggaccaccg tgaccgtctc ctcagctagc      360
accaagggcc catcggtctt ccccctggca ccctcctcca gagcacctc tgggggcaca       420
gcggccctgg gctgcctggt caaggactac ttccccgaac cggtgacggt gtcgtggaac      480
tcaggcgccc tgaccagcgg cgtgcacacc ttcccggctg tcctacagtc ctcaggactc      540
tactccctca gcagcgtggt gaccgtgccc tccagcagct gggcaccca gacctacatc       600
tgcaacgtga atcacaagcc cagcaacacc aaggtggaca agaaagttga gcccaaatct      660
tgtgacaaaa ctcacacatg cccaccgtgc ccagcacctg aagctgcagg ggaccgtca       720
gtcttcctct tccccccaaa acccaaggac accctcatga tctcccggac ccctgaggtc      780
acatgcgtgg tggtggacgt gagccacgaa gaccctgagg tcaagttcaa ctggtacgtg      840
gacggcgtgg aggtgcataa tgccaagaca agccgcggg aggagcagta caacagcacg       900
taccgtgtgg tcagcgtcct caccgtcctg caccaggact ggctgaatgg caaggagtac      960
aagtgcaagg tctccaacaa agccctcggc gcccccatcg agaaaccat ctccaaagcc      1020
aaagggcagc cccgagaacc acaggtgtac accctgcccc catcccggga tgagctgacc     1080
aagaaccagg tcagcctgac ctgcctggtc aaaggcttct atcccagcga catcgccgtg     1140
gagtgggaga gcaatgggca gccggagaac aactacaaga ccacgcctcc cgtgctggac     1200
tccgacggct ccttcttcct ctacagcaag ctcaccgtgg acaagagcag gtggcagcag     1260
gggaacgtct tctcatgctc cgtgatgcat gaggctctgc acaaccacta cacgcagaag     1320
agcctctccc tgtctccggg taaa                                             1344
```

<210> SEQ ID NO 64
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 11C7 Heavy chain PGLALA

<400> SEQUENCE: 64

```
gaggtgcaat tgttggagtc tgggggaggc ttggtacagc ctgggggtc cctgagactc        60
tcctgtgcag cctccggatt cacctttagc agttatgcca tgagctgggt ccgccaggct      120
ccagggaagg ggctggagtg ggtctcagct attagcggta gtggtggtag cacatactac      180
gcagactccg tgaagggccg gttcaccatc tccaaagaca attccaagaa cacgctgtat      240
ctgcagatga acagcctgag agccgaggac acggccgtat attactgtgc gaaaacttct     300
ccgcgtgttc cgctggacta ctggggccaa ggaaccctgg tcaccgtctc gagtgctagc      360
accaagggcc catcggtctt ccccctggca ccctcctcca gagcacctc tgggggcaca       420
gcggccctgg gctgcctggt caaggactac ttccccgaac cggtgacggt gtcgtggaac      480
tcaggcgccc tgaccagcgg cgtgcacacc ttcccggctg tcctacagtc ctcaggactc      540
tactccctca gcagcgtggt gaccgtgccc tccagcagct gggcaccca gacctacatc       600
```

-continued

```
tgcaacgtga atcacaagcc cagcaacacc aaggtggaca agaaagttga gcccaaatct      660
tgtgacaaaa ctcacacatg cccaccgtgc ccagcacctg aagctgcagg gggaccgtca      720
gtcttcctct tccccccaaa acccaaggac accctcatga tctcccggac ccctgaggtc      780
acatgcgtgg tggtggacgt gagccacgaa gaccctgagg tcaagttcaa ctggtacgtg      840
gacggcgtgg aggtgcataa tgccaagaca aagccgcggg aggagcagta caacagcacg      900
taccgtgtgg tcagcgtcct caccgtcctg caccaggact ggctgaatgg caaggagtac      960
aagtgcaagg tctccaacaa agccctcggc gccccatcg agaaaaccat ctccaaagcc       1020
aaagggcagc cccgagaacc acaggtgtac accctgcccc catcccggga tgagctgacc      1080
aagaaccagg tcagcctgac ctgcctggtc aaaggcttct atcccagcga catcgccgtg      1140
gagtgggaga gcaatgggca gccggagaac aactacaaga ccacgcctcc cgtgctggac      1200
tccgacggct ccttcttcct ctacagcaag ctcaccgtgg acaagagcag gtggcagcag      1260
gggaacgtct tctcatgctc cgtgatgcat gaggctctgc acaaccacta cacgcagaag      1320
agcctctccc tgtctccggg taaa                                              1344
```

<210> SEQ ID NO 65
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 18D4 Heavy chain PGLALA

<400> SEQUENCE: 65

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Gly Asn Phe Tyr Gly Gly Leu Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
```

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 66
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 11C7 Heavy chain PGLALA

<400> SEQUENCE: 66

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Lys Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Ser Pro Arg Val Pro Leu Asp Tyr Trp Gly Gln Gly Thr
            100                 105                 110

Leu Val Thr Val Ser Ser Ala Ser Thr Lys Gly Pro Ser Val Phe Pro

|     |     |     |     | 115 |     |     |     |     | 120 |     |     |     |     | 125 |     |
| --- | --- | --- | --- | --- | --- | --- | --- | --- | --- | --- | --- | --- | --- | --- | --- |

Leu Ala Pro Ser Ser Lys Ser Thr Ser Gly Gly Thr Ala Ala Leu Gly
       130                135                140

Cys Leu Val Lys Asp Tyr Phe Pro Glu Pro Val Thr Val Ser Trp Asn
145                150                155              160

Ser Gly Ala Leu Thr Ser Gly Val His Thr Phe Pro Ala Val Leu Gln
       165                170                175

Ser Ser Gly Leu Tyr Ser Leu Ser Ser Val Val Thr Val Pro Ser Ser
       180                185                190

Ser Leu Gly Thr Gln Thr Tyr Ile Cys Asn Val Asn His Lys Pro Ser
       195                200                205

Asn Thr Lys Val Asp Lys Lys Val Glu Pro Lys Ser Cys Asp Lys Thr
       210                215                220

His Thr Cys Pro Pro Cys Pro Ala Pro Glu Ala Ala Gly Gly Pro Ser
225                230                235              240

Val Phe Leu Phe Pro Pro Lys Pro Lys Asp Thr Leu Met Ile Ser Arg
       245                250                255

Thr Pro Glu Val Thr Cys Val Val Val Asp Val Ser His Glu Asp Pro
       260                265                270

Glu Val Lys Phe Asn Trp Tyr Val Asp Gly Val Glu Val His Asn Ala
       275                280                285

Lys Thr Lys Pro Arg Glu Glu Gln Tyr Asn Ser Thr Tyr Arg Val Val
       290                295                300

Ser Val Leu Thr Val Leu His Gln Asp Trp Leu Asn Gly Lys Glu Tyr
305                310                315              320

Lys Cys Lys Val Ser Asn Lys Ala Leu Gly Ala Pro Ile Glu Lys Thr
       325                330                335

Ile Ser Lys Ala Lys Gly Gln Pro Arg Glu Pro Gln Val Tyr Thr Leu
       340                345                350

Pro Pro Ser Arg Asp Glu Leu Thr Lys Asn Gln Val Ser Leu Thr Cys
       355                360                365

Leu Val Lys Gly Phe Tyr Pro Ser Asp Ile Ala Val Glu Trp Glu Ser
370                375                380

Asn Gly Gln Pro Glu Asn Asn Tyr Lys Thr Thr Pro Pro Val Leu Asp
385                390                395              400

Ser Asp Gly Ser Phe Phe Leu Tyr Ser Lys Leu Thr Val Asp Lys Ser
       405                410                415

Arg Trp Gln Gln Gly Asn Val Phe Ser Cys Ser Val Met His Glu Ala
       420                425                430

Leu His Asn His Tyr Thr Gln Lys Ser Leu Ser Leu Ser Pro Gly Lys
       435                440                445

```
<210> SEQ ID NO 67
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Leader Sequence 1

<400> SEQUENCE: 67
```

Met Asp Trp Thr Trp Arg Ile Leu Phe Leu Val Ala Ala Ala Thr Gly
1              5                10              15

Ala His Ser

<210> SEQ ID NO 68
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Leader Sequence 1 (DNA1)

<400> SEQUENCE: 68
atggactgga cctggagaat cctcttcttg gtggcagcag ccacaggagc ccactcc      57

<210> SEQ ID NO 69
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Leader Sequence 1 (DNA 2)

<400> SEQUENCE: 69
atggactgga cctggaggat cctcttcttg gtggcagcag ccacaggagc ccactcc      57

<210> SEQ ID NO 70
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Leader Sequence 2

<400> SEQUENCE: 70

Met Asp Met Arg Val Pro Ala Gln Leu Leu Gly Leu Leu Leu Leu Trp
1               5                   10                  15

Phe Pro Gly Ala
            20

<210> SEQ ID NO 71
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Leader Sequence 2 (DNA)

<400> SEQUENCE: 71
atggacatga gggtccccgc tcagctcctg ggcctcctgc tgctctggtt cccaggtgcc      60
aggtgt                                                                66

<210> SEQ ID NO 72
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Leader Sequence 3

<400> SEQUENCE: 72

Met Gly Trp Ser Cys Ile Ile Leu Phe Leu Val Ala Thr Ala Thr Gly
1               5                   10                  15

Val His Ser

<210> SEQ ID NO 73
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Leader Sequence 3 (DNA 1)

<400> SEQUENCE: 73
atgggatgga gctgtatcat cctcttcttg gtagcaacag ctaccggtgt gcattcg      57

<210> SEQ ID NO 74
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Leader Sequence 3 (DNA 2)

<400> SEQUENCE: 74
atgggctggt cctgcatcat cctgtttctg gtggctaccg ccactggagt gcattcc      57

<210> SEQ ID NO 75
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Leader Sequence 3 (DNA 3)

<400> SEQUENCE: 75
atgggctggt cctgcatcat cctgtttctg gtcgccacag ccaccggcgt gcactct      57

<210> SEQ ID NO 76
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: LMB3

<400> SEQUENCE: 76
caggaaacag ctatgaccat gattac                                        26

<210> SEQ ID NO 77
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Vk1_5_L3r_S
<220> FEATURE:
<221> NAME/KEY: misc_feature
<222> LOCATION: (28)..(28)

```
<223> OTHER INFORMATION: 60% given sequence and 40% m
<220> FEATURE:
<221> NAME/KEY: misc_feature
<222> LOCATION: (29)..(30)
<223> OTHER INFORMATION: 60% given sequence and 40% n
<220> FEATURE:
<221> NAME/KEY: misc_feature
<222> LOCATION: (31)..(31)
<223> OTHER INFORMATION: 60% given sequence and 40% m
<220> FEATURE:
<221> NAME/KEY: misc_feature
<222> LOCATION: (32)..(33)
<223> OTHER INFORMATION: 60% given sequence and 40% n
<220> FEATURE:
<221> NAME/KEY: misc_feature
<222> LOCATION: (34)..(34)
<223> OTHER INFORMATION: 60% given sequence and 40% m
<220> FEATURE:
<221> NAME/KEY: misc_feature
<222> LOCATION: (35)..(36)
<223> OTHER INFORMATION: 60% given sequence and 40% n
<220> FEATURE:
<221> NAME/KEY: misc_feature
<222> LOCATION: (37)..(37)
<223> OTHER INFORMATION: 60% given sequence and 40% m
<220> FEATURE:
<221> NAME/KEY: misc_feature
<222> LOCATION: (38)..(39)
<223> OTHER INFORMATION: 60% given sequence and 40% n
<220> FEATURE:
<221> NAME/KEY: misc_feature
<222> LOCATION: (40)..(40)
<223> OTHER INFORMATION: 60% given sequence and 40% m
<220> FEATURE:
<221> NAME/KEY: misc_feature
<222> LOCATION: (41)..(42)
<223> OTHER INFORMATION: 60% given sequence and 40% n

<400> SEQUENCE: 77
ctcgactttg gtgccctggc caaacgtsba atacgaatta tactgttggc agtaataagt        60
tgcaaaatca t                                                             71

<210> SEQ ID NO 78
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Vk1_5_L3r_SY
<220> FEATURE:
<221> NAME/KEY: misc_feature
<222> LOCATION: (28)..(28)
<223> OTHER INFORMATION: 60% given sequence and 40% m
<220> FEATURE:
<221> NAME/KEY: misc_feature
<222> LOCATION: (29)..(30)
<223> OTHER INFORMATION: 60% given sequence and 40% n
<220> FEATURE:
<221> NAME/KEY: misc_feature
<222> LOCATION: (31)..(31)
<223> OTHER INFORMATION: 60% given sequence and 40% m
<220> FEATURE:
<221> NAME/KEY: misc_feature
<222> LOCATION: (32)..(33)
<223> OTHER INFORMATION: 60% given sequence and 40% n
<220> FEATURE:
<221> NAME/KEY: misc_feature
<222> LOCATION: (34)..(34)
<223> OTHER INFORMATION: 60% given sequence and 40% m
<220> FEATURE:
<221> NAME/KEY: misc_feature
<222> LOCATION: (35)..(36)
<223> OTHER INFORMATION: 60% given sequence and 40% n
<220> FEATURE:
```

```
<221> NAME/KEY: misc_feature
<222> LOCATION: (37)..(37)
<223> OTHER INFORMATION: 60% given sequence and 40% m
<220> FEATURE:
<221> NAME/KEY: misc_feature
<222> LOCATION: (38)..(39)
<223> OTHER INFORMATION: 60% given sequence and 40% n
<220> FEATURE:
<221> NAME/KEY: misc_feature
<222> LOCATION: (40)..(40)
<223> OTHER INFORMATION: 60% given sequence and 40% m
<220> FEATURE:
<221> NAME/KEY: misc_feature
<222> LOCATION: (41)..(42)
<223> OTHER INFORMATION: 60% given sequence and 40% n
<220> FEATURE:
<221> NAME/KEY: misc_feature
<222> LOCATION: (43)..(43)
<223> OTHER INFORMATION: 60% given sequence and 40% m
<220> FEATURE:
<221> NAME/KEY: misc_feature
<222> LOCATION: (44)..(45)
<223> OTHER INFORMATION: 60% given sequence and 40% n

<400> SEQUENCE: 78
ctcgactttg gtgccctggc caaacgtmhr sgratacgaa ttatactgtt ggcagtaata    60
agttgcaaaa tcat                                                     74

<210> SEQ ID NO 79
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Vk1_5_L3r_SPY
<220> FEATURE:
<221> NAME/KEY: misc_feature
<222> LOCATION: (28)..(28)
<223> OTHER INFORMATION: 60% given sequence and 40% m
<220> FEATURE:
<221> NAME/KEY: misc_feature
<222> LOCATION: (29)..(30)
<223> OTHER INFORMATION: 60% given sequence and 40% n
<220> FEATURE:
<221> NAME/KEY: misc_feature
<222> LOCATION: (31)..(31)
<223> OTHER INFORMATION: 60% given sequence and 40% m
<220> FEATURE:
<221> NAME/KEY: misc_feature
<222> LOCATION: (32)..(33)
<223> OTHER INFORMATION: 60% given sequence and 40% n
<220> FEATURE:
<221> NAME/KEY: misc_feature
<222> LOCATION: (34)..(34)
<223> OTHER INFORMATION: 60% given sequence and 40% m
<220> FEATURE:
<221> NAME/KEY: misc_feature
<222> LOCATION: (35)..(36)
<223> OTHER INFORMATION: 60% given sequence and 40% n
<220> FEATURE:
<221> NAME/KEY: misc_feature
<222> LOCATION: (37)..(37)
<223> OTHER INFORMATION: 60% given sequence and 40% m
<220> FEATURE:
<221> NAME/KEY: misc_feature
<222> LOCATION: (38)..(39)
<223> OTHER INFORMATION: 60% given sequence and 40% n
<220> FEATURE:
<221> NAME/KEY: misc_feature
<222> LOCATION: (40)..(40)
<223> OTHER INFORMATION: 60% given sequence and 40% m
<220> FEATURE:
<221> NAME/KEY: misc_feature
<222> LOCATION: (41)..(42)
```

```
<223> OTHER INFORMATION: 60% given sequence and 40% n
<220> FEATURE:
<221> NAME/KEY: misc_feature
<222> LOCATION: (43)..(43)
<223> OTHER INFORMATION: 60% given sequence and 40% m
<220> FEATURE:
<221> NAME/KEY: misc_feature
<222> LOCATION: (44)..(45)
<223> OTHER INFORMATION: 60% given sequence and 40% n
<220> FEATURE:
<221> NAME/KEY: misc_feature
<222> LOCATION: (46)..(46)
<223> OTHER INFORMATION: 60% given sequence and 40% m
<220> FEATURE:
<221> NAME/KEY: misc_feature
<222> LOCATION: (47)..(48)
<223> OTHER INFORMATION: 60% given sequence and 40% n

<400> SEQUENCE: 79
ctcgactttg gtgccctggc caaacgtmhh msssgratac gaattatact gttggcagta      60
ataagttgca aaatcat                                                    77

<210> SEQ ID NO 80
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RJH31

<400> SEQUENCE: 80
acgtttggcc agggcaccaa agtcgag                                         27

<210> SEQ ID NO 81
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RJH32

<400> SEQUENCE: 81
tctcgcacag taatacacgg cggtgtcc                                        28

<210> SEQ ID NO 82
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DP88-v4-4
<220> FEATURE:
<221> NAME/KEY: modified_base
<222> LOCATION: (29)..(31)
<223> OTHER INFORMATION: a, c, t or g
<220> FEATURE:
<221> NAME/KEY: misc_feature
<222> LOCATION: (29)..(31)
<223> OTHER INFORMATION: This region encodes G/D = 20%, E/V/S = 10%,
      A/P/R/L/T/Y=5%
<220> FEATURE:
<221> NAME/KEY: modified_base
<222> LOCATION: (32)..(34)
<223> OTHER INFORMATION: a, c, t or g
<220> FEATURE:
<221> NAME/KEY: misc_feature
```

```
<222> LOCATION: (32)..(34)
<223> OTHER INFORMATION: This region encodes G/Y/S=15%,
      A/D/T/R/P/L/V/N/W/F/I/E = 4,6%
<220> FEATURE:
<221> NAME/KEY: modified_base
<222> LOCATION: (35)..(37)
<223> OTHER INFORMATION: a, c, t or g
<220> FEATURE:
<221> NAME/KEY: misc_feature
<222> LOCATION: (35)..(37)
<223> OTHER INFORMATION: This region encodes G/Y/S=15%,
      A/D/T/R/P/L/V/N/W/F/I/E = 4,6%
<220> FEATURE:
<221> NAME/KEY: modified_base
<222> LOCATION: (38)..(40)
<223> OTHER INFORMATION: a, c, t or g
<220> FEATURE:
<221> NAME/KEY: misc_feature
<222> LOCATION: (38)..(40)
<223> OTHER INFORMATION: This region encodes G/A/Y = 20%, P/W/S/D/T = 8%
<220> FEATURE:
<221> NAME/KEY: modified_base
<222> LOCATION: (41)..(43)
<223> OTHER INFORMATION: a, c, t or g
<220> FEATURE:
<221> NAME/KEY: misc_feature
<222> LOCATION: (41)..(43)
<223> OTHER INFORMATION: This region encodes F = 46%, L/M = 15%,
      G/I/Y = 8%

<400> SEQUENCE: 82
ggacaccgcc gtgtattact gtgcgagann nnnnnnnnnn nnngactact ggggccaagg    60
gaccaccgtg accgtctcc                                                 79

<210> SEQ ID NO 83
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DP88-v4-6
<220> FEATURE:
<221> NAME/KEY: modified_base
<222> LOCATION: (29)..(31)
<223> OTHER INFORMATION: a, c, t or g
<220> FEATURE:
<221> NAME/KEY: misc_feature
<222> LOCATION: (29)..(31)
<223> OTHER INFORMATION: This region encodes G/D = 20%, E/V/S = 10%,
      A/P/R/L/T/Y=5%
<220> FEATURE:
<221> NAME/KEY: modified_base
<222> LOCATION: (32)..(34)
<223> OTHER INFORMATION: a, c, t or g
<220> FEATURE:
<221> NAME/KEY: misc_feature
<222> LOCATION: (32)..(34)
<223> OTHER INFORMATION: This region encodes G/Y/S=15%,
      A/D/T/R/P/L/V/N/W/F/I/E = 4,6%
<220> FEATURE:
<221> NAME/KEY: modified_base
<222> LOCATION: (35)..(37)
<223> OTHER INFORMATION: a, c, t or g
<220> FEATURE:
<221> NAME/KEY: misc_feature
<222> LOCATION: (35)..(37)
<223> OTHER INFORMATION: This region encodes G/Y/S=15%,
      A/D/T/R/P/L/V/N/W/F/I/E = 4,6%
<220> FEATURE:
<221> NAME/KEY: modified_base
<222> LOCATION: (38)..(40)
<223> OTHER INFORMATION: a, c, t or g
<220> FEATURE:
<221> NAME/KEY: misc_feature
```

```
<222> LOCATION: (38)..(40)
<223> OTHER INFORMATION: This region encodes G/Y/S=15%,
      A/D/T/R/P/L/V/N/W/F/I/E = 4,6%
<220> FEATURE:
<221> NAME/KEY: modified_base
<222> LOCATION: (41)..(43)
<223> OTHER INFORMATION: a, c, t or g
<220> FEATURE:
<221> NAME/KEY: misc_feature
<222> LOCATION: (41)..(43)
<223> OTHER INFORMATION: This region encodes G/Y/S=15%,
      A/D/T/R/P/L/V/N/W/F/I/E = 4,6%
<220> FEATURE:
<221> NAME/KEY: modified_base
<222> LOCATION: (44)..(46)
<223> OTHER INFORMATION: a, c, t or g
<220> FEATURE:
<221> NAME/KEY: misc_feature
<222> LOCATION: (44)..(46)
<223> OTHER INFORMATION: This region encodes G/A/Y = 20%, P/W/S/D/T = 8%
<220> FEATURE:
<221> NAME/KEY: modified_base
<222> LOCATION: (47)..(49)
<223> OTHER INFORMATION: a, c, t or g
<220> FEATURE:
<221> NAME/KEY: misc_feature
<222> LOCATION: (47)..(49)
<223> OTHER INFORMATION: This region encodes F = 46%, L/M = 15%,
      G/I/Y = 8%

<400> SEQUENCE: 83
ggacaccgcc gtgtattact gtgcgagann nnnnnnnnnn nnnnnnnnng actactgggg    60
ccaagggacc accgtgaccg tctcc                                          85

<210> SEQ ID NO 84
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DP88-v4-8
<220> FEATURE:
<221> NAME/KEY: modified_base
<222> LOCATION: (29)..(31)
<223> OTHER INFORMATION: a, c, t or g
<220> FEATURE:
<221> NAME/KEY: misc_feature
<222> LOCATION: (29)..(31)
<223> OTHER INFORMATION: This region encodes G/D = 20%, E/V/S = 10%,
      A/P/R/L/T/Y=5%
<220> FEATURE:
<221> NAME/KEY: modified_base
<222> LOCATION: (32)..(34)
<223> OTHER INFORMATION: a, c, t or g
<220> FEATURE:
<221> NAME/KEY: misc_feature
<222> LOCATION: (32)..(34)
<223> OTHER INFORMATION: This region encodes G/Y/S=15%,
      A/D/T/R/P/L/V/N/W/F/I/E = 4,6%
<220> FEATURE:
<221> NAME/KEY: modified_base
<222> LOCATION: (35)..(37)
<223> OTHER INFORMATION: a, c, t or g
<220> FEATURE:
<221> NAME/KEY: misc_feature
<222> LOCATION: (35)..(37)
<223> OTHER INFORMATION: This region encodes G/Y/S=15%,
      A/D/T/R/P/L/V/N/W/F/I/E = 4,6%
<220> FEATURE:
<221> NAME/KEY: modified_base
<222> LOCATION: (38)..(40)
<223> OTHER INFORMATION: a, c, t or g
<220> FEATURE:
<221> NAME/KEY: misc_feature
```

<222> LOCATION: (38)..(40)
<223> OTHER INFORMATION: This region encodes G/Y/S=15%,
      A/D/T/R/P/L/V/N/W/F/I/E = 4,6%
<220> FEATURE:
<221> NAME/KEY: modified_base
<222> LOCATION: (41)..(43)
<223> OTHER INFORMATION: a, c, t or g
<220> FEATURE:
<221> NAME/KEY: misc_feature
<222> LOCATION: (41)..(43)
<223> OTHER INFORMATION: This region encodes G/Y/S=15%,
      A/D/T/R/P/L/V/N/W/F/I/E = 4,6%
<220> FEATURE:
<221> NAME/KEY: modified_base
<222> LOCATION: (44)..(46)
<223> OTHER INFORMATION: a, c, t or g
<220> FEATURE:
<221> NAME/KEY: misc_feature
<222> LOCATION: (44)..(46)
<223> OTHER INFORMATION: This region encodes G/Y/S=15%,
      A/D/T/R/P/L/V/N/W/F/I/E = 4,6%
<220> FEATURE:
<221> NAME/KEY: modified_base
<222> LOCATION: (47)..(49)
<223> OTHER INFORMATION: a, c, t or g
<220> FEATURE:
<221> NAME/KEY: misc_feature
<222> LOCATION: (47)..(49)
<223> OTHER INFORMATION: This region encodes G/Y/S=15%,
      A/D/T/R/P/L/V/N/W/F/I/E = 4,6%
<220> FEATURE:
<221> NAME/KEY: modified_base
<222> LOCATION: (50)..(52)
<223> OTHER INFORMATION: a, c, t or g
<220> FEATURE:
<221> NAME/KEY: misc_feature
<222> LOCATION: (50)..(52)
<223> OTHER INFORMATION: This region encodes G/A/Y = 20%, P/W/S/D/T = 8%
<220> FEATURE:
<221> NAME/KEY: modified_base
<222> LOCATION: (53)..(55)
<223> OTHER INFORMATION: a, c, t or g
<220> FEATURE:
<221> NAME/KEY: misc_feature
<222> LOCATION: (53)..(55)
<223> OTHER INFORMATION: This region encodes F = 46%, L/M = 15%,
      G/I/Y = 8%

<400> SEQUENCE: 84
ggacaccgcc gtgtattact gtgcgagann nnnnnnnnnn nnnnnnnnnn nnnnngacta    60
ctggggccaa gggaccaccg tgaccgtctc c                                   91

<210> SEQ ID NO 85
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: fdseqlong

<400> SEQUENCE: 85
gacgttagta aatgaattt ctgtatgagg                                      30

<210> SEQ ID NO 86
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Vl_3_19_L3r_V

```
<220> FEATURE:
<221> NAME/KEY: misc_feature
<222> LOCATION: (32)..(32)
<223> OTHER INFORMATION: 60% original base and 40% randomization as m
<220> FEATURE:
<221> NAME/KEY: misc_feature
<222> LOCATION: (33)..(34)
<223> OTHER INFORMATION: 60% original base and 40% randomization as n
<220> FEATURE:
<221> NAME/KEY: misc_feature
<222> LOCATION: (35)..(35)
<223> OTHER INFORMATION: 60% original base and 40% randomization as m
<220> FEATURE:
<221> NAME/KEY: misc_feature
<222> LOCATION: (36)..(37)
<223> OTHER INFORMATION: 60% original base and 40% randomization as n
<220> FEATURE:
<221> NAME/KEY: misc_feature
<222> LOCATION: (38)..(38)
<223> OTHER INFORMATION: 60% original base and 40% randomization as m
<220> FEATURE:
<221> NAME/KEY: misc_feature
<222> LOCATION: (39)..(40)
<223> OTHER INFORMATION: 60% original base and 40% randomization as n
<220> FEATURE:
<221> NAME/KEY: misc_feature
<222> LOCATION: (41)..(41)
<223> OTHER INFORMATION: 60% original base and 40% randomization as m
<220> FEATURE:
<221> NAME/KEY: misc_feature
<222> LOCATION: (42)..(43)
<223> OTHER INFORMATION: 60% original base and 40% randomization as n
<220> FEATURE:
<221> NAME/KEY: misc_feature
<222> LOCATION: (44)..(44)
<223> OTHER INFORMATION: 60% original base and 40% randomization as m
<220> FEATURE:
<221> NAME/KEY: misc_feature
<222> LOCATION: (45)..(46)
<223> OTHER INFORMATION: 60% original base and 40% randomization as n
<220> FEATURE:
<221> NAME/KEY: misc_feature
<222> LOCATION: (47)..(47)
<223> OTHER INFORMATION: 60% original base and 40% randomization as m
<220> FEATURE:
<221> NAME/KEY: misc_feature
<222> LOCATION: (48)..(49)
<223> OTHER INFORMATION: 60% original base and 40% randomization as n
<220> FEATURE:
<221> NAME/KEY: misc_feature
<222> LOCATION: (50)..(50)
<223> OTHER INFORMATION: 60% original base and 40% randomization as m
<220> FEATURE:
<221> NAME/KEY: misc_feature
<222> LOCATION: (51)..(52)
<223> OTHER INFORMATION: 60% original base and 40% randomization as n

<400> SEQUENCE: 86
ggacggtcag cttggtccct ccgccgaata cvhvattacc gctactatca cgggagttac    60
agtaatagtc agcctcatct tccgc                                          85

<210> SEQ ID NO 87
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: V1_3_19_L3r_HV
<220> FEATURE:
<221> NAME/KEY: misc_feature
<222> LOCATION: (32)..(32)
<223> OTHER INFORMATION: 60% original base and 40% randomization as m
<220> FEATURE:
<221> NAME/KEY: misc_feature
```

<222> LOCATION: (33)..(34)
<223> OTHER INFORMATION: 60% original base and 40% randomization as n
<220> FEATURE:
<221> NAME/KEY: misc_feature
<222> LOCATION: (35)..(35)
<223> OTHER INFORMATION: 60% original base and 40% randomization as m
<220> FEATURE:
<221> NAME/KEY: misc_feature
<222> LOCATION: (36)..(37)
<223> OTHER INFORMATION: 60% original base and 40% randomization as n
<220> FEATURE:
<221> NAME/KEY: misc_feature
<222> LOCATION: (38)..(38)
<223> OTHER INFORMATION: 60% original base and 40% randomization as m
<220> FEATURE:
<221> NAME/KEY: misc_feature
<222> LOCATION: (39)..(40)
<223> OTHER INFORMATION: 60% original base and 40% randomization as n
<220> FEATURE:
<221> NAME/KEY: misc_feature
<222> LOCATION: (41)..(41)
<223> OTHER INFORMATION: 60% original base and 40% randomization as m
<220> FEATURE:
<221> NAME/KEY: misc_feature
<222> LOCATION: (42)..(43)
<223> OTHER INFORMATION: 60% original base and 40% randomization as n
<220> FEATURE:
<221> NAME/KEY: misc_feature
<222> LOCATION: (44)..(44)
<223> OTHER INFORMATION: 60% original base and 40% randomization as m
<220> FEATURE:
<221> NAME/KEY: misc_feature
<222> LOCATION: (45)..(46)
<223> OTHER INFORMATION: 60% original base and 40% randomization as n
<220> FEATURE:
<221> NAME/KEY: misc_feature
<222> LOCATION: (47)..(47)
<223> OTHER INFORMATION: 60% original base and 40% randomization as m
<220> FEATURE:
<221> NAME/KEY: misc_feature
<222> LOCATION: (48)..(49)
<223> OTHER INFORMATION: 60% original base and 40% randomization as n
<220> FEATURE:
<221> NAME/KEY: misc_feature
<222> LOCATION: (50)..(50)
<223> OTHER INFORMATION: 60% original base and 40% randomization as m
<220> FEATURE:
<221> NAME/KEY: misc_feature
<222> LOCATION: (51)..(52)
<223> OTHER INFORMATION: 60% original base and 40% randomization as n
<220> FEATURE:
<221> NAME/KEY: misc_feature
<222> LOCATION: (53)..(53)
<223> OTHER INFORMATION: 60% original base and 40% randomization as m
<220> FEATURE:
<221> NAME/KEY: misc_feature
<222> LOCATION: (54)..(55)
<223> OTHER INFORMATION: 60% original base and 40% randomization as n

<400> SEQUENCE: 87
ggacggtcag cttggtccct ccgccgaata ccmmatgatt accgctacta tcacgggagt      60
tacagtaata gtcagcctca tcttccgc      88

<210> SEQ ID NO 88
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Vl_3_19_L3r_HLV
<220> FEATURE:
<221> NAME/KEY: misc_feature
<222> LOCATION: (32)..(32)
<223> OTHER INFORMATION: 60% original base and 40% randomization as m

```
<220> FEATURE:
<221> NAME/KEY: misc_feature
<222> LOCATION: (33)..(34)
<223> OTHER INFORMATION: 60% original base and 40% randomization as n
<220> FEATURE:
<221> NAME/KEY: misc_feature
<222> LOCATION: (35)..(35)
<223> OTHER INFORMATION: 60% original base and 40% randomization as m
<220> FEATURE:
<221> NAME/KEY: misc_feature
<222> LOCATION: (36)..(37)
<223> OTHER INFORMATION: 60% original base and 40% randomization as n
<220> FEATURE:
<221> NAME/KEY: misc_feature
<222> LOCATION: (38)..(38)
<223> OTHER INFORMATION: 60% original base and 40% randomization as m
<220> FEATURE:
<221> NAME/KEY: misc_feature
<222> LOCATION: (39)..(40)
<223> OTHER INFORMATION: 60% original base and 40% randomization as n
<220> FEATURE:
<221> NAME/KEY: misc_feature
<222> LOCATION: (41)..(41)
<223> OTHER INFORMATION: 60% original base and 40% randomization as m
<220> FEATURE:
<221> NAME/KEY: misc_feature
<222> LOCATION: (42)..(43)
<223> OTHER INFORMATION: 60% original base and 40% randomization as n
<220> FEATURE:
<221> NAME/KEY: misc_feature
<222> LOCATION: (44)..(44)
<223> OTHER INFORMATION: 60% original base and 40% randomization as m
<220> FEATURE:
<221> NAME/KEY: misc_feature
<222> LOCATION: (45)..(46)
<223> OTHER INFORMATION: 60% original base and 40% randomization as n
<220> FEATURE:
<221> NAME/KEY: misc_feature
<222> LOCATION: (47)..(47)
<223> OTHER INFORMATION: 60% original base and 40% randomization as m
<220> FEATURE:
<221> NAME/KEY: misc_feature
<222> LOCATION: (48)..(49)
<223> OTHER INFORMATION: 60% original base and 40% randomization as n
<220> FEATURE:
<221> NAME/KEY: misc_feature
<222> LOCATION: (50)..(50)
<223> OTHER INFORMATION: 60% original base and 40% randomization as m
<220> FEATURE:
<221> NAME/KEY: misc_feature
<222> LOCATION: (51)..(52)
<223> OTHER INFORMATION: 60% original base and 40% randomization as n
<220> FEATURE:
<221> NAME/KEY: misc_feature
<222> LOCATION: (53)..(53)
<223> OTHER INFORMATION: 60% original base and 40% randomization as m
<220> FEATURE:
<221> NAME/KEY: misc_feature
<222> LOCATION: (54)..(55)
<223> OTHER INFORMATION: 60% original base and 40% randomization as n
<220> FEATURE:
<221> NAME/KEY: misc_feature
<222> LOCATION: (56)..(56)
<223> OTHER INFORMATION: 60% original base and 40% randomization as m
<220> FEATURE:
<221> NAME/KEY: misc_feature
<222> LOCATION: (57)..(58)
<223> OTHER INFORMATION: 60% original base and 40% randomization as n

<400> SEQUENCE: 88
ggacggtcag cttggtccct ccgccgaata crhmvwgatg attaccgcta ctatcacggg    60
agttacagta atagtcagcc tcatcttccg c                                  91

<210> SEQ ID NO 89
<211> LENGTH: 28
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: RJH80

<400> SEQUENCE: 89
ttcggcggag ggaccaagct gaccgtcc                                              28

<210> SEQ ID NO 90
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DP47CDR3_ba (mod.)

<400> SEQUENCE: 90
cgcacagtaa tatacggccg tgtcc                                                 25

<210> SEQ ID NO 91
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DP47-v4-4
<220> FEATURE:
<221> NAME/KEY: modified_base
<222> LOCATION: (29)..(31)
<223> OTHER INFORMATION: a, c, t or g
<220> FEATURE:
<221> NAME/KEY: misc_feature
<222> LOCATION: (29)..(31)
<223> OTHER INFORMATION: This region encodes K=70%, R=30%
<220> FEATURE:
<221> NAME/KEY: modified_base
<222> LOCATION: (32)..(34)
<223> OTHER INFORMATION: a, c, t or g
<220> FEATURE:
<221> NAME/KEY: misc_feature
<222> LOCATION: (32)..(34)
<223> OTHER INFORMATION: This region encodes G/D=20%, E/V/S=10%,
      A/P/R/L/T/Y=5%
<220> FEATURE:
<221> NAME/KEY: modified_base
<222> LOCATION: (35)..(37)
<223> OTHER INFORMATION: a, c, t or g
<220> FEATURE:
<221> NAME/KEY: misc_feature
<222> LOCATION: (35)..(37)
<223> OTHER INFORMATION: This region encodes G/Y/S=15%,
      A/D/T/R/P/L/V/N/W/F/I/E=4,6%
<220> FEATURE:
<221> NAME/KEY: modified_base
<222> LOCATION: (38)..(40)
<223> OTHER INFORMATION: a, c, t or g
<220> FEATURE:
<221> NAME/KEY: misc_feature
<222> LOCATION: (38)..(40)
<223> OTHER INFORMATION: This region encodes G/Y/S=15%,
      A/D/T/R/P/L/V/N/W/F/I/E=4,6%
<220> FEATURE:
<221> NAME/KEY: modified_base
<222> LOCATION: (41)..(43)
<223> OTHER INFORMATION: a, c, t or g
<220> FEATURE:
<221> NAME/KEY: misc_feature
<222> LOCATION: (41)..(43)
<223> OTHER INFORMATION: This region encodes G/A/Y=20, P/W/S/D/T=8%
```

-continued

```
<220> FEATURE:
<221> NAME/KEY: modified_base
<222> LOCATION: (44)..(46)
<223> OTHER INFORMATION: a, c, t or g
<220> FEATURE:
<221> NAME/KEY: misc_feature
<222> LOCATION: (44)..(46)
<223> OTHER INFORMATION: This region encodes F=46%, L/M=15%, G/I/Y=8%

<400> SEQUENCE: 91
cgaggacacg gccgtatatt actgtgcgnn nnnnnnnnnn nnnnnngact actggggcca    60
aggaaccctg gtcaccgtct cg                                             82

<210> SEQ ID NO 92
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DP47-v4-6
<220> FEATURE:
<221> NAME/KEY: modified_base
<222> LOCATION: (29)..(31)
<223> OTHER INFORMATION: a, c, t or g
<220> FEATURE:
<221> NAME/KEY: misc_feature
<222> LOCATION: (29)..(31)
<223> OTHER INFORMATION: This region encodes K=70%, R=30%
<220> FEATURE:
<221> NAME/KEY: modified_base
<222> LOCATION: (32)..(34)
<223> OTHER INFORMATION: a, c, t or g
<220> FEATURE:
<221> NAME/KEY: misc_feature
<222> LOCATION: (32)..(34)
<223> OTHER INFORMATION: This region encodes G/D=20%, E/V/S=10%,
      A/P/R/L/T/Y=5%
<220> FEATURE:
<221> NAME/KEY: modified_base
<222> LOCATION: (35)..(37)
<223> OTHER INFORMATION: a, c, t or g
<220> FEATURE:
<221> NAME/KEY: misc_feature
<222> LOCATION: (35)..(37)
<223> OTHER INFORMATION: This region encodes G/Y/S=15%,
      A/D/T/R/P/L/V/N/W/F/I/E=4,6%
<220> FEATURE:
<221> NAME/KEY: modified_base
<222> LOCATION: (38)..(40)
<223> OTHER INFORMATION: a, c, t or g
<220> FEATURE:
<221> NAME/KEY: misc_feature
<222> LOCATION: (38)..(40)
<223> OTHER INFORMATION: This region encodes G/Y/S=15%,
      A/D/T/R/P/L/V/N/W/F/I/E=4,6%
<220> FEATURE:
<221> NAME/KEY: modified_base
<222> LOCATION: (41)..(43)
<223> OTHER INFORMATION: a, c, t or g
<220> FEATURE:
<221> NAME/KEY: misc_feature
<222> LOCATION: (41)..(43)
<223> OTHER INFORMATION: This region encodes G/Y/S=15%,
      A/D/T/R/P/L/V/N/W/F/I/E=4,6%
<220> FEATURE:
<221> NAME/KEY: modified_base
<222> LOCATION: (44)..(46)
<223> OTHER INFORMATION: a, c, t or g
<220> FEATURE:
<221> NAME/KEY: misc_feature
<222> LOCATION: (44)..(46)
<223> OTHER INFORMATION: This region encodes G/Y/S=15%,
      A/D/T/R/P/L/V/N/W/F/I/E=4,6%
<220> FEATURE:
```

```
<221> NAME/KEY: modified_base
<222> LOCATION: (47)..(49)
<223> OTHER INFORMATION: a, c, t or g
<220> FEATURE:
<221> NAME/KEY: misc_feature
<222> LOCATION: (47)..(49)
<223> OTHER INFORMATION: This region encodes G/A/Y=20, P/W/S/D/T=8%
<220> FEATURE:
<221> NAME/KEY: modified_base
<222> LOCATION: (50)..(52)
<223> OTHER INFORMATION: a, c, t or g
<220> FEATURE:
<221> NAME/KEY: misc_feature
<222> LOCATION: (50)..(52)
<223> OTHER INFORMATION: This region encodes F=46%, L/M=15%, G/I/Y=8%

<400> SEQUENCE: 92
cgaggacacg gccgtatatt actgtgcgnn nnnnnnnnnn nnnnnnnnnn nngactactg    60
gggccaagga accctggtca ccgtctcg                                      88

<210> SEQ ID NO 93
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DP47-v4-8
<220> FEATURE:
<221> NAME/KEY: modified_base
<222> LOCATION: (29)..(31)
<223> OTHER INFORMATION: a, c, t or g
<220> FEATURE:
<221> NAME/KEY: misc_feature
<222> LOCATION: (29)..(31)
<223> OTHER INFORMATION: This region encodes K=70%, R=30%
<220> FEATURE:
<221> NAME/KEY: modified_base
<222> LOCATION: (32)..(34)
<223> OTHER INFORMATION: a, c, t or g
<220> FEATURE:
<221> NAME/KEY: misc_feature
<222> LOCATION: (32)..(34)
<223> OTHER INFORMATION: This region encodes G/D=20%, E/V/S=10%,
      A/P/R/L/T/Y=5%
<220> FEATURE:
<221> NAME/KEY: modified_base
<222> LOCATION: (35)..(37)
<223> OTHER INFORMATION: a, c, t or g
<220> FEATURE:
<221> NAME/KEY: misc_feature
<222> LOCATION: (35)..(37)
<223> OTHER INFORMATION: This region encodes G/Y/S=15%,
      A/D/T/R/P/L/V/N/W/F/I/E=4,6%
<220> FEATURE:
<221> NAME/KEY: modified_base
<222> LOCATION: (38)..(40)
<223> OTHER INFORMATION: a, c, t or g
<220> FEATURE:
<221> NAME/KEY: misc_feature
<222> LOCATION: (38)..(40)
<223> OTHER INFORMATION: This region encodes G/Y/S=15%,
      A/D/T/R/P/L/V/N/W/F/I/E=4,6%
<220> FEATURE:
<221> NAME/KEY: modified_base
<222> LOCATION: (41)..(43)
<223> OTHER INFORMATION: a, c, t or g
<220> FEATURE:
<221> NAME/KEY: misc_feature
<222> LOCATION: (41)..(43)
<223> OTHER INFORMATION: This region encodes G/Y/S=15%,
      A/D/T/R/P/L/V/N/W/F/I/E=4,6%
<220> FEATURE:
<221> NAME/KEY: modified_base
<222> LOCATION: (44)..(46)
```

```
<223> OTHER INFORMATION: a, c, t or g
<220> FEATURE:
<221> NAME/KEY: misc_feature
<222> LOCATION: (44)..(46)
<223> OTHER INFORMATION: This region encodes G/Y/S=15%,
      A/D/T/R/P/L/V/N/W/F/I/E=4,6%
<220> FEATURE:
<221> NAME/KEY: modified_base
<222> LOCATION: (47)..(49)
<223> OTHER INFORMATION: a, c, t or g
<220> FEATURE:
<221> NAME/KEY: misc_feature
<222> LOCATION: (47)..(49)
<223> OTHER INFORMATION: This region encodes G/Y/S=15%,
      A/D/T/R/P/L/V/N/W/F/I/E=4,6%
<220> FEATURE:
<221> NAME/KEY: modified_base
<222> LOCATION: (50)..(52)
<223> OTHER INFORMATION: a, c, t or g
<220> FEATURE:
<221> NAME/KEY: misc_feature
<222> LOCATION: (50)..(52)
<223> OTHER INFORMATION: This region encodes G/Y/S=15%,
      A/D/T/R/P/L/V/N/W/F/I/E=4,6%
<220> FEATURE:
<221> NAME/KEY: modified_base
<222> LOCATION: (53)..(55)
<223> OTHER INFORMATION: a, c, t or g
<220> FEATURE:
<221> NAME/KEY: misc_feature
<222> LOCATION: (53)..(55)
<223> OTHER INFORMATION: This region encodes G/A/Y=20, P/W/S/D/T=8%
<220> FEATURE:
<221> NAME/KEY: modified_base
<222> LOCATION: (56)..(58)
<223> OTHER INFORMATION: a, c, t or g
<220> FEATURE:
<221> NAME/KEY: misc_feature
<222> LOCATION: (56)..(58)
<223> OTHER INFORMATION: This region encodes F=46%, L/M=15%, G/I/Y=8%

<400> SEQUENCE: 93
cgaggacacg gccgtatatt actgtgcgnn nnnnnnnnnn nnnnnnnnnn nnnnnnnnga    60
ctactggggc caaggaaccc tggtcaccgt ctcg                               94
```

MODIFIED ANTI-TENASCIN ANTIBODIES AND METHODS OF USE

CROSS REFERENCE TO RELATED APPLICATIONS

This application is a continuation of International Application No. PCT/EP2017/060869, filed May 8, 2017, which claims priority from European Patent Application No. 16169239.7, filed May 11, 2016. The contents of each of the foregoing applications are incorporated herein by reference in their entireties.

SEQUENCE LISTING

This application contains a Sequence Listing submitted via EFS-Web and hereby incorporated by reference in its entirety. Said ASCII copy, created on Nov. 2, 2018, is named P33585-US-SequenceListing.txt and is 147,456 bytes in size.

FIELD OF THE INVENTION

The present invention relates to improved antibodies specific for Tenascin-C (TnC), in particular domain specific anti-TnC antibodies with improved cross-species reactivity. In addition, the invention relates to polynuleotides encoding such antibodies, and vectors and host cells comprising such polynucleotides. The invention further relates to methods for producing the antibodies and methods of using them in the treatment of disease.

BACKGROUND

TnC and Anti-TnC Antibodies

Tenascins are a highly conserved family of large multimeric extracellular matrix (ECM) glycoproteins, which is found in vertebrates. Four tenascin paralogues have been identified in mammals, termed Tenascin-C (TnC), tenascin-R, tenascin-X and tenascin-W. Tenascin family proteins have a common primary structure, comprising N-terminal heptad repeats, epidermal growth factor (EGF)-like repeats, fibronectin type III domain repeats and a C-terminal fibrinogen-like globular domain. Via an N-terminal oligomerization domain, individual subunits assemble into trimers or, as is the case for Tenascin-C, even hexamers.

Mammalian TnC monomers typically have 14.5 EGF-like repeats and 8 fibronectin type III domain repeats that are shared by all TnC isoforms. However, up to 9 additional fibronectin type III domain repeats (domains A1 to D) can be independently included or excluded by alternative splicing, giving rise to a large number of TnC isoforms (see e.g., Hsia and Schwarzbauer, J Biol Chem 280, 26641-26644 (2005)).

TnC is transiently expressed in the developing embryo, but virtually absent from adult tissues. It reappears, however, in tissues undergoing remodeling processes, including certain pathological conditions such as wound healing, inflammation and cancer (reviewed in Chiquet-Ehrismann & Chiquet, J Pathol 200, 488-499 (2003)).

Importantly, TnC is highly expressed in the majority of malignant solid tumors, including tumors of the brain, breast, colon, lung, skin and other organs (reviewed in Orend and Chiquet-Ehrismann, Cancer Letters 244, 143-163 (2006)), where it may be expressed by transformed epithelial cells as well as stromal cells in the tumor microenvironment (Yoshida et al., J Pathol 182, 421-428 (1997), Hanamura et al., Int J Cancer 73, 10-15 (1997)). In particular, the "large isoform" of TnC, containing the alternatively spliced domains A1 to D, is expressed in invasive carcinomas while being nearly undetectable in healthy adult tissues (Borsi et al., Int J Cancer 52, 688-692 (1992), Carnemolla et al., Eur J Biochem 205, 561-567 (1992)).

Its expression pattern makes TnC, in particular its alternatively spliced domains, a promising antigen for tumor targeting applications, and accordingly a number of antibodies against several domains of the protein have been developed (see e.g., Brack et al., Clin Cancer Res 12, 3200-3208 (2006) or EP 1 817 345, describing antibodies against the A1 domain of TnC; Silacci et al., Prot Eng Des Sel 19, 471-478 (2006), or EP 1 173 766, describing antibodies against the C domain of TnC; Wang et al., Hybridoma 29, 13-16 (2010), describing an antibody against the D domain of TnC; or Balza et al., FEBS 332, 39-43 (1993), describing several antibodies against different domains of human tenascin). Recently, also antibodies recognizing a specific epitope in the A2 domain of human TnC has been described (WO 2009/089998 and WO 2012/020038).

Still, there remains a need for tenascin antibodies with improved therapeutic potential for human therapy. Specifically targeting tenascin isoforms with high affinity and cross-species reactivity is much needed for improved cancer therapy, including, but not limited to, humans.

SUMMARY

The present invention provides antibodies that specifically bind to TnC, having a high affinity and/or improved cross-species reactivity.

In one aspect, the invention is directed to an antibody that specifically binds to TnC, comprising at least one (i.e., one, two, three, four, five or six) of the complementarity determining regions (CDRs) set forth in SEQ ID NO: 37, SEQ ID NO: 38, SEQ ID NO: 39, SEQ ID NO: 40, SEQ ID NO: 41, SEQ ID NO: 42, SEQ ID NO: 49, SEQ ID NO: 50, SEQ ID NO: 51, SEQ ID NO: 52, SEQ ID NO: 53 and SEQ ID NO: 54. In one embodiment, the antibody comprises three heavy chain CDRs (i.e., HCDR1, HCDR2, and HCDR3) and/or three light chain CDRs (i.e., LCDR1, LCDR2, and LCDR3) selected from SEQ ID NO: 37, SEQ ID NO: 38, SEQ ID NO: 39, SEQ ID NO: 40, SEQ ID NO: 41, SEQ ID NO: 42, SEQ ID NO: 49, SEQ ID NO: 50, SEQ ID NO: 51, SEQ ID NO: 52, SEQ ID NO: 53 and SEQ ID NO: 54.

In one embodiment, the antibody specifically binds to Tenascin-C (TnC), wherein said antibody comprises a heavy chain variable region comprising
(a) a heavy chain CDR1 selected from the group of SEQ ID NO: 49 and SEQ ID NO: 52;
(b) a heavy chain CDR2 selected from the group of SEQ ID NO: 50 and SEQ ID NO: 53;
(c) a heavy chain CDR3 selected from the group of SEQ ID NO: 51 and SEQ ID NO: 54,
and a light chain variable region comprising
(a) a light chain CDR1 selected from the group of SEQ ID NO: 37 and SEQ ID NO: 40;
(b) a light chain CDR2 selected from the group of SEQ ID NO: 38 and SEQ ID NO: 41, and (c) a light chain CDR3 selected from the group of SEQ ID NO: 39 and SEQ ID NO: 42.

In a particular embodiment, the antibody specifically binds to Tenascin-C (TnC), wherein said antibody comprises a heavy chain variable region comprising
(a) the heavy chain CDR1 of SEQ ID NO: 49;
(b) the heavy chain CDR2 of SEQ ID NO: 50;

(c) the heavy chain CDR3 of SEQ ID NO: 51,
and a light chain variable region comprising
(a) the light chain CDR1 of SEQ ID NO: 37;
(b) the light chain CDR2 of SEQ ID NO: 38, and
(c) the light chain CDR3 of SEQ ID NO: 39.

In another particular embodiment, the antibody specifically binds to Tenascin-C (TnC), wherein said antibody comprises a heavy chain variable region comprising
(a) the heavy chain CDR1 of SEQ ID NO: 52;
(b) the heavy chain CDR2 of SEQ ID NO: 53;
(c) the heavy chain CDR3 of SEQ ID NO: 54,
and a light chain variable region comprising
(a) the light chain CDR1 of SEQ ID NO: 40;
(b) the light chain CDR2 of SEQ ID NO: 41, and
(c) the light chain CDR3 of SEQ ID NO: 42.

In one embodiment, the antibody comprises an antibody heavy chain variable region and/or an antibody light chain variable region, particularly both a heavy and light chain variable region, selected from the heavy and light chain variable region sequences set forth in SEQ ID NO: 27, SEQ ID NO: 28, SEQ ID NO: 29 and SEQ ID NO: 30. In a particular embodiment, the antibody comprises a heavy chain variable region comprising an amino acid sequence of SEQ ID NO: 28 and a light chain variable region comprising an amino acid sequence of SEQ ID NO: 27. In another particular embodiment, the antibody comprises a heavy chain variable region comprising an amino acid sequence of SEQ ID NO: 30 and a light chain variable region comprising an amino acid sequence of SEQ ID NO: 29.

In one embodiment, the antibody comprises an Fc region, or a region equivalent to the Fc region of an immunoglobulin. In one embodiment, the antibody comprises an Fc region, particularly an IgG Fc region. In a further embodiment, the antibody is a full-length antibody, particularly an IgG class antibody. In another embodiment, the antibody comprises a human antibody constant region. In one embodiment, the antibody is a human antibody. In one embodiment, the antibody comprises an antibody heavy chain region and/or an antibody light chain region, particularly both a heavy and light chain region, selected from the heavy and light chain region sequences set forth in SEQ ID NO: 59, SEQ ID NO: 60, SEQ ID NO: 61, SEQ ID NO: 62, SEQ ID NO: 65 and SEQ ID NO: 66. In one embodiment, the antibody comprises a light chain region comprising an amino acid sequence of SEQ ID NO: 59 and a heavy chain region comprising an amino acid sequence of SEQ ID NO: 60. In one embodiment, the antibody comprises a light chain region comprising an amino acid sequence of SEQ ID NO: 61 and a heavy chain region comprising an amino acid sequence of SEQ ID NO: 62. In a further embodiment, the antibody is a full-length antibody, comprising an IgG class heavy chain region.

In one embodiment, the antibody of the present invention has an improved affinity. In another embodiment the antibody binds to human TnC with a $K_D$ value of lower than about 1 µM, preferably lower than about 100 nM, more preferably lower than about 10 nM, most preferably lower than about 1 nM. In a particular embodiment the antibody binds to human TnC with a $K_D$ value lower than about 1 nM. In one embodiment, the antibody binds to TnC in human tissues. In a further embodiment the antibody has cross-species reactivity. In one embodiment, said antibody binds to at least one of human, mouse and cynomolgus TnC with a $K_D$ value lower than about 1 µM, preferably lower than about 100 nM, more preferably lower than about 10 nM, most preferably lower than about 2 nM. In a particular embodiment, said antibody binds binds to at least one of human, mouse and cynomolgus TnC with a $K_D$ value lower than about 2 nM. In another particular embodiment, said antibody binds to human TnC with a first $K_D$ value $K_D1$, wherein said antibody binds to mouse TnC with a second $K_D$ value $K_D2$, and wherein said antibody binds to cynomolgus TnC with a third $K_D$ value $K_D3$, wherein all of the $K_D$ values selected from the group consisting of $K_D1$, $K_D2$ and $K_D3$ are lower than about 2 nM. In yet another particular embodiment, said antibody binds binds to human TnC with a first $K_D$ value $K_D1$, wherein said antibody binds to mouse TnC with a second $K_D$ value $K_D2$, and wherein said antibody binds to cynomolgus TnC with a third $K_D$ value $K_D3$, wherein all of the $K_D$ values selected from the group consisting of $K_D1$, $K_D2$ and $K_D3$ are in the range of 2 nM to 0.1 nM. In one embodiment, the antibody is specific for at least one of the TnC domain selected from the group consisting of A1, A2, A3, A4, B, AD1, AD2, C and D. In a particular embodiment, said antibody is specific for the TnC domains A1 and A4. In a particular embodiment, said antibody is specific for the TnC domain C.

In one embodiment, the antibody comprises an Fc region comprising at least one amino acid substitution in the Fc region. In a particular embodiment, the parent non-substituted heavy chain region of said antibody comprises the amino acid residues Leu234, Leu235 and Pro329, wherein the substituted Fc region comprises at least one of the amino acid substitutions selected from the group consisting of Leu234Ala, Leu235Ala and Pro329Gly relative to the parent non-substituted Fc region. In another embodiment, the antibody comprising the substituted Fc region has decreased effector function and/or decreased Fc receptor binding affinity compared to the antibody comprising the parent non-substituted heavy chain region. In one embodiment, the antibody comprises the amino acid substitutions Leu234Ala, Leu235Ala and Pro329Gly relative to the parent non-substituted heavy chain region, wherein binding to FcγR and C1q is abolished and/or wherein Fc-mediated effector function is abolished. In yet another embodiment, said abolished effector function is abolished ADCC. In a particular embodiment, the antibody comprising the substituted Fc region comprises a heavy chain region comprising an amino acid sequence selected from the group of: SEQ ID NO: 65, and SEQ ID NO: 66.

In one embodiment, the antibody is glycoengineered to have modified oligosaccharides in the Fc region. In one embodiment the antibody has an increased proportion of non-fucosylated and/or bisected oligosaccharides in the Fc region, as compared to a non-glycoengineered antibody. In another embodiment, at least about 20% to about 100% of the N-linked oligosaccharides in said Fc region are non-fucosylated. In a further embodiment, said antibody has an increased proportion of bisected oligosaccharides in said Fc region, as compared to a non-glycoengineered antibody. In yet a further embodiment, at least about 20% to about 100% of the N-linked oligosaccharides in said Fc region are bisected. In a specific embodiment at least about 20% to about 50% of the N-linked oligosaccharides in said Fc region are bisected, non-fucosylated. In a further embodiment, the antibody has increased effector function and/or increased Fc receptor binding affinity. In a particular embodiment, the increased effector function is increased antibody-dependent cell-mediated cytotoxicity (ADCC).

In other aspects, the invention is also directed to polypeptides, polynucleotides, host cells, and expression vectors related to the antibodies. In a further aspect, the invention relates to methods of making the antibodies. In a further aspect, the invention is directed to methods of using the antibodies, particularly for the treatment of diseases characterized by expression of TnC, such as cancer.

DETAILED DESCRIPTION OF EMBODIMENTS OF THE INVENTION

I. Definitions

Figure 1:
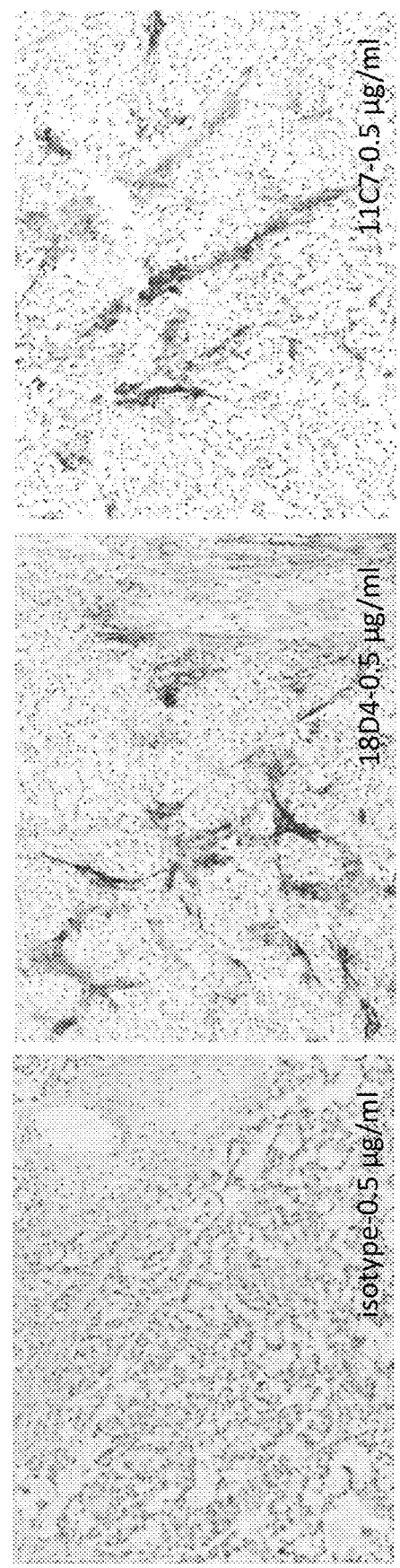
FIG. 1 shows immunohistological staining in LS174T xenografts tumors at 100× magnification as stained with anti-TnC clone 18D4 and anti-TnC clone 11C7. The pattern of staining corresponds to specific TnC stroma fibers. The TnC staining, for both clones 18D4 and 11C7, is overall expressed with moderate intensity. Negative isotype control signal validates the specificity of the technique.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$), which is the ratio of dissociation and association rate constants ($k_{off}$ and $k_{on}$, respectively). Thus, equivalent affinities may comprise different rate constants, as long as the ratio of the rate constants remains the same. Affinity can be measured by common methods known in the art, including those described herein. Specific illustrative and exemplary embodiments for measuring binding affinity are described in the following.

An "affinity matured" antibody refers to an antibody with one or more alterations (e.g., amino acid mutations) in one or more hypervariable regions (HVRs) (e.g., CDRs), compared to a parent antibody which does not possess such alterations, such alterations resulting in an improvement in the affinity of the antibody for antigen. Typically, the affinity matured antibody binds to the same epitope as the parent antibody.

The terms "anti-TnC antibody" and "an antibody that binds to the TnC" refer to an antibody that is capable of binding Tenascin-C (TnC) with sufficient affinity such that the antibody is useful as a diagnostic and/or therapeutic agent in targeting TnC. In one embodiment, the extent of binding of an anti-TnC antibody to an unrelated, non-TnC protein is less than about 10% of the binding of the antibody to TnC as measured, e.g., by a radioimmunoassay (RIA). In certain embodiments, an antibody that binds to TnC has a dissociation constant ($K_D$) of ≤1 µM, ≤100 nM, ≤10 nM, ≤5 nM, ≤2 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M, e.g., from 10 nM to 0.1 nM, e.g., from 5 nM to 0.1 nM, e.g., from 2 nM to 0.1 nM). In certain embodiments, an anti-TnC antibody binds to an epitope of TnC that is conserved among TnC from different species. In certain embodiments, an antibody that binds to an epitope of TnC is specific for at least one of the domains selected from the group consisting of A1, A2, A3, A4, B, AD1, AD2, C and D. In certain embodiments an antibody specific for the TnC A1 and TnC A4 domains is provided. In certain embodiments an antibody specific for the TnC C domain is provided.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. Also included are antibody fragments having an Fc region, and fusion proteins that comprise a region equivalent to the Fc region of an immunoglobulin.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "antigen binding domain" refers to the part of an antigen binding molecule that comprises the area which specifically binds to and is complementary to part or all of an antigen. Where an antigen is large, an antigen binding molecule may only bind to a particular part of the antigen, which part is termed an epitope. An antigen binding domain may be provided by, for example, one or more antibody variable domains (also called antibody variable regions). Preferably, an antigen binding domain comprises an antibody light chain variable region (VL) and an antibody heavy chain variable region (VH).

The term "chimeric" antibody refers to an antibody in which a portion of the heavy and/or light chain is derived from a particular source or species, while the remainder of the heavy and/or light chain is derived from a different source or species. For chimeric antibodies, for example, the non-antigen binding components may be derived from a wide variety of species, including primates such as chimpanzees and humans. Humanized antibodies are a particularly preferred form of chimeric antibodies.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called $\alpha$, $\delta$, $\varepsilon$, $\gamma$, and $\mu$, respectively.

"Cytokine release syndrome", which is an "infusion reaction", is a common immediate complication occurring with the use of antibody infusions. The pathogenesis is characterized in that the antibodies bind to T cell receptors, activating said T cells. The cytokines released by the activated T cells produce a type of systemic inflammatory response similar to that found in severe infection characterised by hypotension, pyrexia and rigors. Deaths due to cytokine release syndrome have been reported, and it can cause life-threatening pulmonary edema if the patient is fluid overloaded.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Cross-species reactivity" refers to the ability of certain antibodies to specifically bind to their respective target antigen wherein said target antigen may derive from different species (e.g., human, mouse, cynomolgus, etc.). A cross-species reactive antibody binds to its respective target antigen derived from at least two different species with a $K_D$ value lower than about 1 μM, preferably lower than about 100 nM, more preferably lower than about 10 nM, more preferably lower than about 5 nM, most preferably lower than about 2 nM. The term "binds to its respective target antigen derived from at least two different species with a $K_D$ value lower than" means that the respective antibody binds to the target antigen deriving from each of the indicated species with a dissociation constant $K_D$ lower than the indicated $K_D$ value. In preferred embodiments a cross-species reactive antibody binds to the target antigen from all indicated species with similar affinity, preferably within a $K_D$ range of 10 nM to 0.1 nM, more preferably 5 nM to 0.1 nM, most preferably 2 nM to 0.1 nM. In some embodiment, similar affinity for the antigen derived from several species, which means binding of the target antigen within a narrow $K_D$ range (e.g., within a range of 10 nM to 0.1 nM or narrower) for all species of interest, is advantageous, e.g., for diagnostic assays or animal models of human diseases. In further preferred embodiment, a cross-species reactive antibody binds to the target antigen from all indicated species (e.g., human, mouse and cynomolgus monkey) with similar affinity, in particular within a $K_D$ range of a factor of 100, within a $K_D$ range of a factor of 50, within a $K_D$ range of a factor of 20, within a $K_D$ range of a factor of 10, within a $K_D$ range of a factor of 5. In a preferred embodiment, a cross-species reactive antibody binds to the target antigen from human, mouse and cynomolgus monkey with similar affinity, in particular within a $K_D$ range of a factor of 10. For clarity, the cross-species reactive antibody binds to one of the indicated species with highest affinity compared to the other indicated species. Accordingly, the cross-species reactive antibody binds to one of the indicated species with lowest affinity compared to the other indicated species Within a $K_D$ range of a defined factor X means that the affinity for the indicated species with. highest affinity is not more than X-times higher than the affinity for the indicated species with lowest affinity. In other words, the $K_D$ value for the indicated species with lowest affinity is not more than X-times the $K_D$ value for the indicated species with highest affinity. It is clear to the field that any method for measuring affinity or avidity can be used to verify that a cross-species reactive antibody binds to the target antigen from all indicated species within a given $K_D$ factor range as described herein as long as the same conditions are applied to the $K_D$ measurement for all indicated species. Preferably, the $K_D$ values are measured using SPR, in particular at 25° C. Preferably, the affinities are measured using the cross-species reactive antibody as Fab fragment.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g., B cell receptor); and B cell activation. As used herein, the terms "reduced" or "increased" in conjunction with effector function refers to a measurable reduction or increase of effector function induced by an antibody of the present invention comprising a modified Fc region compared to effector function induced by the corresponding parent antibody not comprising the modification in the Fc region. Effector function can be measured as disclosed herein and with reference to the examples as disclosed herein. As used herein, the terms "strongly reduced", "abolished" and "residual" in conjunction with effector function are considered to refer to a reduction of the named effector function induced by an antibody of the present invention comprising a modified Fc region compared to effector function induced by the corresponding parent antibody not comprising the modification in the Fc region. "Strongly reduced" means a reduction to 50% or less, "abolished" means a reduction to 10% or less and "residual" means more than 10% compared to the respective effector function induced by the corresponding parent non-modified (e.g., non-substituted) antibody. Accordingly, antibodies of the present invention comprising an Fc variant comprise at least one or more of the following properties: reduced or abolished ADCC, reduced or abolished CDC, reduced or abolished ADCP, reduced or abolished binding to Fc receptors, reduced or abolished binding to C1q and reduced or abolished infusion reaction (cytokine release syndrome).

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

A "region equivalent to the Fc region of an immunoglobulin" is intended to include naturally occurring allelic variants of the Fc region of an immunoglobulin as well as variants having alterations which produce substitutions, additions, or deletions but which do not decrease substantially the ability of the immunoglobulin to mediate effector functions (such as antibody-dependent cellular cytotoxicity). For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie, J. U. et al., Science 247:1306-10 (1990)).

"Framework" or "FR" refers to variable domain residues other than hypervariable region (HVR) (or CDR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody", "intact antibody", and "whole antibody" are used herein interchangeably to refer to an antibody having a structure substantially similar to a native antibody structure or having heavy chains that contain an Fc region as defined herein.

The terms "host cell", "host cell line", and "host cell culture" are used interchangeably and refer to cells into which exogenous nucleic acid has been introduced, including the progeny of such cells. Host cells include "transformants" and "transformed cells", which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. In one embodiment, the host cell is engineered to allow the production of an antibody with modified oligosaccharides. In certain embodiments, the host cells have been further manipulated to express increased levels of one or more polypeptides having β(1,4)-N-acetylglucosaminyltransferase III (GnTIII) activity. Host cells include cultured cells, e.g., mammalian cultured cells, such as CHO cells, BHK cells, NSO cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as complementarity determining regions (CDRs), and these terms are used herein interchangeably in reference to portions of the variable region that form the antigen binding regions. This particular region has been described by Kabat et al., U.S. Dept. of Health and Human Services, "Sequences of Proteins of Immunological Interest" (1983) and by Chothia et al., *J. Mol. Biol.* 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table 1 as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE 1

| CDR Definitions[1] | | | |
|---|---|---|---|
| CDR | Kabat | Chothia | AbM[2] |
| $V_H$ CDR1 | 31-35 | 26-32 | 26-35 |
| $V_H$ CDR2 | 50-65 | 52-58 | 50-58 |
| $V_H$ CDR3 | 95-102 | 95-102 | 95-102 |
| $V_L$ CDR1 | 24-34 | 26-32 | 24-34 |

TABLE 1-continued

| CDR | Kabat | Chothia | AbM[2] |
|---|---|---|---|
| V_L CDR2 | 50-56 | 50-52 | 50-56 |
| V_L CDR3 | 89-97 | 91-96 | 89-97 |

[1]Numbering of all CDR definitions in Table 1 is according to the numbering conventions set forth by Kabat et al. (see below).
[2]"AbM" with a lowercase "b" as used in Table 1 refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

CDRs also comprise "specificity determining residues", or "SDRs", which are residues that contact antigen. SDRs are contained within regions of the CDRs called abbreviated-CDRs, or a-CDRs. In general, only one-fifth to one-third of the residues in a given CDR participate in antigen binding. The specificity-determining residues in a particular CDR can be identified by, for example, computation of interatomic contacts from three-dimensional modeling and determination of the sequence variability at a given residue position in accordance with the methods described in Padlan et al., *FASEB J.* 9(1):133-139 (1995). Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3 (see Almagro and Fransson, *Front. Biosci.* 13:1619-1633 (2008)). Unless otherwise indicated, HVR residues and other residues in the variable domain (e.g., FR residues) are numbered herein according to Kabat et al., supra.

An "antibody conjugate" or "immunoconjugate" is an antibody conjugated to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated antibody" is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848:79-87 (2007).

An "isolated polynucleotide" refers to a polynucleotide molecule that has been separated from a component of its natural environment. An isolated polynucleotide includes a polynucleotide molecule contained in cells that ordinarily contain the polynucleotide molecule, but the polynucleotide molecule is present extrachromosomally or at a chromosomal location that is different from its natural chromosomal location.

"Isolated polynucleotide encoding an anti-TnC antibody" refers to one or more polynucleotide molecules encoding antibody heavy and light chains (or fragments thereof), including such polynucleotide molecule(s) in a single vector or separate vectors, and such polynucleotide molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a constant light (CL) domain, also called a light chain constant region. The light chain of an antibody may be assigned to one of two types, called kappa (κ) and lambda (λ), based on the amino acid sequence of its constant domain.

"No substantial cross-reactivity" means that a molecule (e.g., an antibody) does not recognize or specifically bind an antigen different from the actual target antigen of the molecule (e.g., an antigen closely related to the target antigen), particularly when compared to that target antigen. For example, an antibody may bind less than about 10% to less than about 5% to an antigen different from the actual target antigen, or may bind said antigen different from the actual target antigen at an amount selected from the group consisting of less than about 10%, 9%, 8% 7%, 6%, 5%, 4%, 3%, 2%, 1%, 0.5%, 0.2%, or 0.1%, preferably less than about 2%, 1%, or 0.5%, and most preferably less than about 0.2% or 0.1% antigen different from the actual target antigen.

The term "package insert" is used to refer to instructions customarily included in commercial packages of therapeutic products, that contain information about the indications, usage, dosage, administration, combination therapy, contraindications and/or warnings concerning the use of such therapeutic products.

The term "parent" antibody refers to an antibody that is used as the starting point or basis for the preparation of a variant.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

Similarly, by a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide or polypeptide is at least 80%, 85%, 90%, 95%, 96%, 97%, 98% or 99% identical to a nucleotide sequence or polypeptide sequence of the present invention can be determined conventionally using known computer programs, such as the ones listed above.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "Tenascin-C" or "TnC" as used herein, refers to any native TnC from any vertebrate source, including mammals such as primates (e.g., humans and cynomolgus monkey) and rodents (e.g., mice and rats), unless otherwise indicated. The term encompasses "full-length," unprocessed TnC as well as any form of TnC that results from processing in the cell. The term also encompasses naturally occurring variants of TnC, e.g., splice variants or allelic variants. The amino acid sequence of an exemplary human TnC antigen sequence (with N-terminal GST and 6× His-tag; and C-terminal avi-tag and 6× His-tag) is shown in SEQ ID NO: 4. The amino acid sequence of an exemplary mouse TnC antigen sequence (with N-terminal GST and 6× His-tag; and C-terminal avi-tag and 6× His-tag) is shown in SEQ ID NO: 5. The amino acid sequence of an exemplary cynomolgus TnC antigen sequence (with N-terminal GST and 6× His-tag; and C-terminal avi-tag and 6× His-tag) is shown in SEQ ID NO: 6. In the human TnC molecule, up to nine alternatively spliced fibronectin-type III domains, which may be inserted between the fifth and the sixth of the constant fibronectin-type III domains are known (for a schematic representation of the domain structure of TnC, see e.g., Orend and Chiquet-Ehrismann, Cancer Letters 244, 143-163 (2006). Similarly, in the mouse TnC molecule, six alternatively spliced fibronectin-type III domains are described (e.g.,in Joestner and Faissner, J Biol Chem 274, 17144-17151 (1999)).

As used herein, "treatment" (and grammatical variations thereof such as "treat" or "treating") refers to clinical intervention in an attempt to alter the natural course of disease of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007)). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

As used herein, the term "polypeptide having GnTIII activity" refers to polypeptides that are able to catalyze the addition of a N-acetylglucosamine (GlcNAc) residue in β-1-4 linkage to the β-linked mannoside of the trimannosyl core of N-linked oligosaccharides. This includes fusion polypeptides exhibiting enzymatic activity similar to, but not necessarily identical to, an activity of β(1,4)-N-acetyl-glucosaminyltransferase III, also known as β-1,4-mannosyl-glycoprotein 4-beta-N-acetylglucosaminyl-transferase (EC 2.4.1.144), according to the Nomenclature Committee of the International Union of Biochemistry and Molecular Biology (NC-IUBMB), as measured in a particular biological assay, with or without dose dependency. In the case where dose dependency does exist, it need not be identical to that of GnTIII, but rather substantially similar to the dose-dependence in a given activity as compared to the GnTIII (i.e., the candidate polypeptide will exhibit greater activity or not more than about 25-fold less and, preferably, not more than about tenfold less activity, and most preferably, not more than about three-fold less activity relative to the GnTIII).

As used herein, the term "Golgi localization domain" refers to the amino acid sequence of a Golgi resident polypeptide which is responsible for anchoring the polypeptide to a location within the Golgi complex. Generally, localization domains comprise amino terminal "tails" of an enzyme.

As used herein, the terms "engineer, engineered, engineering," particularly with the prefix "glyco-," as well as the term "glycosylation engineering" are considered to include any manipulation of the glycosylation pattern of a naturally occurring or recombinant polypeptide or fragment thereof. Glycosylation engineering includes metabolic engineering of the glycosylation machinery of a cell, including genetic manipulations of the oligosaccharide synthesis pathways to achieve altered glycosylation of glycoproteins expressed in cells. Furthermore, glycosylation engineering includes the effects of mutations and cell environment on glycosylation. In one embodiment, the glycosylation engineering is an alteration in glycosyltransferase activity. In a particular embodiment, the engineering results in altered glucosaminyltransferase activity and/or fucosyltransferase activity.

As used herein, the term "Fc-mediated cellular cytotoxicity" includes antibody-dependent cell-mediated cytotoxicity (ADCC) and cellular cytotoxicity mediated by a soluble Fc-fusion protein containing a human Fc-region. It is an immune mechanism leading to the lysis of "targeted cells" by "human immune effector cells."

As used herein, the term "human immune effector cells" refers to a population of leukocytes that display Fc receptors on their surfaces, through which they bind to the Fc-region of antibodies or of Fc-fusion proteins and perform effector functions. Such a population may include, but is not limited to, peripheral blood mononuclear cells (PBMC) and/or natural killer (NK) cells.

As used herein, the term "targeted cells" refers to cells to which antigen binding molecules comprising an Fc region (e.g., antibodies or fragments thereof comprising an Fc region) or Fc-fusion proteins specifically bind. The antigen binding molecules or Fc fusion-proteins bind to target cells via the protein part that is N-terminal to the Fc region.

As used herein, the term "increased Fc-mediated cellular cytotoxicity" is defined as either an increase in the number of "targeted cells" that are lysed in a given time, at a given concentration of antibody or of Fc-fusion protein in the medium surrounding the target cells, by the mechanism of Fc-mediated cellular cytotoxicity defined above, and/or a reduction in the concentration of antibody or of Fc-fusion protein, in the medium surrounding the target cells, required to achieve the lysis of a given number of "targeted cells", in a given time, by the mechanism of Fc-mediated cellular cytotoxicity. The increase in Fc-mediated cellular cytotoxicity is relative to the cellular cytotoxicity mediated by the same antigen binding molecule or Fc-fusion protein produced by the same type of host cells, using the same standard production, purification, formulation and storage methods, (which are known to those skilled in the art) but that has not been produced by host cells engineered to have an altered pattern of glycosylation (e.g., to express the glycosyltransferase, GnTIII, or other glycosyltransferases) by the methods described herein.

As used herein, the term "decreased Fc-mediated cellular cytotoxicity" is defined as either an decrease in the number of "targeted cells" that are lysed in a given time, at a given concentration of antibody or of Fc-fusion protein in the medium surrounding the target cells, by the mechanism of Fc-mediated cellular cytotoxicity defined above, and/or an increase in the concentration of antibody or of Fc-fusion protein, in the medium surrounding the target cells, required to achieve the lysis of a given number of "targeted cells", in a given time, by the mechanism of Fc-mediated cellular cytotoxicity. The decrease in Fc-mediated cellular cytotoxicity is relative to the cellular cytotoxicity mediated by the same antigen binding molecule or Fc-fusion protein produced by the same type of host cells, using the same standard production, purification, formulation and storage methods, (which are known to those skilled in the art) but that has not been modified by amino acid substitution in the Fc region of the antibody.

Antibodies having increased or decreased antibody dependent cell-mediated cytotoxicity (ADCC), as that term is defined herein, induce increased or decreased ADCC as determined by any suitable method known to those of ordinary skill in the art. One accepted in vitro ADCC assay is as follows:

1) the assay uses target cells that are known to express the target antigen recognized by the antigen-binding region of the antibody;

2) the assay uses human peripheral blood mononuclear cells (PBMCs), isolated from blood of a randomly chosen healthy donor, as effector cells;
3) the assay is carried out according to following protocol:
  i) the PBMCs are isolated using standard density centrifugation procedures and are suspended at $5\times10^6$ cells/ml in RPMI cell culture medium;
  ii) the target cells are grown by standard tissue culture methods, harvested from the exponential growth phase with a viability higher than 90%, washed in RPMI cell culture medium, labeled with 100 micro-Curies of $^{51}$Cr, washed twice with cell culture medium, and resuspended in cell culture medium at a density of $10^5$ cells/ml;
  iii) 100 microliters of the final target cell suspension above are transferred to each well of a 96-well microtiter plate;
  iv) the antibody is serially-diluted from 4000 ng/ml to 0.04 ng/ml in cell culture medium and 50 microliters of the resulting antibody solutions are added to the target cells in the 96-well microtiter plate, testing in triplicate various antibody concentrations covering the whole concentration range above;
  v) for the maximum release (MR) controls, 3 additional wells in the plate containing the labeled target cells, receive 50 microliters of a 2% (V/V) aqueous solution of non-ionic detergent (Nonidet, Sigma, St. Louis), instead of the antibody solution (point iv above);
  vi) for the spontaneous release (SR) controls, 3 additional wells in the plate containing the labeled target cells, receive 50 microliters of RPMI cell culture medium instead of the antibody solution (point iv above);
  vii) the 96-well microtiter plate is then centrifuged at 50×g for 1 minute and incubated for 1 hour at 4° C.;
  viii) 50 microliters of the PBMC suspension (point i above) are added to each well to yield an effector:target cell ratio of 25:1 and the plates are placed in an incubator under 5% CO2 atmosphere at 37° C. for 4 hours;
  ix) the cell-free supernatant from each well is harvested and the experimentally released radioactivity (ER) is quantified using a gamma counter;
  x) the percentage of specific lysis is calculated for each antibody concentration according to the formula (ER-MR)/(MR-SR)×100, where ER is the average radioactivity quantified (see point ix above) for that antibody concentration, MR is the average radioactivity quantified (see point ix above) for the MR controls (see point v above), and SR is the average radioactivity quantified (see point ix above) for the SR controls (see point vi above);
4) "increased ADCC" is defined as either an increase in the maximum percentage of specific lysis observed within the antibody concentration range tested above, and/or a reduction in the concentration of antibody required to achieve one half of the maximum percentage of specific lysis observed within the antibody concentration range tested above. The increase in ADCC is relative to the ADCC, measured with the above assay, mediated by the same antibody, produced by the same type of host cells, using the same standard production, purification, formulation and storage methods, which are known to those skilled in the art, but that has not been produced by host cells engineered to overexpress GnTIII. "Decreased ADCC" is defined as either a decrease in the maximum percentage of specific lysis observed within the antibody concentration range tested above, and/or an increase in the concentration of antibody required to achieve one half of the maximum percentage of specific lysis observed within the antibody concentration range tested above. The decrease in ADCC is relative to the ADCC, measured with the above assay, mediated by the same antibody, produced by the same type of host cells, using the same standard production, purification, formulation and storage methods, which are known to those skilled in the art, but that has not been modified by amino acid substitution in the Fc region of the antibody.

II. Compositions and Methods

Distinct alternatively spliced isoforms of Tenascin-C (TnC), are specifically expressed in certain pathological conditions but essentially absent from healthy adult tissues, thus antibodies targeting TnC have great therapeutic potential. The present invention provides antibodies that bind to TnC, in particular antibodies with high affinity and good cross-species reactivity. Antibodies of the invention are useful, e.g., for the diagnosis or treatment of diseases characterized by expression of TnC, such as cancer.

The present invention provides for antibodies that specifically bind to TnC. Particularly, the present invention provides for antibodies that specifically bind TnC, wherein said antibodies have improved affinity and/or cross-species reactivity.

In one embodiment, an anti-TnC antibody of the invention comprises at least one (e.g., one, two, three, four, five, or six) heavy or light chain complementarity determining region (CDR) selected from the group consisting of SEQ ID NO: 37, SEQ ID NO: 38, SEQ ID NO: 39, SEQ ID NO: 40, SEQ ID NO: 41, SEQ ID NO: 42, SEQ ID NO: 49, SEQ ID NO: 50, SEQ ID NO: 51, SEQ ID NO: 52, SEQ ID NO: 53 and SEQ ID NO: 54, or a variant or truncated form thereof containing at least the specificity-determining residues (SDRs) for said CDR.

In one embodiment, an antibody of the invention comprises at least one, at least two, or all three heavy chain CDR (HCDR) sequences selected from (a) HCDR1 comprising an amino acid sequence selected from the group consisting of SEQ ID NO: 49 and SEQ ID NO: 52; (b) HCDR2 comprising an amino acid sequence selected from the group consisting of SEQ ID NO: 50 and SEQ ID NO: 53; and (c) HCDR3 comprising an amino acid sequence selected from the group consisting of SEQ ID NO: 51 and SEQ ID NO: 54. In a further embodiment, the antibody comprises a heavy chain variable region comprising (a) a heavy chain CDR1 selected from the group consisting of SEQ ID NO: 49 and SEQ ID NO: 52; (b) a heavy chain CDR2 selected from the group consisting of SEQ ID NO: 50 and SEQ ID NO: 53; and (c) a heavy chain CDR3 selected from the group consisting of SEQ ID NO: 51 and SEQ ID NO: 54, or variants or truncated forms thereof containing at least the SDRs for said CDRs.

In one embodiment, an antibody of the invention comprises at least one, at least two, or all three light chain CDR (LCDR) sequences selected from (a) LCDR1 comprising an amino acid sequence selected from the group consisting of SEQ ID NO: 37 and SEQ ID NO: 40; (b) LCDR2 comprising an amino acid sequence selected from the group consisting of SEQ ID NO: 38 and SEQ ID NO: 41; and (c) LCDR3 comprising an amino acid sequence selected from the group consisting of SEQ ID NO: 39 and SEQ ID NO: 42. In a further embodiment, the antibody comprises a light chain variable region comprising (a) a light chain CDR1 selected from the group consisting of SEQ ID NO: 37 and SEQ ID NO: 40 (b) a light chain CDR2 selected from the group consisting of SEQ ID NO: 38 and SEQ ID NO: 41; and (c) a light chain CDR3 selected from the group consisting of SEQ ID NO: 39 and SEQ ID NO: 42, or variants or truncated forms thereof containing at least the SDRs for said CDRs.

In one embodiment, an antibody of the invention comprises a heavy chain variable region comprising a heavy chain CDR1 selected from the group consisting of SEQ ID NO: 49 and SEQ ID NO: 52; a heavy chain CDR2 selected from the group consisting of SEQ ID NO: 50 and SEQ ID NO: 53; and a heavy chain CDR3 selected from the group consisting of SEQ ID NO: 51 and SEQ ID NO: 54, and a light chain variable region comprising a light chain CDR1 selected from the group consisting of SEQ ID NO: 37 and SEQ ID NO: 40; a light chain CDR2 selected from the group consisting of SEQ ID NO: 38 and SEQ ID NO: 41; and a light chain CDR3 selected from the group consisting of SEQ ID NO: 39 and SEQ ID NO: 42, or variants or truncated forms thereof containing at least the SDRs for said CDRs.

In yet another specific embodiment, an antibody of the invention comprises a heavy chain variable region comprising the heavy chain CDR1 of SEQ ID NO: 49; the heavy chain CDR2 of SEQ ID NO: 50; and the heavy chain CDR3 of SEQ ID NO: 51, and a light chain variable region comprising the light chain CDR1 of SEQ ID NO: 37; the light chain CDR2 of SEQ ID NO: 38; and the light chain CDR3 of SEQ ID NO: 39.

In yet another specific embodiment, an antibody of the invention comprises a heavy chain variable region comprising the heavy chain CDR1 of SEQ ID NO: 52; the heavy chain CDR2 of SEQ ID NO: 53; and the heavy chain CDR3 of SEQ ID NO: 54, and a light chain variable region comprising the light chain CDR1 of SEQ ID NO: 40, the light chain CDR2 of SEQ ID NO: 41; and the light chain CDR3 of SEQ ID NO: 42.

In one embodiment, an antibody of the invention comprises a heavy chain variable region (VH) comprising an amino acid sequence having at least about 90%, 91%, 92%, 93%, 94%, 95%, 96%, 97%, 98% or 99% identity to a sequence selected from the group consisting of SEQ ID NO: 28 and SEQ ID NO: 30. In one embodiment, the antibody comprises a heavy chain variable region comprising an amino acid sequence selected from the group consisting of: SEQ ID NO: 28 and SEQ ID NO: 30.

In certain embodiments, a VH sequence having at least 90%, 91%, 92%, 93%, 94%, 95%, 96%, 97%, 98% or 99% identity contains substitutions (e.g., conservative substitutions), insertions, or deletions relative to the reference sequence, but an anti-TnC antibody comprising that sequence retains the ability to bind to TnC. In certain embodiments, a total of 1 to 10 amino acids have been substituted, inserted and/or deleted in SEQ ID NO: 28 or SEQ ID NO: 30. In certain embodiments, substitutions, insertions, or deletions occur in regions outside the HVRs or CDRs (i.e., in the FRs). Optionally, an anti-TnC antibody according to the invention comprises the VH sequence in SEQ ID NO: 28 or SEQ ID NO: 30, including post-translational modifications of that sequence. In a particular embodiment, the VH comprises one, two or three heavy chain CDRs selected from the sequences set forth in SEQ ID NO: 49, SEQ ID NO: 50, SEQ ID NO: 51, SEQ ID NO: 52, SEQ ID NO: 53 and SEQ ID NO: 54 for the HCDR1, HCDR2 and HCDR3.

In another embodiment, an antibody of the invention comprises a light chain variable region comprising an amino acid sequence having at least about 90%, 91%, 92%, 93%, 94%, 95%, 96%, 97%, 98% or 99% identity to a sequence selected from the group consisting of SEQ ID NO: 27 and SEQ ID NO: 29. In yet another embodiment, the antibody comprises a light chain variable region comprising an amino acid sequence selected from the group consisting of: SEQ ID NO: 27 and SEQ ID NO: 29.

In certain embodiments, a VL sequence having at least 90%, 91%, 92%, 93%, 94%, 95%, 96%, 97%, 98% or 99% identity contains substitutions (e.g., conservative substitutions), insertions, or deletions relative to the reference sequence, but an anti-TnC antibody comprising that sequence retains the ability to bind to TnC. In certain embodiments, a total of 1 to 10 amino acids have been substituted, inserted and/or deleted in SEQ ID NO: 27 or SEQ ID NO: 29. In certain embodiments, the substitutions, insertions, or deletions occur in regions outside the HVRs or CDRs (i.e., in the FRs). Optionally, an anti-TnC antibody of the invention comprises the VL sequence in SEQ ID NO: 27 or SEQ ID NO: 29, including post-translational modifications of that sequence. In a particular embodiment, the VL comprises one, two or three light chain CDRs selected from sequences set forth in SEQ ID NO: 37, SEQ ID NO: 38, SEQ ID NO: 39, SEQ ID NO: 40, SEQ ID NO: 41 and SEQ ID NO: 42 for the LCDR1, LCDR2 and LCDR3.

In another aspect, an anti-TnC antibody is provided, wherein the antibody comprises a VH as in any of the embodiments provided above, and a VL as in any of the embodiments provided above. In one embodiment, the antibody comprises a heavy chain variable region comprising an amino acid sequence that is at least about 90%, 91%, 92%, 93%, 94%, 95%, 96%, 97%, 98%, 99% or 100% identical to a sequence selected from the group of: SEQ ID NO: 28 and SEQ ID NO: 30, and a light chain variable region comprising an amino acid sequence that is at least about 90%, 91%, 92%, 93%, 94%, 95%, 96%, 97%, 98%, 99% or 100% identical to a sequence selected from the group of: SEQ ID NO: 27 and SEQ ID NO: 29. In one embodiment, the antibody comprises the VH and VL sequences in SEQ ID NO: 28 or SEQ ID NO: 30 and SEQ ID NO: 27 or SEQ ID NO: 29, respectively, including post-translational modifications of those sequences.

In a specific embodiment, an antibody of the invention comprises a heavy chain variable region comprising the amino acid sequence of SEQ ID NO: 28 and a light chain variable region comprising the amino acid sequence of SEQ ID NO: 27. In a specific embodiment, an antibody of the invention comprises a heavy chain variable region comprising the amino acid sequence of SEQ ID NO: 30 and a light chain variable region comprising the amino acid sequence of SEQ ID NO: 29. In a particular embodiment, the antibody according to any of the above embodiments additionally comprises an Fc region or a region equivalent to the Fc region of an immunoglobulin. In one embodiment an antibody of the invention comprises an Fc region, particularly a IgG Fc region, most particularly a IgG1 Fc region. In a particular embodiment, the antibody of the invention is a full length antibody, particularly an IgG class antibody, most particularly an IgG1 isotype antibody. In another embodiment, the antibody of the invention is an antibody fragment, selected from the group of: an scFv fragment, an Fv fragment, a Fab fragment, and a F(ab') 2 fragment. In a further embodiment, the antibody of the invention is an antibody fragment having an Fc region, or a fusion protein that comprises a region equivalent to the Fc region of an immunoglobulin. In one embodiment, the antibody of the invention is a monoclonal antibody. In one embodiment, an antibody of the invention is chimeric, more specifically humanized. In a particular embodiment, an antibody of the invention is human. In another embodiment, an antibody of the invention comprises a human constant region. In one embodiment the antibody of the invention comprises a human Fc region, preferably a human IgG Fc region, most particularly a human IgG1 Fc region.

In one embodiment, an antibody of the invention comprises a heavy chain constant region, wherein said heavy chain constant region is a human IgG constant region, particularly a human IgG1 constant region, comprising an Fc region. In one embodiment, an antibody of the invention comprises a heavy chain region, wherein said heavy chain region is a human IgG heavy chain region, particularly a human IgG1 heavy chain region, comprising an Fc region. In a specific embodiment, the antibody comprises a heavy chain region comprising an amino acid sequence selected from the group consisting of: SEQ ID NO: 60, SEQ ID NO: 62, SEQ ID NO: 65, and SEQ ID NO: 66. In another specific embodiment an antibody of the invention comprises a light chain region comprising an amino acid sequence selected from the group consisting of: SEQ ID NO: 59 and SEQ ID NO: 61. In yet another specific embodiment, an antibody of the invention comprises a heavy chain region comprising the amino acid sequence of SEQ ID NO: 60, and a light chain region comprising the amino acid sequence of SEQ ID NO: 59. In yet another specific embodiment, an antibody of the invention comprises a heavy chain region comprising the amino acid sequence of SEQ ID NO: 62, and a light chain region comprising the amino acid sequence of SEQ ID NO: 61.

In a particular embodiment, the invention provides an antibody that specifically binds to TnC, wherein said antibody comprises a) a heavy chain region comprising an amino acid sequence that is at least about 90%, 91%, 92%, 93%, 94%, 95%, 96%, 97%, 98%, 99% or 100% identical to a sequence selected from the group consisting of: SEQ ID NO: 60 and SEQ ID NO: 62, or a light chain region comprising an amino acid sequence that is at least about 90%, 91%, 92%, 93%, 94%, 95%, 96%, 97%, 98%, 99% or 100% identical to a sequence selected from the group consisting of SEQ ID NO: 59 and SEQ ID NO: 61, or a combination thereof, comprising an Fc region or a region equivalent to the Fc region of an immunoglobulin.

In one embodiment, an antibody of the invention is provided, wherein said antibody has an improved affinity. In one embodiment, an antibody of the invention binds to Tenascin-C (TnC) with a dissociation constant ($K_D$) value lower than about 1 μM to about 0.001 nM, particularly a $K_D$ value lower than about 100 nM, lower than about 10 nM, or lower than about 1 nM. In a specific embodiment, an antibody of the invention binds to human Tenascin-C (TnC) with a dissociation constant ($K_D$) value lower than about 1 nM. In one embodiment, an antibody of the invention binds to human, mouse, and cynomolgus TnC. In one embodiment, an antibody of the invention has cross-species reactivity. In another specific embodiment of the invention binds to the C domain of human, mouse, and cynomolgus TnC. In one embodiment the antibody of the invention has cross-species reactivity. In one embodiment the antibody of the present invention binds to at least one of human, mouse and cynomolgus TnC with a $K_D$ value lower than about 100 nM, lower than about 10 nM, lower than about 5 nM or lower than 2 nM. In a specific embodiment the antibody of the present invention binds to at least one of human, mouse and cynomolgus TnC with a $K_D$ value lower than about 2 nM. In further embodiments, the antibody of the present invention binds to human TnC with a first $K_D$ value $K_D1$, wherein said antibody binds to mouse TnC with a second $K_D$ value $K_D2$, and wherein said antibody binds to cynomolgus TnC with a third $K_D$ value $K_D3$, wherein all of the $K_D$ values selected from the group consisting of $K_D1$, $K_D2$ and $K_D3$ are lower than about 10 nM, lower than about 5 nM or lower than about 2 nM. In yet further embodiments, the antibody of the present invention binds to human TnC with a first $K_D$ value $K_D1$, wherein said antibody binds to mouse TnC with a second $K_D$ value $K_D2$, and wherein said antibody binds to cynomolgus TnC with a third $K_D$ value $K_D3$, wherein all of the $K_D$ values selected from the group consisting of $K_D1$, $K_D2$ and $K_D3$ are in the range of 10 nM to 0.1 nM, in the range of 5 nM to 0.1 nM or in the range of 2 nM to 0.1 nM. In a further embodiment, the antibody of the present invention binds to human TnC with a first $K_D$ value $K_D1$, wherein said antibody binds to mouse TnC with a second $K_D$ value $K_D2$, and wherein said antibody binds to cynomolgus TnC with a third $K_D$ value $K_D3$, wherein all of the $K_D$ values selected from the group consisting of $K_D1$, $K_D2$ and $K_D3$ are within a $K_D$ range of a factor of 20. In a further embodiment, the antibody of the present invention binds to human TnC with a first $K_D$ value $K_D1$, wherein said antibody binds to mouse TnC with a second $K_D$ value $K_D2$, and wherein said antibody binds to cynomolgus TnC with a third $K_D$ value $K_D3$, wherein all of the $K_D$ values selected from the group consisting of $K_D1$, $K_D2$ and $K_D3$ are within a $K_D$ range of a factor of 10. In one embodiment an antibody of the invention is specific for at least one of the TnC domain selected from the group consisting of A1, A2, A3, A4, B, AD1, AD2, C and D. In one embodiment, an antibody is provided, wherein said antibody is able to bind to at least one of the TnC domain selected from the group consisting of A1, A4 and C. In one embodiment, an antibody of the invention is specific for the TnC domains A1 and A4. In one embodiment, an antibody of the invention is specific for the TnC domain C. In a specific embodiment, an antibody of the invention binds to the A1 and to the A4 domain of human, mouse, and cynomolgus TnC. In another specific embodiment, an antibody of the invention binds to the C domain of human, mouse, and cynomolgus TnC. In one embodiment the antibody of the invention has cross-species reactivity. In a more specific embodiment, an antibody of the invention binds to the A1 domain of human, mouse and cynomolgus TnC A1 and to the A4 domain of human, mouse and cynomolgus TnC A4 with a $K_D$ value lower than about 100 nM, lower than about 10 nM, lower than about 5 nM or lower than about 2 nM. $K_D$ values are determined by Surface Plasmon Resonance, using the antibodies as Fab or IgG. In one embodiment, an anti-TnC antibody of the invention binds TnC in human tissues.

In one embodiment, an antibody of the invention comprises an Fc region, wherein said antibody comprises at least one amino acid substitution in the Fc region. In one embodiment, an antibody of the invention comprising at least one amino acid substitution in the Fc region has decreased effector function and/or decreased Fc receptor binding affinity compared to an antibody comprising the parent non-substituted Fc region. In a specific embodiment said parent non-substituted Fc region comprises the amino acid residues Leu234, Leu235 and Pro329, wherein the substituted Fc region comprises at least one of the amino acid substitutions selected from the group consisting of Leu234Ala, Leu235Ala and Pro329Gly relative to the parent non-substituted Fc region. In a particular embodiment, the invention provides an antibody that specifically binds to TnC, wherein said antibody comprises a) a heavy chain region comprising an amino acid sequence that is at least about 90%, 91%, 92%, 93%, 94%, 95%, 96%, 97%, 98%, 99% or 100% identical to a sequence selected from the group consisting of SEQ ID NO: 65 and SEQ ID NO: 66, and a light chain region comprising an amino acid sequence that is at least about 90%, 91%, 92%, 93%, 94%, 95%, 96%, 97%, 98%, 99% or 100% identical to a sequence selected from the group consisting of SEQ ID NO: 59 and SEQ ID NO: 61. In a specific embodiment, antibodies of the invention comprise a heavy chain region comprising an amino acid sequence selected from the group of: SEQ ID NO: 65, and SEQ ID NO: 66. In a further embodiment antibody comprising the substituted Fc region has decreased effector function and/or decreased Fc receptor binding affinity compared to the antibody comprising the parent non-substituted heavy chain region. In a further specific embodiment, the antibody of the invention, comprising said substituted Fc region, comprises the amino acid substitutions Leu234Ala, Leu235Ala and Pro329Gly relative to the parent non-substituted Fc region, wherein binding to FcγR and C1q is abolished and/or wherein Fc-mediated effector function is abolished. In one embodiment, an antibody of the invention has decreased effector function and/or decreased Fc receptor binding affinity. In one embodiment, the decreased effector function and/or decreased Fc receptor binding is a result of amino acid substitutions in the Fc region of the antibody. The decreased effector function can include, but is not limited to, one or more of the following: decreased Fc-mediated cellular cytotoxicity (including decreased antibody-dependent cell-mediated cytotoxicity (ADCC)), decreased antibody-dependent cellular phagocytosis (ADCP), decreased cytokine secretion, decreased immune-complex-mediated antigen uptake by antigen-presenting cells, decreased binding to NK cells, decreased binding to macrophages, decreased binding to monocytes, decreased binding to polymorphonuclear cells, decreased dendritic cell maturation, or decreased T cell priming. In a particular embodiment, the decreased effector function is decreased ADCC. In another particular embodiment, the decreased effector function is abolished ADCC. The decreased Fc receptor binding preferably is decreased binding to an activating Fc receptor, most preferably FcγRIIIa. In one embodiment, an antibody of the invention does not cause a clinically significant level of toxicity when administered to an individual in a therapeutically effective amount.

In a particular embodiment, the invention provides an antibody that specifically binds to TnC, wherein said antibody comprises a) a heavy chain variable region comprising an amino acid sequence that is at least about 90%, 91%, 92%, 93%, 94%, 95%, 96%, 97%, 98%, 99% or 100% identical to a sequence selected from the group consisting of SEQ ID NO: 28 and SEQ ID NO: 30, or a light chain variable region comprising an amino acid sequence that is at least about 90%, 91%, 92%, 93%, 94%, 95%, 96%, 97%, 98%, 99% or 100% identical to a sequence selected from the group consisting of SEQ ID NO: 27 and SEQ ID NO: 29, or a combination thereof, and b) an Fc region or a region equivalent to the Fc region of an immunoglobulin. In one embodiment, an antibody of the invention comprises an Fc region, wherein said Fc region is a glycoengineered Fc region. In a further embodiment, an antibody of the invention is glycoengineered to have modified oligosaccharides in the Fc region. In a specific embodiment, the antibody has an increased proportion of bisected oligosaccharides in the Fc region, compared to a non-glycoengineered antibody. In a more specific embodiment, at least about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, preferably at least about 50%, more preferably at least about 70%, of the N-linked oligosaccharides in the Fc region of the antibody are bisected. The bisected oligosaccharides may be of the hybrid or complex type. In another specific embodiment, an antibody of the invention has an increased proportion of non-fucosylated oligosaccharides in the Fc region, compared to a non-glycoengineered antibody. In a more specific embodiment, at least about 20%, about 25%, about 30%, about 35%, about 40%, about 45%, about 50%, about 55%, about 60%, about 65%, about 70%, about 75%, about 80%, about 85%, about 90%, about 95%, or about 100%, preferably at least about 50%, more preferably at least about 70%, of the N-linked oligosaccharides in the Fc region of the antibody are non-fucosylated. The non-fucosylated oligosaccharides may be of the hybrid or complex type. In a particular embodiment, an antibody of the invention has an increased proportion of bisected, non-fucosylated oligosaccharides in the Fc region, compared to a non-glycoengineered antibody. Specifically, the antibody comprises an Fc region in which at least about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, preferably at least about 15%, more preferably at least about 25%, at least about 35% or at least about 50%, of the N-linked oligosaccharides are bisected, non-fucosylated. The bisected, non-fucosylated oligosaccharides may be of the hybrid or complex type. In one embodiment, an antibody of the invention has increased effector function and/or increased Fc receptor binding affinity. Increased effector function and/or increased Fc receptor binding can result e.g.,from glycoengineering and/or affinity maturation of antibodies. In one embodiment, the increased effector function and/or increased Fc receptor binding is a result of glycoengineering of the Fc region of the antibody. In another embodiment, the increased effector function and/or increased Fc receptor binding is a result of a combination of increased affinity and glycoengineering. The increased effector function can include, but is not limited to, one or more of the following: increased Fc-mediated cellular cytotoxicity (including increased antibody-dependent cell-mediated cytotoxicity (ADCC)), increased antibody-dependent cellular phagocytosis (ADCP), increased cytokine secretion, increased immune-complex-mediated antigen uptake by antigen-presenting cells, increased binding to NK cells, increased binding to macrophages, increased binding to monocytes, increased binding to polymorphonuclear cells, increased direct signaling inducing apoptosis, increased crosslinking of target-bound antibodies, increased dendritic cell maturation, or increased T cell priming. In a particular embodiment, the increased effector function is increased ADCC. The increased Fc receptor binding preferably is increased binding to an activating Fc receptor, most preferably FcγRIIIa. In one embodiment, an antibody of the invention does not cause a clinically significant level of toxicity when administered to an individual in a therapeutically effective amount.

In a particular embodiment, the invention provides an antibody that specifically binds to the A1 and A4 domain of TnC, wherein said antibody comprises a heavy chain variable region comprising the amino acid sequence SEQ ID NO: 28, a light chain variable region comprising the amino acid sequence SEQ ID NO: 27, and a human IgG Fc region.

In a particular embodiment, the invention provides an antibody that specifically binds to the C domain of TnC, wherein said antibody comprises a heavy chain variable region comprising the amino acid sequence SEQ ID NO: 30, a light chain variable region comprising the amino acid sequence SEQ ID NO: 29, and a human IgG Fc region.

In a particular embodiment, the invention provides an antibody that specifically binds to the A1 and A4 domain of TnC, wherein said antibody comprises a heavy chain variable region comprising the amino acid sequence SEQ ID NO: 28, a light chain variable region comprising the amino acid sequence SEQ ID NO: 27, and a human IgG Fc region, and wherein said antibody is glycoengineered to have increased effector function and/or Fc receptor binding affinity.

In a particular embodiment, the invention provides an antibody that specifically binds to the C domain of TnC, wherein said antibody comprises a heavy chain variable region comprising the amino acid sequence SEQ ID NO: 30, a light chain variable region comprising the amino acid sequence SEQ ID NO: 29, and a human IgG Fc region, and wherein said antibody is glycoengineered to have increased effector function and/or Fc receptor binding affinity.

In a particular embodiment, the invention provides an antibody that specifically binds to the A1 and A4 domain of TnC, wherein said antibody comprises a heavy chain variable region comprising the amino acid sequence SEQ ID NO: 28, a light chain variable region comprising the amino acid sequence SEQ ID NO: 27, and a human IgG Fc region, wherein said antibody comprises at least one amino acid substitution in the Fc region, wherein the parent non-substituted Fc region comprises the amino acid residues Leu234, Leu235 and Pro329, wherein the substituted Fc region comprises at least one of the amino acid substitutions selected from the group consisting of Leu234Ala, Leu235Ala and Pro329Gly relative to the parent non-substituted Fc region, wherein the antibody comprising the substituted Fc region has decreased effector function and/or decreased Fc receptor binding affinity compared to the antibody comprising the parent non-substituted Fc region.

In a particular embodiment, the invention provides an antibody that specifically binds to the C domain of TnC, wherein said antibody comprises a heavy chain variable region comprising the amino acid sequence SEQ ID NO: 30, a light chain variable region comprising the amino acid sequence SEQ ID NO: 29, and a human IgG Fc region, wherein said antibody comprises at least one amino acid substitution in the Fc region, wherein the parent non-substituted Fc region comprises the amino acid residues Leu234, Leu235 and Pro329, wherein the substituted Fc region comprises at least one of the amino acid substitutions selected from the group consisting of Leu234Ala, Leu235Ala and Pro329Gly relative to the parent non-substituted Fc region, wherein the antibody comprising the substituted Fc region has decreased effector function and/or decreased Fc receptor binding affinity compared to the antibody comprising the parent non-substituted Fc region.

In a particular embodiment, the invention provides an antibody that specifically binds to the A1 and A4 domain of TnC, wherein said antibody comprises a heavy chain variable region comprising
(a) the heavy chain CDR1 of SEQ ID NO: 49;
(b) the heavy chain CDR2 of SEQ ID NO: 50;
(c) the heavy chain CDR3 of SEQ ID NO: 51,
and a light chain variable region comprising
(a) the light chain CDR1 of SEQ ID NO: 37;
(b) the light chain CDR2 of SEQ ID NO: 38, and
(c) the light chain CDR3 of SEQ ID NO: 39.

In a particular embodiment, the invention provides an antibody that specifically binds to the C domain of TnC, wherein said antibody comprises a heavy chain variable region comprising
(a) the heavy chain CDR1 of SEQ ID NO: 52;
(b) the heavy chain CDR2 of SEQ ID NO: 53;
(c) the heavy chain CDR3 of SEQ ID NO: 54,
and a light chain variable region comprising
(a) the light chain CDR1 of SEQ ID NO: 40;
(b) the light chain CDR2 of SEQ ID NO: 41, and
(c) the light chain CDR3 of SEQ ID NO: 42.

In a particular embodiment, the invention provides an antibody that specifically binds to the A1 and A4 domain of TnC, wherein said antibody comprises a heavy chain region comprising the amino acid sequence SEQ ID NO: 60, and a light chain region comprising the amino acid sequence SEQ ID NO: 59.

In a particular embodiment, the invention provides an antibody that specifically binds to the A1 and A4 domain of human, mounse and cynomolgus TnC, wherein said antibody comprises a heavy chain variable region comprising the amino acid sequence SEQ ID NO: 28, a light chain variable region comprising the amino acid sequence SEQ ID NO: 27, and a human IgG Fc region. In a particular embodiment, the invention provides an antibody that specifically binds to the C domain of TnC, wherein said antibody comprises a heavy chain region comprising the amino acid sequence SEQ ID NO: 62, and a light chain region comprising an amino acid sequence selected from the group of SEQ ID NO: 61.

In a particular embodiment, the invention provides an antibody that specifically binds to the C domain of human, mouse and cynomolgus TnC, wherein said antibody comprises a heavy chain variable region comprising the amino acid sequence SEQ ID NO: 30, a light chain variable region comprising the amino acid sequence SEQ ID NO: 29, and a human IgG Fc region.

In another particular embodiment, the invention provides an antibody that specifically binds to the A1 and A4 domain of TnC, wherein said antibody comprises a heavy chain variable region comprising the amino acid sequence SEQ ID NO: 28, a light chain variable region comprising the amino acid sequence SEQ ID NO: 27, and a human IgG Fc region, and wherein said antibody has an increased proportion of non-fucosylated oligosaccharides and/or an increased proportion of bisected oligosaccharides in said Fc region. In another particular embodiment, the invention provides an antibody that specifically binds to the C domain of TnC, wherein said antibody comprises a heavy chain variable region comprising the amino acid sequence SEQ ID NO: 30, a light chain variable region comprising the amino acid sequence SEQ ID NO: 29, and a human IgG Fc region, and wherein said antibody has an increased proportion of non-fucosylated oligosaccharides and/or an increased proportion of bisected oligosaccharides in said Fc region.

In one aspect, the invention provides for an antibody that specifically binds to TnC, wherein said antibody comprises at least one amino acid substitution in at least one heavy or light chain CDR of the parent antibody. For example, the antibody may comprise at least one, e.g., from about one to about ten (i.e., about 1, 2, 3, 4, 5, 6, 7, 8, 9, or 10), and particularly from about two to about five, substitutions in one or more hypervariable regions or CDRs (i.e., 1, 2, 3, 4, 5, or 6 hypervariable regions or CDRs) of the parent antibody.

Additionally, the antibody may also comprise one or more additions, deletions and/or substitutions in one or more framework regions of either the heavy or the light chain, compared to the parent antibody. In one embodiment, said at least one amino acid substitution in at least one CDR contributes to increased binding affinity of the antibody compared to its parent antibody. In another embodiment said antibody has at least about 2-fold to about 10-fold greater affinity for TnC than the parent antibody (when comparing the antibody of the invention and the parent antibody in the same format, e.g., the Fab format). Further, the antibody derived from a parent antibody may incorporate any of the features, singly or in combination, described in the preceding paragraphs in relation to the antibodies of the invention.

The present invention also provides for polynucleotides encoding antibodies that specifically bind to TnC. In one aspect, the invention is directed to an isolated polynucleotide encoding a polypeptide that forms part of an anti-TnC antibody according to the invention as described hereinbefore. In one embodiment, the isolated polynucleotide encodes an antibody heavy chain and/or an antibody light chain that forms part of an anti-TnC antibody according to the invention as described hereinbefore.

In one embodiment, the invention is directed to an isolated polynucleotide comprising a sequence encoding one or more (e.g., one, two, three, four, five, or six) of the heavy or light chain complementarity determining regions (CDRs) set forth in SEQ ID NO: 37, SEQ ID NO: 38, SEQ ID NO: 39, SEQ ID NO: 40, SEQ ID NO: 41, SEQ ID NO: 42, SEQ ID NO: 49, SEQ ID NO: 50, SEQ ID NO: 51, SEQ ID NO: 52, SEQ ID NO: 53 and SEQ ID NO: 54, or a variant or truncated form thereof containing at least the specificity-determining residues (SDRs) for said CDR. In another embodiment, the polynucleotide comprises a sequence that encodes three heavy chain CDRs (e.g., HCDR1, HCDR2, and HCDR3) or three light chain CDRs (e.g., LCDR1, LCDR2, and LCDR3) selected from SEQ ID NO: 37, SEQ ID NO: 38, SEQ ID NO: 39, SEQ ID NO: 40, SEQ ID NO: 41, SEQ ID NO: 42, SEQ ID NO: 49, SEQ ID NO: 50, SEQ ID NO: 51, SEQ ID NO: 52, SEQ ID NO: 53 and SEQ ID NO: 54, or variants or truncated forms thereof containing at least the SDRs for each of said three complementarity determining regions. In yet another embodiment, the polynucleotide comprises a sequence encoding three heavy chain CDRs (e.g., HCDR1, HCDR2, and HCDR3) and three light chain CDRs (e.g., LCDR1, LCDR2, and LCDR3) selected from SEQ ID NO: 37, SEQ ID NO: 38, SEQ ID NO: 39, SEQ ID NO: 40, SEQ ID NO: 41, SEQ ID NO: 42, SEQ ID NO: 49, SEQ ID NO: 50, SEQ ID NO: 51, SEQ ID NO: 52, SEQ ID NO: 53 and SEQ ID NO: 54. In a particular embodiment the polynucleotide encoding one or more CDRs comprises a sequence that is at least about 90%, 95%, 96%, 97%, 98%, 99%, or 100% identical to one or more of the CDR nucleotide sequences of SEQ ID NO: 31, SEQ ID NO: 32, SEQ ID NO: 33, SEQ ID NO: 34, SEQ ID NO: 35, SEQ ID NO: 36, SEQ ID NO: 43, SEQ ID NO: 44, SEQ ID NO: 45, SEQ ID NO: 46, SEQ ID NO: 47 and SEQ ID NO: 48.

In a further embodiment, the polynucleotide comprises a sequence encoding a heavy chain variable region selected from the group of SEQ ID NO: 28 and SEQ ID NO: 30, and/or a sequence encoding a light chain variable region selected from the group of SEQ ID NO: 27 and SEQ ID NO: 29. In a particular embodiment, the polynucleotide encoding a heavy chain and/or light chain variable region comprises a sequence selected from the group of variable region nucleotide sequences consisting of SEQ ID NO: 23, SEQ ID NO: 24, SEQ ID NO: 25 and SEQ ID NO: 26, or a combination thereof.

In a specific embodiment, the polynucleotide comprises a sequence encoding a heavy chain variable region selected from the group of SEQ ID NO: 28 and SEQ ID NO: 30, and a sequence encoding a heavy chain constant region, particularly a human heavy chain constant region. In a particular embodiment, said heavy chain constant region is a human IgG heavy chain constant region, specifically a human IgG1 heavy chain constant region, comprising an Fc region. In another specific embodiment, the polynucleotide comprises a sequence encoding a light chain variable region selected from the group of SEQ ID NO: 27 and SEQ ID NO: 29, and a sequence encoding a light chain constant region, particularly a human light chain constant region.

In one embodiment, the invention is directed to a composition that comprises a first isolated polynucleotide encoding a polypeptide comprising an amino acid sequence that is at least about 90%, 95%, 96%, 97%, 98%, 99%, or 100% identical to a sequence selected from the group consisting of SEQ ID NO: 59 and SEQ ID NO: 61, and a second isolated polynucleotide encoding a polypeptide comprising an amino acid sequence that is at least about 90%, 95%, 96%, 97%, 98%, 99%, or 100% identical to a sequence selected from the group consisting of SEQ ID NO: 60, and SEQ ID NO: 62.

In one embodiment, the invention is directed to a composition that comprises a first isolated polynucleotide comprising a sequence that is at least about 90%, 95%, 96%, 97%, 98%, 99%, or 100% identical to a sequence selected from the group consisting of SEQ ID NO: 59 and SEQ ID NO: 61, and a second isolated polynucleotide comprising a sequence that is at least about 90%, 95%, 96%, 97%, 98%, 99%, or 100% identical to a sequence selected from the group consisting of SEQ ID NO: 65, and SEQ ID NO: 66.

In a further aspect, the invention is also directed to isolated polypeptides, encoded by any of the polynucleotides according the invention as described hereinbefore.

In a further aspect, an anti-TnC antibody according to any of the above embodiments may incorporate any of the features, singly or in combination, as described in Sections 1-7 below:

1. Antibody Affinity

In certain embodiments, an antibody provided herein has a dissociation constant ($K_D$) of ≤1 µM, ≤100 nM, ≤10 nM, ≤5 nM, ≤2 nM, ≤1 nM, ≤0.1 nM, ≤0.01 nM, or ≤0.001 nM (e.g., $10^{-8}$M or less, e.g., from $10^{-8}$M to $10^{-13}$M, e.g., from $10^{-9}$M to $10^{-13}$ M). In one embodiment, $K_D$ is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599

(1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, $K_D$ is measured using surface plasmon resonance assays using a BIACORE®-2000 or a BIACORE®-3000 (BlAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant ($K_D$) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, N.Y.), pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g., *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA*, 89:4285 (1992); and Presta et al. *J. Immunol.*, 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMAB® technology; U.S. Pat. No. 7,041,870 describing K-M MOUSE® technology, and U.S. Patent Application Publication No. US 2007/0061900, describing VELOCI-MOUSE® technology. Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., N.Y., 1987); and Boerner et al., *J. Immunol.,* 147: 86 (1991)). Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g., a bispecific antibody. Multispecific antibodies are monoclonal antibodies that have binding specificities for at least two different sites. In certain embodiments, one of the binding specificities is for TnC and the other is for any other antigen. In certain embodiments, bispecific antibodies may bind to two different epitopes of TnC. Bispecific antibodies may also be used to localize cytotoxic agents to cells which express TnC. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, Nature 305: 537 (1983)), WO 93/08829, and Traunecker et al., EMBO J. 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (sFv) dimers (see, e.g., Gruber et al., J. Immunol., 152:5368 (1994)); and preparing trispecific antibodies as described, e.g., in Tutt et al. J. Immunol. 147: 60 (1991).

Engineered antibodies with three or more functional antigen binding sites, including "Octopus antibodies," are also included herein (see, e.g., US 2006/0025576A1).

The antibody or fragment herein also includes a "Dual Acting FAb" or "DAF" comprising an antigen binding site that binds to TnC as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 2 under the heading of "conservative substitutions." More substantial changes are provided in Table 2 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 2

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be generated, e.g., using phage display-based affinity maturation techniques such as those described herein. Briefly, one or more HVR residues are mutated and the variant antibodies displayed on phage and screened for a particular biological activity (e.g., binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex may be used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

b) Glycosylation Variants

In some embodiments, modifications of the oligosaccharides in an antibody of the invention may be made in order to create antibody variants with certain improved properties. In one aspect, the present invention provides glycoforms of anti-TnC antibodies having increased effector function, including antibody-dependent cellular cytotoxicity. Glycosylation engineering of antibodies has been previously described. See, e.g., U.S. Pat. No. 6,602,684, incorporated herein by reference in its entirety. Methods of producing anti-TnC antibodies from host cells that have altered activity of genes involved in glyocsylation are also described herein in detail (see, e.g., section entitled "Recombinant Methods and Compositions" below).

Antibodies are provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umaña et al.); and US 2005/0123546 (Umaña et al.).

In one embodiment, the anti-TnC antibodies of the invention have an increased proportion of bisected oligosaccharides in the Fc region as a result of the modification of their oligosaccharides by the methods of the present invention. In one embodiment, the percentage of bisected N-linked oligosaccharides in the Fc region of the anti-TnC antibodies of the invention is at least about 10% to about 100%, specifically at least about 50%, more specifically, at least about 60%, at least about 70%, at least about 80%, or at least about 90-95% of the total oligosaccharides. The bisected oligosaccharides may be of the hybrid or complex type.

In another embodiment, the anti-TnC antibodies of the invention have an increased proportion of nonfucosylated oligosaccharides in the Fc region as a result of the modification of their oligosaccharides by the methods of the present invention. In one embodiment, the percentage of nonfucosylated oligosaccharides is at least about 20% to about 100%, specifically at least about 50%, at least about 60% to about 70%, and more specifically, at least about 75%. The nonfucosylated oligosaccharides may be of the hybrid or complex type.

The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described for example in WO 2008/077546. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. The relative amount of fucose is the percentage of fucose-containing structures related to all glycostructures identified in an N-Glycosidase F treated sample (e.g., complex, hybrid and high mannose structures) by MALDI-TOF MS. Such fucosylation variants may have improved ADCC function.

The glycoengineering methodology that can be used with the anti-TnC antibodies of the present invention has been described in greater detail in U.S. Pat. No. 6,602,684, U.S. Pat. Appl. Publ. No. 2004/0241817 A1, U.S. Pat. Appl. Publ. No. 2003/0175884 A1, Provisional U.S. Patent Application No. 60/441,307 and WO 2004/065540, the entire contents of each of which is incorporated herein by reference in its entirety. The anti-TnC antibodies of the present invention can alternatively be glycoengineered to have reduced fucose residues in the Fc region according to the techniques disclosed in U.S. Pat. Appl. Pub. No. 2003/0157108 (Genentech), or in EP 1 176 195 A1, WO 03/084570, WO 03/085119 and U.S. Pat. Appl. Pub. Nos. 2003/0115614, 2004/093621, 2004/110282, 2004/110704, 2004/132140, Niwa et al., J Immunol Methods 306, 151/160 (2006), U.S. Pat. No. 6,946,292 (Kyowa). Glycoengineered anti-TnC antibodies of the invention may also be produced in expression systems that produce modified glycoproteins, such as those taught in U.S. Pat. Appl. Pub. No. 60/344,169 and WO 03/056914 (GlycoFi, Inc.) or in WO 2004/057002 and WO 2004/024927 (Greenovation).

Further examples of publications related to "defucosylated" or "fucose-deficient" antibody variants include: WO 2000/61739; WO 2001/29246; US 2002/0164328; US 2004/0109865; WO 2005/035586; WO 2005/035778; WO2005/053742; WO2002/031140; Okazaki et al. J. Mol. Biol. 336:1239-1249 (2004); Yamane-Ohnuki et al. Biotech. Bioeng. 87: 614 (2004). Examples of cell lines capable of producing defucosylated antibodies include Lec13 CHO cells deficient in protein fucosylation (Ripka et al. Arch. Biochem. Biophys. 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

In certain embodiments, an antibody provided herein is altered to increase or decrease the extent to which the antibody is glycosylated. Addition or deletion of glycosylation sites to an antibody may be accomplished by altering the amino acid sequence such that one or more glycosylation sites is created or removed.

Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

Increases in ADCC or other effector functions of the anti-TnC antibodies of the present invention can also achieved by increasing affinity of the antigen binding molecule for TnC, for example by affinity maturation or other methods of improving affinity (see Tang et al., *J. Immunol.* 2007, 179:2815-2823), or by amino acid modifications in the Fc region as described below. Combinations of these approaches are also encompassed by the present invention.

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g., a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described herein and in U.S. Pat. No. 5,500,362 (see, e.g., Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821, 337 (see Bruggemann, M. et al., *J. Exp. Med.* 166:1351-1361 (1987)). Alternatively, non-radioactive methods may be employed (see, for example, ACTI™ non-radioactive cytotoxicity assay for flow cytometry (CellTechnology, Inc. Mountain View, Calif.); and CytoTox 96® non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

In one aspect, the Fc domain of the antibody of the invention comprises one or more amino acid mutation that reduces the binding affinity of the Fc domain to an Fc receptor and/or effector function. Typically, the same one or more amino acid mutation is present in each of the two subunits of the Fc domain. In particular, the Fc domain comprises at least one amino acid substitution at a position of E233, L234, L235, N297, P331 and P329 (EU numbering). In particular, the Fc domain comprises amino acid substitutions at positions 234 and 235 (EU numbering) and/or 329 (EU numbering) of the IgG heavy chains. More particularly, provided is an antibody according to the invention which comprises an Fc domain with the amino acid substitutions L234A, L235A and P329G ("P329G LALA", EU numbering) in the IgG heavy chains. The amino acid substitutions L234A and L235A refer to the so-called LALA mutation. The "P329G LALA" combination of amino acid substitutions almost completely abolishes Fcγ receptor binding of a human IgG1 Fc domain and is described in International Patent Appl. Publ. No. WO 2012/130831 A1 which also describes methods of preparing such mutant Fc domains and methods for determining its properties such as Fc receptor binding or effector functions.

Fc domains with reduced Fc receptor binding and/or effector function also include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

In another aspect, the Fc domain is an IgG4 Fc domain. IgG4 antibodies exhibit reduced binding affinity to Fc receptors and reduced effector functions as compared to IgG1 antibodies. In a more specific aspect, the Fc domain is an IgG4 Fc domain comprising an amino acid substitution at position S228 (Kabat numbering), particularly the amino acid substitution S228P. In a more specific aspect, the Fc domain is an IgG4 Fc domain comprising amino acid substitutions L235E and S228P and P329G (EU numbering). Such IgG4 Fc domain mutants and their Fcγ receptor binding properties are also described in WO 2012/130831.

Further antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).) In certain embodiments, an antibody variant comprises an Fc region with one or more amino acid substitutions which improve ADCC, e.g., substitutions at positions 298, 333, and/or 334 of the Fc region (EU numbering of residues). In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Effector function of an Fc domain, or antibodies of the invention comprising an Fc domain, can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assay methods may be employed (see, for example, ACTI™ non-radioactive cytotoxicity assay for flow cytometry (CellTechnology, Inc. Mountain View, Calif.); and CytoTox 96® non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al., Proc Natl Acad Sci USA 95, 652-656 (1998).

In some aspects, binding of the Fc domain to a complement component, specifically to C1q, is reduced. Accordingly, in some embodiments wherein the Fc domain is engineered to have reduced effector function, said reduced effector function includes reduced CDC. C1q binding assays may be carried out to determine whether the antibodies of the invention is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.*

24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

For further examples concerning Fc region variants see also U.S. Pat. Appl. Nos. 60/439,498; 60/456,041; 60/514,549; or WO 2004/063351 (variant Fc regions with increased binding affinity due to amino acid modification); or U.S. patent application Ser. No. 10/672,280 or WO 2004/099249 (Fc variants with altered binding to FcγR due to amino acid modification), Duncan & Winter, Nature 322:738-40 (1988); U.S. Pat. Nos. 5,648,260; 5,624,821; and WO 94/29351.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Nall. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Recombinant Methods and Compositions

Antibodies may be produced using recombinant methods and compositions, e.g., as described in U.S. Pat. No. 4,816,567. In one embodiment, isolated polynucleotide encoding an anti-TnC antibody described herein is provided. Such polynucleotide may encode an amino acid sequence comprising the VL and/or an amino acid sequence comprising the VH of the antibody (e.g., the light and/or heavy chains of the antibody). In a further embodiment, one or more vectors (e.g., cloning vectors or expression vectors) comprising such polynucleotide are provided. In a further embodiment, a host cell comprising such polynucleotide or such vector is provided. In one such embodiment, a host cell comprises (e.g., has been transformed with): (1) a vector comprising a polynucleotide that encodes an amino acid sequence comprising the VL of the antibody and an amino acid sequence comprising the VH of the antibody (e.g., a polycistronic vector), or (2) a first vector comprising a polynucleotide that encodes an amino acid sequence comprising the VL of the antibody and a second vector comprising a polynucleotide that encodes an amino acid sequence comprising the VH of the antibody. In one embodiment, the host cell is a eukaryotic cell, particularly a mammalian cell, e.g., a Chinese Hamster Ovary (CHO), a baby hamster kidney (BHK) cell or lymphoid cell (e.g., Y0, NS0, Sp20 cell). In one embodiment, a method of making an anti-TnC antibody is provided, wherein the method comprises culturing a host cell comprising a polynucleotide encoding the antibody, as provided above, under conditions suitable for expression of the antibody, and optionally recovering the antibody from the host cell (or host cell culture medium).

For recombinant production of an anti-TnC antibody, one or more polynucleotide(s) encoding an antibody, e.g., as described above, are isolated and inserted into one or more vectors for further cloning and/or expression in a host cell. Methods which are well known to those skilled in the art can be used to construct expression vectors containing the coding sequence of an anti-TnC antibody along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989) and Ausubel et al., CURRENT PROTOCOLS IN MOLECULAR BIOLOGY, Greene Publishing Associates and Wiley Interscience, N.Y (1989).

In one embodiment, one or several polynucleotides encoding an anti-TnC antibody may be expressed under the control of a constitutive promoter or, alternatively, a regulated expression system. Suitable regulated expression systems include, but are not limited to, a tetracycline-regulated expression system, an ecdysone-inducible expression system, a lac-switch expression system, a glucocorticoid-inducible expression system, a temperature-inducible promoter system, and a metallothionein metal-inducible expression system. If several different polynucleotides encoding an antibody of the present invention are comprised within the host cell system, some of them may be expressed under the control of a constitutive promoter, while others are expressed under the control of a regulated promoter.

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in E. coli.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22:1409-1414 (2004), and Li et al., Nat. Biotech. 24:210-215 (2006). Such expression systems are also taught in U.S. Pat. Appl. No. 60/344,169 and WO 03/056914 (methods for producing human-like glycoprotein in a non-human eukaryotic host cell).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells. Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK); buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR$^-$CHO cells (Urlaub et al., Proc. Natl. Acad. Sci. USA 77:4216 (1980)); and myeloma cell lines such as YO, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

Stable expression is generally preferred to transient expression because it typically achieves more reproducible results and also is more amenable to large-scale production; however, it is within the skill of one in the art to determine whether transient expression is better for a particular situation.

The present invention is also directed to a method for producing an anti-TnC antibody, comprising (a) culturing a host cell comprising at least one polynucleotide encoding an anti-TnC antibody according to the present invention in a medium under conditions allowing the expression of the antibody; and (b) recovering the antibody.

The present invention is further directed to a method for modifying the glycosylation profile of the anti-TnC antibodies of the present invention that are produced by a host cell, comprising expressing in said host cell one or more polynucleotide(s) encoding an anti-TnC antibody and one or more polynucleotide(s) encoding a polypeptide with a glycosyltransferase activity, or a vector comprising such polynucleotides. Generally, any type of cultured cell line, including the cell lines discussed above, can be used to generate cell lines for the production of anti-TnC antibodies with altered glycosylation pattern. Preferred cell lines include CHO cells, BHK cells, NS0 cells, SP2/0 cells, YO myeloma cells, P3X63 mouse myeloma cells, PER cells, PER.C6 cells or hybridoma cells, and other mammalian cells. Polypeptides with glycosyltransferase activity include β(1,4)-N-acetylglucosaminyltransferase III (GnTIII), α-mannosidase II (ManII), β(1,4)-galactosyltransferase (GalT), β(1,2)-N-acetylglucosaminyltransferase I (GnTI), and β(1,2)-N-acetylglucosaminyltransferase II (GnTII). In one embodiment, a combination of polynucleotides encoding for polynucleotides with glycosyltransferase activity are expressed in the host cell (e.g., GnTIII and Man II). Likewise, the method also encompasses expression of one or more polynucleotide(s) encoding the anti-TnC antibody in a host cell in which a glycosyltransferase gene has been disrupted or otherwise deactivated (e.g., a host cell in which the activity of the gene encoding α1,6 core fucosyltransferase has been knocked out). In a particular embodiment, the anti-TnC antibodies of the present invention can be produced in a host cell that further expresses a polynucleotide encoding a polypeptide having GnTIII activity to modify the glycosylation pattern of said antibodies. In a specific embodiment, the polypeptide having GnTIII activity is a fusion polypeptide comprising the Golgi localization domain of a Golgi resident polypeptide. In another particular embodiment, the expression of the anti-TnC antibody of the present invention in a host cell that expresses a polynucleotide encoding a polypeptide having GnTIII activity results in anti-TnC antibodies with increased Fc receptor binding affinity and/or increased effector function. Accordingly, in one embodiment, the present invention is directed to a host cell comprising (a) one or more isolated polynucleotide(s) comprising a sequence encoding a polypeptide having GnTIII activity; and (b) one or more isolated polynucleotide(s) encoding an anti-TnC antibody of the present invention. In a particular embodiment, the polypeptide having GnTIII activity is a fusion polypeptide comprising the catalytic domain of GnTIII and the Golgi localization domain of a heterologous Golgi resident polypeptide. Particularly, said Golgi localization domain is the Golgi localization domain of mannosidase II. Methods for generating such fusion polypeptides and using them to produce antibodies with increased effector functions are disclosed in WO2004/065540, U.S. Provisional Pat. Appl. No. 60/495,142 and U.S. Pat. Appl. Publ. No. 2004/0241817, the entire contents of which are expressly incorporated herein by reference. In another embodiment, the host cell additionally comprises an isolated polynucleotide comprising a sequence encoding a polypeptide having mannosidase II (ManII) activity. The polynucleotide(s) encoding polypeptide(s), like the polynucleotide(s) encoding the anti-TnC antibody, may be expressed under the control of a constitutive promoter or, alternately, a regulated expression system. Such systems are well known in the art, and include the systems discussed above.

The host cells which contain the coding sequence of the anti-TnC antibody and/or the coding sequence of polypeptides having glycosyltransferase activity, and which express the biologically active gene products may be identified e.g., by DNA-DNA or DNA-RNA hybridization; the presence or absence of "marker" gene functions; assessing the level of transcription as measured by the expression of the respective mRNA transcripts in the host cell; or detection of the gene product as measured by immunoassay or by its biological activity—methods which are well known in the art. GnTIII or Man II activity can be detected e.g., by employing a lectin which binds to biosynthesis products of GnTIII or ManII, respectively. An example for such a lectin is the $E_4$-PHA lectin which binds preferentially to oligosaccharides containing bisecting GlcNAc. Biosynthesis products (i.e., specific oligosaccharide structures) of polypeptides having GnTIII or ManII activity can also be detected by mass spectrometric analysis of oligosaccharides released from glycoproteins produced by cells expressing said polypeptides. Alternatively, a functional assay which measures the increased Fc receptor binding or increased effector function mediated by antibodies produced by the cells engineered with the polynucleotide encoding a polypeptide having GnTIII activity may be used.

The present invention is also directed to a method for producing an anti-TnC antibody having modified oligosaccharides, comprising (a) culturing a host cell engineered to express at least one polynucleotide encoding a polypeptide having glycosyltransferase activity under conditions which permit the production of an anti-TnC antibody according to the present invention, wherein said polypeptide having glycosyltransferase activity is expressed in an amount sufficient to modify the oligosaccharides in the Fc region of said anti-TnC antibody produced by said host cell; and (b) isolating said anti-TnC antibody. In one embodiment, the polypeptide having glycosyltransferase activity is GnTIII. In another embodiment, there are two polypeptides having glycosyltransferase activity. In a particular embodiment, the two peptides having glycosyltransferase activity are GnTIII and ManII. In another embodiment, the polypeptide having glycosyltransferase activity is a fusion polypeptide comprising the catalytic domain of GnTIII. In a more specific embodiment, the fusion polypeptide further comprises the Golgi localization domain of a Golgi resident polypeptide. Particularly, the Golgi localization domain is the localization domain of mannosidase II or GnTI, most particularly the localization domain of mannosidase II. Alternatively, the Golgi localization domain is selected from the group consisting of: the localization domain of mannosidase I, the localization domain of GnTII, and the localization domain of α1,6 core fucosyltransferase.

In a particular embodiment, the modified anti-TnC antibody produced by the host cell or method described above has an IgG constant region or a fragment thereof comprising the Fc region. In another particular embodiment the anti-TnC antibody is a humanized or human antibody or a fragment thereof comprising an Fc region.

The anti-TnC antibody with altered glycosylation produced by the host cell or method described above typically exhibit increased Fc receptor binding affinity and/or increased effector function as a result of the modification of the host cell (e.g., by expression of a glycosyltransferase gene). Preferably, the increased Fc receptor binding affinity is increased binding to an activating Fcy receptor, most preferably the FcγRIIIa receptor. The increased effector function is preferably an increase in one or more of the following: increased antibody-dependent cellular cytotoxicity, increased antibody-dependent cellular phagocytosis (ADCP), increased cytokine secretion, increased immune-complex-mediated antigen uptake by antigen-presenting cells, increased Fc-mediated cellular cytotoxicity, increased binding to NK cells, increased binding to macrophages, increased binding to polymorphonuclear cells (PMNCs), increased binding to monocytes, increased crosslinking of target-bound antibodies, increased direct signaling inducing apoptosis, increased dendritic cell maturation, and increased T cell priming.

Assays

Anti-TnC antibodies provided herein may be identified, screened for, or characterized for their physical/chemical properties and/or biological activities by various assays known in the art.

a) Binding Assays and Other Assays

In one aspect, an antibody of the invention is tested for its antigen binding activity, e.g., by known methods such as ELISA, Western blot, etc.

In another aspect, competition assays may be used to identify an antibody that competes with other anti-TnC antibodies for binding to TnC. In certain embodiments, such a competing antibody binds to the same epitope (e.g., a linear or a conformational epitope) that is bound by said other specific anti-TnC antibody. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized TnC is incubated in a solution comprising a first labeled antibody that binds to TnC (e.g., the 18D4 antibody described in the Examples) and a second unlabeled antibody that is being tested for its ability to compete with the first antibody for binding to TnC. The second antibody may be present in a hybridoma supernatant. As a control, immobilized TnC is incubated in a solution comprising the first labeled antibody but not the second unlabeled antibody. After incubation under conditions permissive for binding of the first antibody to TnC, excess unbound antibody is removed, and the amount of label associated with immobilized TnC is measured. If the amount of label associated with immobilized TnC is substantially reduced in the test sample relative to the control sample, then that indicates that the second antibody is competing with the first antibody for binding to TnC. See Harlow and Lane (1988) *Antibodies: A Laboratory Manual* ch. 14 (Cold Spring Harbor Laboratory, Cold Spring Harbor, N.Y.).

b) Activity Assays

In one aspect, assays are provided for identifying anti-TnC antibodies thereof having biological activity. Biological activity may include, e.g., lysis of targeted cells, antibody-dependent cell-mediated cytotoxicity (ADCC), complement-dependent cytotoxicity (CDC), or induction of apoptosis. Antibodies having such biological activity in vivo and/or in vitro are also provided.

In certain embodiments, an antibody of the invention is tested for such biological activity. Exemplary assays for testing ADCC are described hereinbefore (see under "Definitions": "antibody having increased ADCC"). Assays for detecting cell lysis (e.g., by measurement of LDH release) or apoptosis (e.g., using the TUNEL assay) are well known in the art. Assays for measuring ADCC or CDC are also described in WO 2004/065540 (see Example 1 therein), the entire content of which is incorporated herein by reference.

Immunoconjugates

The invention also provides immunoconjugates comprising an anti-TnC antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., Cancer Res. 53:3336-3342 (1993); and Lode et al., Cancer Res. 58:2925-2928 (1998)); an anthracycline such as daunomycin or doxorubicin (see Kratz et al., Current Med. Chem. 13:477-523 (2006); Jeffrey et al., Bioorganic & Med. Chem. Letters 16:358-362 (2006); Torgov et al., Bioconj. Chem. 16:717-721 (2005); Nagy et al., Proc. Natl. Acad. Sci. USA 97:829-834 (2000); Dubowchik et al., Bioorg. & Med. Chem. Letters 12:1529-1532 (2002); King et al., J. Med. Chem. 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), Momordica charantia inhibitor, curcin, crotin, Sapaonaria officinalis inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $^{211}$At, $^{131}$I, $^{125}$I, $^{90}$Y, $^{186}$Re, $^{188}$Re, $^{153}$Sm, $^{212}$Bi, $^{32}$P, $^{212}$Pb and radioactive isotopes of Lu. When the radioconjugate is used for detection, it may comprise a radioactive atom for scintigraphic studies, for example $^{99m}$Tc or $^{123}$I, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

Methods and Compositions for Diagnostics and Detection

In certain embodiments, any of the anti-TnC antibodies provided herein is useful for detecting the presence of TnC in a biological sample. The term "detecting" as used herein encompasses quantitative or qualitative detection. In certain embodiments, a biological sample comprises a cell or tissue, such as cells or tissues from brain, breast, colon, kidney, liver, lung, ovary, pancreas, prostate, skeletal muscle, skin, small intestine, stomach or uterus, including also cells or tissues tumors of these organs.

In one embodiment, an anti-TnC antibody for use in a method of diagnosis or detection is provided. In a further aspect, a method of detecting the presence of TnC in a biological sample is provided. In certain embodiments, the method comprises contacting the biological sample with an anti-TnC antibody as described herein under conditions permissive for binding of the anti-TnC antibody to TnC, and detecting whether a complex is formed between the anti-TnC antibody and TnC. Such method may be an in vitro or in vivo method. In one embodiment, an anti-TnC antibody is used to select subjects eligible for therapy with an anti-TnC antibody, e.g., where TnC is a biomarker for selection of patients.

In certain embodiments, labeled anti-TnC antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Pharmaceutical Formulations

Pharmaceutical formulations of an anti-TnC antibody as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. For example, if the disease to be treated is cancer, it may be desirable to further provide one or more anti-cancer agents, e.g., a chemotherapeutic agent, an inhibitor of tumor cell proliferation, or an activator of tumor cell apoptosis. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g., films, or microcapsules.

The formulations to be used for in vivo administration are generally sterile. Sterility may be readily accomplished, e.g., by filtration through sterile filtration membranes.

The molecules described herein may be in a variety of dosage forms which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application, but will typically be injectable or infusible solutions.

Therapeutic Methods and Compositions

Any of the anti-TnC antibodies or pharmaceutical formulations comprising the anti-TnC antibodies provided herein may be used in therapeutic methods.

The anti-TnC antibodies provided herein can be used for treating diseases characterized by TnC expression, particularly by abnormal expression (e.g., overexpression, or expression in a different pattern in the cell) of TnC compared to normal tissue of the same cell type. TnC is abnormally expressed (e.g., overexpressed) in many human tumors compared to non-tumor tissue of the same cell type. Thus, the anti-TnC antibodies provided herein are particularly useful in the prevention of tumor formation, eradication of tumors and inhibition of tumor growth or metastasis. The anti-TnC antibodies provided herein can be used to treat any tumor expressing TnC. Particular malignancies that can be treated by the anti-TnC antibodies provided herein include, for example, lung cancer, colon cancer, gastric cancer, breast cancer, head and neck cancer, skin cancer, liver cancer, kidney cancer, prostate cancer, pancreatic cancer, brain cancer, cancer of the skeletal muscle.

The anti-TnC antibodies disclosed herein can be used to inhibit tumor growth or kill tumor cells. For example, the anti-TnC antibodies can bind to TnC that is on the membrane or cell surface of cancerous cells (tumor cells or cells of the tumor stroma) and elicit, e.g., ADCC or other effector mediated killing of the cancerous cells.

The anti-TnC antibodies can alternatively be used in order to block the function of TnC, particularly by physically interfering with its binding of another compound. For example, the antigen binding molecules can be used to block TnC mediated cell adhesion, spreading or migration.

In one aspect, an anti-TnC antibody for use as a medicament is provided. In further aspects, an anti-TnC antibody for use in treating a disease characterized by expression of TnC is provided. In certain embodiments, an anti-TnC antibody for use in a method of treatment is provided. In certain embodiments, the invention provides an anti-TnC antibody for use in a method of treating an individual having a disease characterized by expression of TnC, comprising administering to the individual an effective amount of the anti-TnC antibody. In one such embodiment, the method further comprises administering to the individual an effective amount of at least one additional therapeutic agent, e.g., as described below. In further embodiments, the invention provides an anti-TnC antibody for use in inducing lysis of a cell. In certain embodiments, the invention provides an anti-TnC antibody for use in a method of inducing lysis of a cell in an individual comprising administering to the individual an effective amount of the anti TnC antibody to induce lysis of a cell. An "individual" according to any of the above embodiments is preferably a human. A "disease characterized by expression of TnC" according to any of the above embodiments is preferably cancer, most preferably a cancer selected from the group of lung cancer, colon cancer, gastric cancer, breast cancer, head and neck cancer, skin cancer, liver cancer, kidney cancer, prostate cancer, pancreatic cancer, brain cancer, cancer of the skeletal muscle. A "cell" according to any of the above embodiments is preferably a cell present in a tumor, such as a tumor cell or a cell of the tumor stroma, most preferably a tumor cell. "TnC expression" according to any of the above embodiments preferably is abnormal expression, such as overexpression or expression in a different pattern in the cell, compared to normal tissue of the same cell type.

In a further aspect, the invention provides for the use of an anti-TnC antibody in the manufacture or preparation of a medicament. In one embodiment, the medicament is for treatment of a disease characterized by expression of TnC. In a further embodiment, the medicament is for use in a method of treating a disease characterized by expression of TnC comprising administering to an individual having a disease characterized by expression of TnC an effective amount of the medicament. In one such embodiment, the method further comprises administering to the individual an effective amount of at least one additional therapeutic agent, e.g., as described below. In a further embodiment, the medicament is for inducing lysis of a cell. In a further embodiment, the medicament is for use in a method of inducing lysis of a cell in an individual comprising administering to the individual an amount effective of the medicament to inducing lysis of a cell. An "individual" according to any of the above embodiments is preferably a human. A "disease characterized by expression of TnC" according to any of the above embodiments is preferably cancer, most preferably a cancer selected from the group of lung cancer, colon cancer, gastric cancer, breast cancer, skin cancer, liver cancer, kidney cancer, prostate cancer, pancreatic cancer, brain cancer, cancer of the skeletal muscle. A "cell" according to any of the above embodiments is preferably a cell present in a tumor, such as a tumor cell or a cell of the tumor stroma, most preferably a tumor cell. "TnC expression" according to any of the above embodiments preferably is abnormal expression, such as overexpression or expression in a different pattern in the cell, compared to normal tissue of the same cell type.

In a further aspect, the invention provides a method for treating a disease characterized by expression of TnC. In one embodiment, the method comprises administering to an individual having such disease characterized by expression of TnC an effective amount of an anti-TnC antibody. In one such embodiment, the method further comprises administering to the individual an effective amount of at least one additional therapeutic agent, as described below. In a further embodiment, the invention provides a method for inducing lysis of a cell in an individual. In one embodiment, the method comprises administering to the individual an effective amount of an anti-TnC antibody to induce lysis of a cell. An "individual" according to any of the above embodiments may be a human. A "disease characterized by expression of TnC" according to any of the above embodiments is preferably cancer, most preferably a cancer selected from the group of lung cancer, colon cancer, gastric cancer, breast cancer, skin cancer, liver cancer, kidney cancer, prostate cancer, pancreatic cancer, brain cancer, cancer of the skeletal muscle. A "cell" according to any of the above embodiments is preferably a cell present in a tumor, such as a tumor cell or a cell of the tumor stroma, most preferably a tumor cell. "TnC expression" according to any of the above embodiments preferably is abnormal expression, such as overexpression or expression in a different pattern in the cell, compared to normal tissue of the same cell type.

In a further aspect, the invention provides pharmaceutical formulations comprising any of the anti-TnC antibodies provided herein, e.g., for use in any of the above therapeutic methods. In one embodiment, a pharmaceutical formulation comprises any of the anti-TnC antibodies provided herein and one or more pharmaceutically acceptable carrier. In another embodiment, a pharmaceutical formulation comprises any of the anti-TnC antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent. In certain embodiments, an additional therapeutic agent is an anti-cancer agent. Suitable anti-cancer agents are e.g., a chemotherapeutic agent, an inhibitor of tumor cell proliferation, or an activator of tumor cell apoptosis.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. Antibodies of the invention can also be used in combination with radiation therapy. An antibody of the invention (and any additional therapeutic agent) can be administered by any suitable means, including parenteral, intrapulmonary, and intranasal, and, if desired for local treatment, intralesional administration. Parenteral administration includes intramuscular, intravenous, intraarterial, intraperitoneal, or subcutaneous administration. Intravenous administration is typically preferred. However, the intraperitoneal route is expected to be particularly useful, for example, in the treatment of colorectal tumors. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 μg/kg to 15 mg/kg (e.g., 0.1 mg/kg to 10 mg/kg) of antibody can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g., every week or every three weeks (e.g., such that the patient receives from about two to about twenty, or e.g., about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an antibody conjugate of the invention in place of or in addition to an anti-TnC antibody.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-TnC antibody.

Specific Embodiments

1. An antibody that specifically binds to Tenascin-C (TnC), wherein said antibody comprises a heavy chain variable region comprising
   (a) a heavy chain CDR1 selected from the group of SEQ ID NO: 49 and SEQ ID NO: 52;
   (b) a heavy chain CDR2 selected from the group of SEQ ID NO: 50 and SEQ ID NO: 53;
   (c) a heavy chain CDR3 selected from the group of SEQ ID NO: 51 and SEQ ID NO: 54,
   and a light chain variable region comprising
   (a) a light chain CDR1 selected from the group of SEQ ID NO: 37 and SEQ ID NO: 40;
   (b) a light chain CDR2 selected from the group of SEQ ID NO: 38 and SEQ ID NO: 41,
   and (c) a light chain CDR3 selected from the group of SEQ ID NO: 39 and SEQ ID NO: 42.

2. An antibody that specifically binds to Tenascin-C (TnC), wherein said antibody comprises:
   (i) a heavy chain variable region comprising a heavy chain CDR1 of SEQ ID NO: 49, a heavy chain CDR2 of SEQ ID NO: 50, a heavy chain CDR3 of SEQ ID NO:51; and a light chain variable region comprising a light chain CDR1 of SEQ ID NO: 37, a light chain CDR2 of SEQ ID NO: 38 and a light chain CDR3 of SEQ ID NO: 39; or
   (ii) a heavy chain variable region combrising a heavy chain CDR1 of SEQ ID NO: 52, a heavy chain CDR2 of SEQ ID NO: 53, a heavy chain CDR3 of SEQ ID NO: 54; and a light chain variable region comprising a light chain CDR1 of SEQ ID NO: 40, a light chain CDR2 of SEQ ID NO:41 and a light chain CDR3 of SEQ ID NO: 42;
   wherein said antibody has cross-species reactivity.

3. The antibody of any one of embodiments 1 or 2, wherein said antibody comprises a heavy chain variable region comprising
   (a) the heavy chain CDR1 of SEQ ID NO: 49;
   (b) the heavy chain CDR2 of SEQ ID NO: 50;
   (c) the heavy chain CDR3 of SEQ ID NO: 51,
   and a light chain variable region comprising
   (a) the light chain CDR1 of SEQ ID NO: 37;
   (b) the light chain CDR2 of SEQ ID NO: 38, and
   (c) the light chain CDR3 of SEQ ID NO: 39.

4. The antibody of embodiment any one of embodiments 1 or 2, wherein said antibody comprises a heavy chain variable region comprising
   (a) the heavy chain CDR1 of SEQ ID NO: 52;
   (b) the heavy chain CDR2 of SEQ ID NO: 53;
   (c) the heavy chain CDR3 of SEQ ID NO: 54,
   and a light chain variable region comprising
   (a) the light chain CDR1 of SEQ ID NO: 40;
   (b) the light chain CDR2 of SEQ ID NO: 41, and
   (c) the light chain CDR3 of SEQ ID NO: 42.

5. The antibody of any one of embodiments 1 to 4, wherein said antibody comprises a heavy chain variable region comprising an amino acid sequence of SEQ ID NO: 28 and a light chain variable region comprising an amino acid sequence of SEQ ID NO: 27.

6. The antibody of any one of embodiments 1 to 4, wherein said antibody comprises a heavy chain variable region comprising an amino acid sequence of SEQ ID NO: 30 and a light chain variable region comprising an amino acid sequence of SEQ ID NO: 29.

7. The antibody of any one of embodiments 1 to 6, wherein said antibody comprises an Fc region or a region equivalent to the Fc region of an immunoglobulin.

8. The antibody of any one of embodiments 1 to 7, wherein said Fc region is an IgG1 Fc region.
9. The antibody of any one of embodiments 1 to 8, wherein said antibody is a full-length IgG1 class antibody.
10. The antibody of any one of embodiments 1 to 9, wherein said antibody comprises a human constant region.
11. The antibody of any one of embodiments 1 to 10, wherein said antibody is a human antibody.
12. The antibody of any one of embodiments 1 to 11, wherein said antibody comprises a light chain region comprising an amino acid sequence of SEQ ID NO: 59 and a heavy chain region comprising an amino acid sequence of SEQ ID NO: 60.
13. The antibody of any one of embodiments 1 to 12, wherein said antibody comprises a light chain region comprising an amino acid sequence of SEQ ID NO: 61 and a heavy chain region comprising an amino acid sequence of SEQ ID NO: 62.
14. The antibody of any one of embodiments 1 to 13, wherein said antibody has an improved affinity.
15. The antibody of any one of embodiments 1 to 14, wherein said antibody binds to human TnC with a $K_D$ value lower than about 1 nM.
16. The antibody of any one of embodiments 1 to 15, wherein said antibody has cross-species reactivity.
17. The antibody of any one of embodiments 1 to 16, wherein said antibody binds to at least one of human, mouse and cynomolgus TnC with a $K_D$ value lower than about 2 nM.
18. The antibody of any one of claims 1 to 17, wherein the antibody binds to human, mouse and cynomolgus TnC.
19. The antibody of any one of claims 1 to 18, wherein said antibody binds to the target antigen from all indicated species with similar affinity.
20. The antibody of any one of claims 1 to 19, wherein said antibody binds to the target antigen from all indicated species with similar affinity, in particular within a $K_D$ range of a factor of 100, within a $K_D$ range of a factor of 50, within a $K_D$ range of a factor of 20, within a $K_D$ range of a factor of 10, within a $K_D$ range of a factor of 5.
21. The antibody of any one of claims 1 to 20, wherein said antibody binds to the target antigen from all indicated species with similar affinity within a $K_D$ range of a factor of 10.
22. The antibody of any one of embodiments 1 to 21, wherein said antibody binds to human TnC with a first $K_D$ value $K_D1$, wherein said antibody binds to mouse TnC with a second $K_D$ value $K_D2$, and wherein said antibody binds to cynomolgus TnC with a third KD value $K_D3$, wherein all of the $K_D$ values selected from the group consisting of $K_D1$, $K_D2$ and $K_D3$ are lower than about 2 nM.
23. The antibody of any one of embodiments 1 to 22, wherein said antibody binds to human TnC with a first $K_D$ value $K_D1$, wherein said antibody binds to mouse TnC with a second $K_D$ value $K_D2$, and wherein said antibody binds to cynomolgus TnC with a third KD value $K_D3$, wherein all of the $K_D$ values selected from the group consisting of $K_D1$, $K_D2$ and $K_D3$ are in the range of 2 nM to 0.1 nM.
24. The antibody of any one of embodiments 1 to 23, wherein said antibody is specific for at least one of the TnC domain selected from the group consisting of A1, A2, A3, A4, B, AD1, AD2, C and D.
25. The antibody of any one of embodiments 1, 2, 3, 5 or 12, wherein said antibody is specific for the TnC domains A1 and A4.
26. The antibody of any one of embodiments 1, 2, 4, 6 or 13, wherein said antibody is specific for the TnC domain C.
27. The antibody of any one of embodiments 1 to 26, wherein said antibody comprises an Fc region comprising at least one amino acid substitution in the Fc region.
28. The antibody of embodiment 27, wherein the parent non-substituted Fc region comprises the amino acid residues Leu234, Leu235 and Pro329, wherein the substituted Fc region comprises at least one of the amino acid substitutions selected from the group consisting of Leu234Ala, Leu235Ala and Pro329Gly relative to the parent non-substituted Fc region.
29. The antibody of embodiment 28, wherein the antibody comprising the substituted Fc region has decreased effector function and/or decreased Fc receptor binding affinity compared to the antibody comprising the parent non-substituted heavy chain region.
30. The antibody of any one of embodiments 27 to 29, comprising the amino acid substitutions Leu234Ala, Leu235Ala and Pro329Gly relative to the parent non-substituted Fc region, wherein binding to FcγR and C1q is abolished and/or wherein Fc-mediated effector function is abolished.
31. The antibody of embodiment 30, wherein said abolished effector function is abolished ADCC.
32. The antibody of any one of embodiments 1 to 31, wherein said antibody comprises a heavy chain region comprising an amino acid sequence selected from the group of: SEQ ID NO: 65 and SEQ ID NO: 66.
33. The antibody of any one of embodiments 1 to 32, wherein said antibody comprises a glycoengineered Fc region.
34. The antibody of embodiment 33, wherein said antibody has an increased proportion of non-fucosylated oligosaccharides in said Fc region, as compared to a non-glycoengineered antibody.
35. The antibody of embodiments 33 or 34, wherein at least about 20% to about 100% of the N-linked oligosaccharides in said Fc region are non-fucosylated.
36. The antibody of any one embodiments 33 to 35, wherein said antibody has an increased proportion of bisected oligosaccharides in said Fc region, as compared to a non-glycoengineered antibody.
37. The antibody of any one of embodiments 33 to 36, wherein at least about 20% to about 100% of the N-linked oligosaccharides in said Fc region are bisected.
38. The antibody of any one of embodiments 33 to 37, wherein at least about 20% to about 50% of the N-linked oligosaccharides in said Fc region are bisected, non-fucosylated.
39. The antibody of any one of embodiments 33 to 38, wherein said antibody has increased effector function and/or increased Fc receptor binding affinity.
40. The antibody of embodiment 39, wherein said increased effector function is increased ADCC.
41. The antibody of any one of claims 1 to 40, wherein the antibody is a multispecific antibody.
42. The antibody of any one of claims 1 to 41, wherein the antibody is a bispecific antibody.

43. An isolated polynucleotide encoding a polypeptide that forms part of the antibody according to any one of embodiments 1 to 42.
44. An isolated polypeptide encoded by the polynucleotide of embodiment 43.
45. A composition comprising a first isolated polynucleotide encoding a polypeptide comprising a sequence selected from the group of SEQ ID NO: 60, SEQ ID NO: 62, SEQ ID NO: 65, and SEQ ID NO: 66, and a second isolated polynucleotide encoding a polypeptide comprising a sequence selected from the group of SEQ ID NO: 59 and SEQ ID NO: 61.
46. A vector comprising the polynucleotide of embodiment 43.
47. A host cell comprising the polynucleotide of embodiment 43, the composition of embodiment 45, or the vector of embodiment 46.
48. The host cell of embodiment 47, wherein said host cell has been manipulated to express increased levels of one or more polypeptides having GnTIII activity.
49. The host cell of embodiment 48, wherein said polypeptide having GnTIII activity is a fusion polypeptide comprising the catalytic domain of GnTIII and the Golgi localization domain of ManII.
50. The host cell of embodiment 48 or 49, wherein said host cell has been further manipulated to express increased levels of one or more polypeptides having ManII activity.
51. A method of producing an antibody that specifically binds to TnC, said method comprising
    a) culturing the host cell of any one of embodiments 47 to 50 in a medium under conditions allowing the expression of the antibody, and
    b) recovering the antibody.
52. A method of producing an antibody that specifically binds to TnC, said method comprising
    a) culturing the host cell of any one of embodiments 48 to 50 in a medium under conditions allowing the expression of the antibody and the modification of the oligosaccharides present on the Fc region of said antibody by said polypeptide having GnTIII activity, and
    b) recovering the antibody
53. An antibody that specifically binds to TnC, wherein said antibody is produced by the method of embodiment 51 or 52.
54. An antibody conjugate comprising the antibody of any one of embodiments 1 to 40 and a cytotoxic agent.
55. A pharmaceutical formulation comprising the antibody of any one of embodiments 1 to 42 and a pharmaceutically acceptable carrier.
56. The pharmaceutical formulation of embodiment 55, further comprising an additional therapeutic agent.
57. The antibody of any one of embodiments 1 to 42 for use as a medicament.
58. The antibody of any one of embodiments 1 to 42 for use in the treatment of a disease characterized by expression of TnC.
59. The antibody of embodiment 58, wherein said disease is cancer.
60. The antibody of any one of embodiments 1 to 42 for use in inducing cell lysis of a tumor cell or a stromal cell of a tumor.
61. Use of the antibody of any one of embodiments 1 to 42 in the manufacture of a medicament for treatment of a disease characterized by expression of TnC.
62. The use of embodiment 61, wherein said disease is cancer.
63. Use of the antibody of any one of embodiments 1 to 42 for the manufacture of a medicament for inducing lysis of a tumor cell or a stromal cell of a tumor.
64. A method of treating an individual having a disease characterized by TnC expression, comprising administering to the individual an effective amount of the antibody of any one of embodiments 1 to 42, or the pharmaceutical formulation of embodiment 55 or 56.
65. The method of embodiment 64 further comprising administering an additional therapeutic agent to the individual.
66. The method of embodiment 64 or 65, wherein said disease is cancer.
67. A method of inducing cell lysis of a tumor cell or a stromal cell of a tumor, said method comprising contacting said tumor cell or stromal cell with the antibody of any one of embodiments 1 to 42.
68. The method of embodiment 67, wherein said cell lysis is induced by antibody dependent cytotoxicity of the antibody.
69. A method of diagnosing disease in an individual, said method comprising administering to the individual an effective amount of a diagnostic agent, wherein said diagnostic agent comprises the antibody of any one of embodiments 1 to 42 and a label that allows detection of a complex of said diagnostic agent and TnC.
70. The invention as described hereinbefore.

III. EXAMPLES

The following are examples of methods and compositions of the invention. It is understood that various other embodiments may be practiced, given the general description provided above.

Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions. DNA sequences were determined by double strand sequencing. In some cases desired gene segments were prepared by Geneart AG (Regensburg, Germany) from synthetic oligonucleotides and PCR products by automated gene synthesis. The gene segments which are flanked by singular restriction endonuclease cleavage sites were cloned into indicated plasmids. The plasmid DNA was purified from transformed bacteria and concentration determined by UV spectroscopy. The DNA sequence of the subcloned gene fragments was confirmed by DNA sequencing. Gene Segments were designed with suitable restriction sites to allow sub-cloning into the respective expression vectors.

General information regarding the nucleotide sequences of human immunoglobulin light and heavy chains is given in: Kabat, E. A. et al., (1991) Sequences of Proteins of Immunological Interest, Fifth Ed., NIH Publication No 91-3242. For expression, all constructs contained a 5'-end DNA sequence coding for a leader peptide which targets proteins for secretion in eukaryotic cells.

Exemplary leader peptides and polynucleotide sequences encoding them are given in SEQ ID NO 67 to SEQ ID NO 75.

Example 1

TnC Antigen Sequences and Production of Antigens

All constructs of Table 3 and Table 4 are fused to the C-term of GST and are expressed in *E. coli* BL21(DE3). For site specific biotinylation, the Avi-tag was added to the C-term of the tenascin sequence, and the BirA biotin ligase was coexpressed on a separate plasmid (Avidity, Colorado, USA). Growth medium was 2YT with 100 μg/ml ampicillin and 20 μg/ml chloramphenicol. Biotin was added to a final concentration of 50 μM. Protein Expression was induced with 1 mM IPTG at 22° C. overnight. Cells were harvested by centrifugation, and cell-lysis was performed by sonication in the presence of B-PER reagent (pierce 78260), and 1 mg/ml lysozyme (Sigma L6876). Lysate was centrifuged and cleared lysate was loaded on Glutathione Sepharose columns (GE Healthcare; Product No 17-0756-01). After washing, the TnC molecules were cleaved from the GST via Thrombin (Sigma Aldrich; Product No 10602400001) over night at 4° C. Elution was performed in 50 mM Tris buffer pH 8.0; 200 mM NaCl, 5 mM MgCl2, 1 mM DTT and 10% glycerol. The final purification step was on a gelfiltration column (Superdex 75 16/60; GE Healthcare). Samples were flash frozen in liquid nitrogen until processing.

TABLE 3

Sequences of TnC antigens used for cross-species affinity determination (reference Table 26)

| Antigen | Sequence | SEQ ID NO |
|---|---|---|
| huTNC | ATGTCCCTATACTAGGTTATTGGAAAATTAAGGG CCTTGTGCAACCCACTCGACTTCTTTTGGAATATC TTGAAGAAAAATATGAAGAGCATTTGTATGAGCG CGATGAAGGTGATAAATGGCGAAACAAAAAGTTT GAATTGGGTTTGGAGTTTCCCAATCTTCCTTATTAT ATTGATGGTGATGTTAAATTAACACAGTCTATGGC CATCATACGTTATATAGCTGACAAGCACAACATGT TGGGTGGTTGTCCAAAAGAGCGTGCAGAGATTTC AATGCTTGAAGGAGCGGTTTTGGATATTAGATACG GTGTTTCGAGAATTGCATATAGTAAAGACTTTGAA ACTCTCAAAGTTGATTTTCTTAGCAAGCTACCTGA AATGCTGAAAATGTTCGAAGATCGTTTATGTCATA AAACATATTTAAATGGTGATCATGTAACCCATCCT GACTTCATGTTGTATGACGCTCTTGATGTTGTTTTA TACATGGACCCAATGTGCCTGGATGCGTTCCCAAA ATTAGTTTGTTTTAAAAAACGTATTGAAGCTATCC CACAAATTGATAAGTACTTGAAATCCAGCAAGTA TATAGCATGGCCTTTGCAGGGCTGGCAAGCCACGT TTGGTGGTGGCGACCATCCTCCAAAATCGGATGGT TCAACTAGTGGTTCTGGTCATCACCATCACCATCA CTCCGCGGGTCTGGTGCCACGCGGTAGTACTGCAA TTGGTATGAAAGAAACCGCTGCTGCTAAATTCGA ACGCCAGCACATGGACAGCCCAGATCTGGGTACC GGTGGTGGCTCCGGTATTGAGGGACGCGGGTCCA TGGGATATCGGGGATCCGAGCTGGACACCCCCAA GGACCTGCAGGTGTCCGAGACAGCCGAGACAAGC CTGACCCTGCTGTGGAAAACCCCCTGGCCAAGTT CGACCGGTACAGACTGAACTACAGCCTGCCCACT GGACAGTGGGTCGGCGTGCAGCTGCCCCGGAACA CCACCTCCTACGTGCTGCGGGGCCTGGAACCCGGC CAGGAATACAACGTCCTGCTGACGGCCGAGAAGG GCCGGCACAAGAGCAAGCCCGCCAGAGTGAAGGC CAGCACCGAGCAGGCCCCCGAGCTGGAAAACCTG ACCGTGACCGAAGTGGGCTGGGACGGCCTGCGGC TGAACTGGACCGCGCTGACCAGGCCTATGAGCA CTTTATCATTCAGGTGCAGGAGGCCAACAAGGTG GAGGCAGCTCGGAACCTCACCGTGCCTGGCAGCC TTCGGGCTGTGGACATACCGGGCCTCAAGGCTGCT ACGCCTTATACAGTCTCCATCTATGGGTGATCCA GGGCTATAGAACACCAGTGCTCTCTGCTGAGGCCT CCACAGGCGAAACACCGAACCTGGGCGAAGTGGT GGTGGCGGAAGTGGGTTGGGATGCGCTGAAACTG AACTGGACCGCGCCGGAAGGCGCGTATGAATATT TTTTCATCCAGGTGCAGGAAGCGGATACCGTTGAA GCGGCGCAGAACCTGACCGTTCCGGGCGGTCTGC GTAGCACCGATCTGCCGGGCCTGAAAGCGGCGAC CCATTATACCATTACCATCCGTGGGGTGACCCAGG ACTTCTCTACCACCCCTCTGAGCGTGGAGGTGCTG ACCGAGGAGGTACCCGACATGGGCAACCTGACCG TGACCGAGGTGTCCTGGGACGCCCTGCGGCTGAA CTGGACCACCCCCGACGGCACCTACGACCAGTTC ACAATCCAGGTGCAGGAAGCCGACCAGGTGGAAG AAGCACATAATCTGACCGTTCCGGGTAGCCTGCGT AGCATGGAAATTCCGGGTCTGCGTGCAGGCACCC CGTATACCGTTACCCTGCATGGTGAAGTTCGTGGT CATAGCACCCGTCCGCTGGCAGTTGAAGTTGTTAC CGAAGATCTGCCGCAGCTGGGTGATCTGGCAGTT AGCGAAGTTGGTTGGGATGGTCTGCGTCTGAATTG GACCGCAGCAGATAATGCATATGAACATTTTGTG ATCCAGGTGCAAGAGGTGAATAAAGTTGAAGCAG CCCAGAATCTGACCCTGCCTGGTTCACTGCGTGCA GTTGATATTCCGGGACTCGAGGCAGCAACCCCGT ATCGTGTTAGCATTTATGGTGTTATTCGCGGTTAT CGTACACCGGTTCTGAGCGCAGAAGCAAGCACCG CAAAAGAACCGGAAATTGGTAATCTGAACGTGAG CGATATTACACCGGAATCATTTAATCTGAGCTGGA TGGCAACCGATGGTATTTTTGAAACCTTTACCATC GAGATCATCGATAGCAATCGTCTGCTGGAAACCG TGGAATATAATATTAGCGGTGCAGAACGTACCGC ACATATTAGCGGTCTGCCTCCGAGCACCGATTTTA TTGTTTATCTGAGCGGTCTGGCACCGAGCATTCGT ACCAAAACCATTAGCGCAACCGCAACCACCGAAG CACTGCCGCTGCTGGAAAATCTGACCATTAGCGAT ATTAACCCGTATGGTTTTACCGTTTCATGGATGGC AAGCGAAAATGCATTTGATAGCTTTCTGGTTACAG TTGTGGATAGCGGTAAACTGCTGGACCCGCAAGA ATTTACCCTGAGCGGCACCCAGCGCAAACTGGAA CTGCGTGGTCTGATTACCGGTATTGGTTATGAAGT TATGGTGAGCGGTTTTACCCAGGGTCATCAGACCA AACCGCTGCGTGCAGAAATTGTTACCGAAGCAAT GGGTAGCCCGAAAGAGTTATTTTTTCCGATATCA CCGAGAATTCGGCAACCGTTAGCTGGCGTGCACC GACCGCACAGGTTGAAAGCTTTGTATTACCTATG TTCCGATTACCGGTGGCACCCCGAGCATGGTTACA GTTGATGGCACCAAAACCCAGACCCGTCTGGTTA AACTGATTCCGGGTGTTAATATCTGGTTAGCATT ATTGCCATGAAAGGCTTTGAAGAAAGCGAACCGG TTAGCGGTAGCTTTACCACAGCTAGCGGCCTGAAC GACATCTTCGAGGCTCAGAAAATCGAATGGCACG AAGGTACCCATCACCATCACCACCACTAA | SEQ ID NO: 1 |
| muTNC | TATGTCCCCTATACTAGGTTATTGGAAAATTAAGG GCCTTGTGCAACCCACTCGACTTCTTTTGGAATAT CTTGAAGAAAAATATGAAGAGCATTTGTATGAGC GCGATGAAGGTGATAAATGGCGAAACAAAAAGTT TGAATTGGGTTTGGAGTTTCCCAATCTTCCTTATTA TATTGATGGTGATGTTAAATTAACACAGTCTATGG CCATCATACGTTATATAGCTGACAAGCACAACATG TTGGGTGGTTGTCCAAAAGAGCGTGCAGAGATTTC AATGCTTGAAGGAGCGGTTTTGGATATTAGATACG GTGTTTCGAGAATTGCATATAGTAAAGACTTTGAA ACTCTCAAAGTTGATTTTCTTAGCAAGCTACCTGA AATGCTGAAAATGTTCGAAGATCGTTTATGTCATA AAACATATTTAAATGGTGATCATGTAACCCATCCT GACTTCATGTTGTATGACGCTCTTGATGTTGTTTTA TACATGGACCCAATGTGCCTGGATGCGTTCCCAAA ATTAGTTTGTTTTAAAAAACGTATTGAAGCTATCC CACAAATTGATAAGTACTTGAAATCCAGCAAGTA TATAGCATGGCCTTTGCAGGGCTGGCAAGCCACGT TTGGTGGTGGCGACCATCCTCCAAAATCGGATGGT TCAACTAGTGGTTCTGGTCATCACCATCACCATCA CTCCGCGGGTCTGGTGCCACGCGGTAGTACTGCAA TTGGTATGAAAGAAACCGCTGCTGCTAAATTCGA ACGCCAGCACATGGACAGCCCAGATCTGGGTACC GGTGGTGGCTCCGGTATTGAGGGACGCGGGTCCA | SEQ ID NO: 2 |

TABLE 3-continued

Sequences of TnC antigens used for cross-species affinity determination (reference Table 26)

| Antigen | Sequence | SEQ ID NO |
|---|---|---|
|  | TGGGATATCGGGGATCCGAGCTGGACACCCCCAA GGACCTGCAGGTGTCCGAGACAGCCGAGACAAGC CTGACCCTGCTGTGGAAAACCCCCTGGCCAAGTT CGACCGGTACAGACTGAACTACAGCCTGCCCACT GGACAGTGGGTCGGCGTGCAGCTGCCCCGGAACA CCACCTCCTACGTGCTGCGGGGCCTGGAACCCGGC CAGGAATACAACGTCCTGCTGACGGCCGAGAAGG GCCGGCACAAGAGCAAGCCCGCCAGAGTGAAGGC CAGCACCGAGGAAGTGCCCAGCCTGGAAAACCTG ACCGTGACCGAGGCCGGCTGGGACGGCCTGCGGC TGAACTGGACCGCCGACGACCTGGCCTACGAGTA CTTCGTGATCCAGGTGCAGGAAGCCAACAACGTC GAGACAGCCCACAACTTCACCGTGCCCGGCAACC TGAGAGCCGCCGACATCCCCGGCCTGAAGGTGGC CACATCCTACCGGGTGTCCATCTACGGCGTGGCCA GGGGCTACCGGACCCCCGTGCTGTCCGCCGAGAC AAGCACCGGCACCACGCCGAACCTGGGCGAAGTG ACCGTGACGGAAGTGGGTTGGGATGCGCTGACCC TGAATTGGACCGCACCGGAAGGCGCGTATAAAAA CTTTTTCATCCAGGTGCTGGAAGCGGATACCACCC AGACCGTGCAGAACCTGACCGTGCCGGGTGGTCT GCGTAGCGTAGATCTGCCTGGTCTGAAAGCAGCA ACCCGCTATTACATTACCCTGCGTGGTGTTACCCA GGATTTTGGCACCGCACCGCTGAGCGTTGAAGTTC TGACCGAGGATCTGCCGCAGCTGGGTGGTCTGAG CGTTACCGAAGTTAGTTGGGATGGTCTGACCCTGA ATTGGACCACCGATGATCTGGCATATAAACATTTT GTGGTGCAGGTTCAAGAGGCAATAATGTTGAAG CAGCACAGAATCTGACCGTTCCGGGTAGCCTGCGT GCAGTTGATATTCCGGGACTGAAAGCCGATACC CGTATCGTGTTAGCATTTATGGTGTTATTCAGGGT TATCGTACCCCGATGCTGAGCACCGATGTTAGCAC AGCACGTGAACCGGAAATTGGTAATCTGAATGTT AGTGATGTGACCCCGAAATCATTTAATCTGAGCTG GACCGCAACCGATGGTATTTTTGATATGTTTACCA TTGAAATTATTGATAGCAATCGCTGCTGCAGACC GCAGAACATAACATTAGCGGTGCAGAACGTACCG CACATATTAGCGGTCTGCCTCCGAGCACCGATTTT ATTGTTTATCTGAGCGGTATTGCACCGAGCATTCG TACCAAAACCATTAGCACCACCGCAACCACCGAA GCACTGACCGCAATGGGTAGCCCGAAAGAAGTGA TTTTTAGCGATATTACCGAAAATAGCGCCACCGTT TCATGGCGTGCACCGACCGCACAGGTTGAAAGCT TTCGTATTACCTATGTTCCGATTACCGGTGGCACC CCGAGCATGGTTACCGTTGATGGCACCAAAACCC AGACCCGTCTGGTTAAACTGATTCCGGGTGTTGAA TATCTGGTTAGCATTATTGCCATGAAAGGCTTTGA AGAAAGCGAACCGGTTAGCGGTAGCTTTACCACA GCTAGCGGCCTGAACGACATCTTCGAGGCTCAGA AAATCGAATGGCACGAAGGTACCCATCACCATCA CCACCACTAA |  |
| cynoTNC | ATGTCCCCTATACTAGGTTATTGGAAAATTAAGGG CCTTGTGCAACCCACTCGACTTCTTTTGGAATATC TTGAAGAAAATATGAAGAGCATTTGTATGAGCG CGATGAAGGTGATAAATGGCGAACAAAAAGTTT GAATTGGGTTTGGAGTTTCCCAATCTTCCTTATTAT ATTGATGGTGATGTTAAATTAACACAGTCTATGGC CATCATACGTTATATAGCTGACAAGCACAACATGT TGGGTGGTTGTCCAAAAGAGCGTGCAGAGATTTC AATGCTTGAAGGAGCGGTTTGGATATTAGATACG GTGTTTCGAGAATTGCATATAGTAAAGACTTTGAA ACTCTCAAAGTTGATTTTCTTAGCAAGCTACCTGA AATGCTGAAATTGTTCGAAGATCGTTTATGTCATA AAACATATTTAAATGGTGATCATGTAACCCATCCT GACTTCATGTTGTATGACGCTCTTGATGTTGTTTA TACATGGACCCAATGTGCCTGGATGCGTTCCCAAA ATTAGTTTGTTTTAAAAAACGTATTGAAGCTATCC CACAAATTGATAAGTACTTGAAATCCAGCAAGTA TATAGCATGGCCTTTGCAGGGCTGGCAAGCACGT TTGGTGGTGGCGACCATCCTCCAAAATCGGATGGT TCAACTAGTGGTTCTGGTCATCACCATCACCATCA CTCCGCGGGTCTGGTGCCACGCGGTAGTACTGCAA | SEQ ID NO: 3 |
|  | TTGGTATGAAAGAAACCGCTGCTGCTAAATTCGA ACGCCAGCACATGGACAGCCCAGATCTGGGTACC GGTGGTGGCTCCGGTATTGAGGGACGCGGGTCCA TGGGATATCGGGGATCCGAACTGGATACCCCGAA AGATCTGCGTGTTAGCGAAACCGCAGAAACCAGC CTGACCCTGTTTTGGAAAACACCGCTGGCAAAATT TGATCGTTATCGTCTGAATTATAGCCTGCCGACCG GTCAGTGGGTTGGTGTTCAGCTGCCTCGTAATACC ACCAGTTATGTTCTGCGTGGTCTGGAACCGGGTCA AGAATATAACGTTCTGCTGACCGCAGAAAAAGGT CGTCATAAAAGCAAACCGGCACGTGTTAAAGCAA GCACCGAACAGGCACCGGAACTGGAAAATCTGAC CGTTACCGAAGTTGGCTGGGATGGCCTGCGCCTGA ACTGGACGCTTCTGCGACCAGGCCTACGAACACTT CGTTATCCAGGTGCAAGAAGCCAACAAAGTAGAA GCCGCTCAGAATCTGACCGGTTCCGGGAAATCTGC GTGCAGTTGATATTCCGGGTCTGAAAGCAGCAAC CCGTATACCGTTAGCATTTATGGTGTTATTCAGG GTTATCGTACACCGGTTCTGAGTGCCGAAGCCAGC ACCGGTGAAACCCCGAATCTGGGTGAAGTTATGG TTAGCGAAGTGGGCTGGGATGCACTGAAACTGAA TTGGACAGTTCCGGAAGGTGCCTATGAATACTTTT TCATTCAGGTTCAAGAAGCGGATACCGTTGAAGC CGCTCAGAATCATACCGTTCCGGGTGGTCTGCGTA GCACCGATCTGCCTGGCCTGAAAGCCGCTACCCAT TACACCATTACCATTCGTGGTGTTACCCAGGATTT TAGCACCACACCGCTGAGCGTTGAAGTTCTGACA GAAGAACTGCCGCAGCTGGGTGATCTGGCAGTTA GCGAAGTTGGTTGGGATGGTCTGCGTCTGAATTGG ACCGCAGCAGATCAGGCATATGAACATTTTGTTAT CCAGGTGCAAGAAGTGAACAAAGTTGAAGCAGCA CAGAATCTGACCGTTCCGGGTAGCCTGCGTCAGTG TGATATTCCGGGTCTGAAAGCAGCAACCCCGTATA CCGTTAGCATTTATGGTGTTATTCGCGGTTATCGT ACACCGGTTCTGAGCGCCGAAAGCAAGCACCGCAA AAGAACCGGAAATTGGTAATCTGAACGTGAGCGA TATTACACCGGAAAGTTTTAGCCTGAGCTGGACCG CAACCGATGGTATTTTTGAAACCTTTACCATCGAG ATCATCGATAGCAACCGCAACCACCGAAGCACT GACCGCAATGGGTAGCCCGAAAGAAGTGATTTTT AGCGATATTACCGAAAATAGCGCCACCGTTTCATG GCGTGCACCGACCGCACAGGTTGAAAGCTTTCGT ATTACCTATGTTCCGATTACCGGTGGCACCCCGAG CATGGTTACCGTTGATGGCACCAAAACCCAGACC CGTCTGGTTAAACTGATTCCGGGTGTTAATATCT GGTGAATATCATTGCCATGAAAGGCTTTGAAGAA AGCGAACCGGTTAGCGGTAGCTTTACCACCGCTA GCGGCCTGAACGACATCTTCGAGGCTCAGAAAAT CGAATGGCACGAAGGTACCCATCACCATCACCAC CACTAA |  |
| huTNC | MSPILGYWKIKGLVQPTRLLLEYLEEKYEEHLYERD EGDKWRNKKFELGLEFPNLPYYIDGDVKLTQSMAII RYIADKHNMLGGCPKERAEISMLEGAVLDIRYGVSR IAYSKDFETLKVDFLSKLPEMLKMFEDRLCHKTYLN GDHVTHPDFMLYDALDVVLYMDPMCLDAFPKLVC FKKRIEAIPQIDKYLKSSKYIAWPLQGWQATFGGGD HPPKSDGSTSGSGHHHHHHSAGLVPRGSTAIGMKET AAAKFERQHMDSPDLGTGGGSGIEGRGSMGYRGSE LDTPKDLQVSETAETSLTLLWKTPLAKFDRYRLNYS LPTGQWVGVQLPRNTTSYVLRGLEPGQEYNVLLTA EKGRHKSKPARVKASTEQAPELENLTVTEVGWDGL RLNWTAADQAYEHFIIQVQEANKVEAARNLTVPGS LRAVDIPGLKAATPYTVSIYGVIQGYRTPVLSAEAS TGETPNLGEVVVAEVGWDALKLNWTAPEGAYEYFFI QVQEADTVEAAQNLTVPGGLRSTDLPGLKAATHYTI TIRGVTQDFSTTPLSVEVLTEEVPDMGNLTVTEVSW DALRLNWTTPDGTYDQFTIQVQEADQVEEAHNLTVP GSLRSMEIPGLRAGTPYTVTLHGEVRGHSTRPLAVE | SEQ ID NO: 4 |

TABLE 3-continued

Sequences of TnC antigens used for cross-species affinity determination (reference Table 26)

| Antigen | Sequence | SEQ ID NO |
|---|---|---|
|  | VVTEDLPQLGDLAVSEVGWDGLRLNWTAADNAYEHF VIQVQEVNKVEAAQNLTLPGSLRAVDIPGLEAATPY RVSIYGVIRGYRTPVLSAEASTAKEPEIGNLNVSDI TPESFNLSWMATDGIFETFTIEIIDSNRLLETVEY NISGAERTAHISGLPPSTDFIVYLSGLAPSIRTKTI SATATTEALPLLENLTISDINPYGFTVSWMASENAF DSFLVTVVDSGKLLDPQEFTLSGTQRKLELRGLIT GIGYEVMVSGFTQGHQTKPLRAEIVTEAMGSPKEVI FSDITENSATVSWRAPTAQVESFRITYVPITGGTP SMVTVDGTKTQTRLVKLIPGVEYLVSIIAMKGFEES EPVSGSFTTASGLNDIFEAQKIEWHEGTHHHHHH |  |
| muTNC | MSPILGYWKIKGLVQPTRLLLEYLEEKYEEHLYERD EGDKWRNKKFELGLEFPNLPYYIDGDVKLTQSMAII RYIADKHNMLGGCPKERAEISMLEGAVLDIRYGVSR IAYSKDFETLKVDFLSKLPEMLKMFEDRLCHKTYLN GDHVTHPDFMLYDALDVVLYMDPMCLDAFPKLVC FKKRIEAIPQIDKYLKSSKYIAWPLQGWQATFGGGD HPPKSDGSTSGSGHHHHHHSAGLVPRGSTAIGMKET AAAKFERQHMDSPDLGTGGGSGIEGRGSMGYRGSE LDTPKDLQVSETAETSLTLLWKTPLAKFDRYRLNYS LPTGQWVGVQLPRNTTSYVLRGLEPGQEYNVLLTA EKGRHKSKPARVKASTEEVPSLENLTVTEAGWDGL RLNWTADDLAYEYFVIQVQEANNVETAHNFTVPGNL RAADIPGLKVATSYRVSIYGVARGYRTPVLSAETST GTTPNLGEVTVAEVGWDALTLNWTAPEGAYKNFFI QVLEADTTQTVQNLTVPGGLRSVDLPGLKAATRYYI TLRGVTQDFGTAPLSVEVLTEDLPQLGGLSVTEVSW DGLTLNWTTDDLAYKHFVVQVQEANNVEAAQNLTVP GSLRAVDIPGLKADTPYRVSIYGVIQGYRTPMLSTD VSTAREPEIGNLNVSDVTPKSFNLSWTATDGIFDMF TIEIIDSNRLLQTAEHNISGAERTAHISGLPPSTDF IVYLSGIAPSIRTKTISTTATTEALTAMGSPKEVIF SDITENSATVSWRAPTAQVESFRITYVPITGGTPS MVTVDGTKTQTRLVKLIPGVEYLVSIIAMKGFEESE PVSGSFTTASGLNDIFEAQKIEWHEGTHHHHHH | SEQ ID NO: 5 |
| cynoTNC | MSPILGYWKIKGLVQPTRLLLEYLEEKYEEHLYERD EGDKWRNKKFELGLEFPNLPYYIDGDVKLTQSMAII RYIADKHNMLGGCPKERAEISMLEGAVLDIRYGVSR IAYSKDFETLKVDFLSKLPEMLKMFEDRLCHKTYLN GDHVTHPDFMLYDALDVVLYMDPMCLDAFPKLVC FKKRIEAIPQIDKYLKSSKYIAWPLQGWQATFGGGD HPPKSDGSTSGSGHHHHHHSAGLVPRGSTAIGMKET AAAKFERQHMDSPDLGTGGGSGIEGRGSMGYRGSE LDTPKDLRVSETAETSLTLFWKTPLAKFDRYRLNYS LPTGQWVGVQLPRNTTSYVLRGLEPGQEYNVLLTA EKGRHKSKPARVKASTEQAPELENLTVTEVGWDGL RLNWTAADQAYEHFVIQVQEANKVEAAQNLTVPGNL RAVDIPGLKAATPYTVSIYGVIQGYRTPVLSAEAS TGETPNLGEVMVSEVGWDALKLNWTVPEGAYEYFF IQVQEADTVEAAQNHTVPGGLRSTDLPGLKAATHY TITIRGVTQDFSTTPLSVEVTEELPQLGDLAVSEV GWDGLRLNWTAADQAYEHFVIQVQEVNKVEAAQNL TVPGSLRAVDIPGLKAATPYTVSIYGVIRGYRTPVL SAEASTAKEPEIGNLNVSDITPESFSLSWTATDGIF ETFTIEIIDSNRLLEIVEYNISGAERTAHISGLPP STDFIVYLSGLAPSFRTKTISATATTEALTAMGSPK EVIFSDITENSATVSWRAPTAQVESFRITYVPITGG TPSMVTVDGTKTQTRLVKLPGVEYLVNIIAMKGFE ESEPVSGSFTTASGLNDIFEAQKIEWHEGTHHHHHH | SEQ ID NO: 6 |

TABLE 4

Sequences of TnC antigens used for affinity determination (reference Table 5)

| Antigen pETR # batch ID | Protein Sequence | SEQ ID NO |
|---|---|---|
| GST huTNC fn5 A1234 BC fn6 B | MSPILGYWKIKGLVQPTRLLLEYLEEKYE EHLYERDEGDKWRNKKFELGLEFPNLPYY IDGDVKLTQSMAIIRYIADKHNMLGGCPK ERAEISMLEGAVLDIRYGVSRIAYSKDFE TLKVDFLSKLPEMLKMFEDRLCHKTYLNG DHVTHPDFMLYDALDVVLYMDPMCLDAFP KLVCFKKRIEAIPQIDKYLKSSKYIAWPL QGWQATFGGGDHPPKSDGSTSGSGHHHHHH HSAGLVPRGSTAIGMKETAAAKFERQHMD SPDLGTGGGSGIEGRGSMGYRGSELDTPK DLQVSETAETSLTLLWKTPLAKFDRYRLN YSLPTGQWVGVQLPRNTTSYVLRGLEPGQ EYNVLLTAEKGRHKSKPARVKASTEQAPE LENLTVTEVGWDGLRLNWTAADQAYEHFI IQVQEANKVEAARNLTVPGSLRAVDIPGL KAATPYTVSIYGVIQGYRTPVLSAEASTG ETPNLGEVVVAEVGWDALKLNWTAPEGAY EYFFIQVQEADTVEAAQNLTVPGGLRSTD LPGLKAATHYTITIRGVTQDFSTTPLSVE VLTEEVPDMGNLTVTEVSWDALRLNWTTP DGTYDQFTIQVQEADQVEEAHNLTVPGSL RSMEIPGLRAGTPYTVTLHGEVRGHSTRP LAVEVVTEDLPQLGDLAVSEVGWDGLRLN WTAADNAYEHFVIQVQEVNKVEAAQNLTL PGSLRAVDIPGLEAATPYRVSIYGVIRGY RTPVLSAEASTAKEPEIGNLNVSDITPES FNLSWMATDGIFETFTIEIIDSNRLLETV EYNISGAERTAHISGLPPSTDFIVYLSGL APSIRTKTISATATTEALPLLENLTISDI NTPYGFTVSWMASENAFDSFLVTVVDSGK LLDPQEFTLSGTQRKLELRGLITGIGYEV MVSGFTQGHQTKPLRAEIVTEAMGSPKEV IFSDITENSATVSWRAPTAQVESFRITYV PITGGTPSMVTVDGTKTQTRLVKLIPGVE YLVSIIAMKGFEESEPVSGSFTTASGLND IFEAQKIEWHEGTHHHHHH | SEQ ID NO: 7 |
| GST huTNCfn5 mu A124 BC hu fn6 B | MSPILGYWKIKGLVQPTRLLLEYLEEKYE EHLYERDEGDKWRNKKFELGLEFPNLPYY IDGDVKLTQSMAIIRYIADKHNMLGGCPK ERAEISMLEGAVLDIRYGVSRIAYSKDFE TLKVDFLSKLPEMLKMFEDRLCHKTYLNG DHVTHPDFMLYDALDVVLYMDPMCLDAFP KLVCFKKRIEAIPQIDKYLKSSKYIAWPL QGWQATFGGGDHPPKSDGSTSGSGHHHHHH HSAGLVPRGSTAIGMKETAAAKFERQHMD SPDLGTGGGSGIEGRGSMGYRGSELDTPK DLQVSETAETSLTLLWKTPLAKFDRYRLN YSLPTGQWVGVQLPRNTTSYVLRGLEPGQ EYNVLLTAEKGRHKSKPARVKASTEEVPS LENLTVTEAGWDGLRLNWTADDLAYEYFV IQVQEANNVETAHNFTVPGNLRAADIPGL KVATSYRVSIYGVARGYRTPVLSAETSTG TTPNLGEVTVAEVGWDALTLNWTAPEGAY KNFFIQVLEADTTQTVQNLTVPGGLRSVD LPGLKAATRYYITLRGVTQDFGTAPLSVE VLTEDLPQLGGLSVTEVSWDGLTLNWTTD DLAYKHFVVQVQEANNVEAAQNLTVPGSL RAVDIPGLKADTPYRVSIYGVIQGYRTPM LSTDVSTAREPEIGNLNVSDVTPKSFNLS WTATDGIFDMFTIEIIDSNRLLQTAEHNI SGAERTAHISGLPPSTDFIVYLSGIAPSI RTKTISTTATTEALPLLENLTISDTNPYG FTVSWTASENAFDSFLVTVVDSGKLLDPQ EFTLSGTQRKLELRGLITGIGYEVLVSGF TQGHQTKPLRAETITAMGSPKEVIFSDIT ENSATVSWRAPTAQVESFRITYVPITGGT PSMVTVDGTKTQTRLVKLIPGVEYLVSII AMKGFEESEPVSGSFTTASGLNDIFEAQK IEWHEGTHHHHHH | SEQ ID NO: 8 |

TABLE 4-continued

Sequences of TnC antigens used for affinity determination (reference Table 5)

| Antigen pETR # batch ID | Protein Sequence | SEQ ID NO |
|---|---|---|
| GST TNC hu fn5 B-C fn6 B | MSPILGYWKIKGLVQPTRLLLEYLEEKYE EHLYERDEGDKWRNKKFELGLEFPNLPYY IDGDVKLTQSMAIIRYIADKHNMLGGCPK ERAEISMLEGAVLDIRYGVSRIAYSKDFE TLKVDFLSKLPEMLKMFEDRLCHKTYLNG DHVTHPDFMLYDALDVVLYMDPMCLDAFP KLVCFKKRIEAIPQIDKYLKSSKYIAWPL QGWQATFGGGDHPPKSDGSTSGSGHHHHH HSAGLVPRGSTAIGMKETAAAKFERQHMD SPDLGTGGGSGIEGRGSMGYRGSELDTPK DLQVSETAETSLTLLWKTPLAKFDRYRLN YSLPTGQWVGVQLPRNTTSYVLRGLEPGQ EYNVLLTAEKGRHKSKPARVKASTAKEPE IGNLNVSDITPESFNLSWMATDGIFETFT IEIIDSNRLLETVEYNISGAERTAHISGL PPSTDPIVYLSGLAPSIRTKTISATATTE ALPLLENLTISDINPYGFTVSWMASENAF DSFLVTVVDSGKLLDPQEFTLSGTQRKLE LRGLITGIGYEVMVSGFTQGHQTKPLRAE IVTAMGSPKEVIFSDITENSATVSWRAPT AQVESFRITYVPITGGTPSMVTVDGTKTQ TRLVKLIPGVEYLVSIIAMKGFEESEPVS GSFTTASGLNDIFEAQKIEWHEGTHHHHH H | SEQ ID NO: 9 |
| GST huTNC fn5 A1234 fn6 B | MSPILGYWKIKGLVQPTRLLLEYLEEKYE EHLYERDEGDKWRNKKFELGLEFPNLPYY IDGDVKLTQSMAIIRYIADKHNMLGGCPK ERAEISMLEGAVLDIRYGVSRIAYSKDFE TLKVDFLSKLPEMLKMFEDRLCHKTYLNG DHVTHPDFMLYDALDVVLYMDPMCLDAFP KLVCFKKRIEAIPQIDKYLKSSKYIAWPL QGWQATFGGGDHPPKSDGSTSGSGHHHHH HSAGLVPRGSTAIGMKETAAAKFERQHMD SPDLGTGGGSGIEGRGSMGYRGSELDTPK DLQVSETAETSLTLLWKTPLAKFDRYRLN YSLPTGQWVGVQLPRNTTSYVLRGLEPGQ EYNVLLTAEKGRHKSKPARVKASTEQAPE LENLTVTEVGWDGLRLNWTAADQAYEHFI IQVQEANKVEAARNLTVPGSLRAVDIPGL KAATPYTVSIYGVIQGYRTPVLSAEASTG ETPNLGEVVVAEVGWDALKLNWTAPEGAY EYFFIQVQEADTVEAAQNLTVPGGLRSTD LPGLKAATHYTITIRGVTQDFSTTPLSVE VLTEEVPDMGNLTVTEVSWDALRLNWTTP DGTYDQFTIQVQEADQVEEAHNLTVPGSL RSMEIPGLRAGTPYTVTLHGEVRGHSTRP LAVEVVTEDLPQLGDLAVSEVGWDGLRLN WTAADNAYEHFVIQVQEVNKVEAAQNLTL PGSLRAVDIPGLEAATPYRVSIYGVIRGY RTPVLSAEASTAKEAMGSPKEVIFSDITE NSATVSWRAPTAQVESFRITYVPITGGTP SMVTVDGTKTQTRLVKLIPGVEYLVSIIA MKGFEESEPVSGSFTTASGLNDIFEAQKI EWHEGTHHHHHH | SEQ ID NO: 10 |
| huTNC A4 B | MSPILGYWKIKGLVQPTRLLLEYLEEKYE EHLYERDEGDKWRNKKFELGLEFPNLPYY IDGDVKLTQSMAIIRYIADKHNMLGGCPK ERAEISMLEGAVLDIRYGVSRIAYSKDFE TLKVDFLSKLPEMLKMFEDRLCHKTYLNG DHVTHPDFMLYDALDVVLYMDPMCLDAFP KLVCFKKRIEAIPQIDKYLKSSKYIAWPL QGWQATFGGGDHPPKSDGSTSGSGHHHHH HSAGLVPRGSTAIGMKETAAAKFERQHMD SPDLGTGGGSGIEGRGSMGYRGSEDLPQL GDLAVSEVGWDGLRLNWTAADNAYEHFVI QVQEVNKVEAAQNLTLPGSLRAVDIPGLE AATPYRVSIYGVIRGYRTPVLSAEASTAS GLNDIFEAQKIEWHEGTHHHHHH | SEQ ID NO: 11 |
| huTNC A1 B | MSPILGYWKIKGLVQPTRLLLEYLEEKYE EHLYERDEGDKWRNKKFELGLEFPNLPYY IDGDVKLTQSMAIIRYIADKHNMLGGCPK ERAEISMLEGAVLDIRYGVSRIAYSKDFE TLKVDFLSKLPEMLKMFEDRLCHKTYLNG DHVTHPDFMLYDALDVVLYMDPMCLDAFP KLVCFKKRIEAIPQIDKYLKSSKYIAWPL QGWQATFGGGDHPPKSDGSTSGSGHHHHH HSAGLVPRGSTAIGMKETAAAKFERQHMD SPDLGTGGGSGIEGRGSMGYRGSEQAPEL ENLTVTEVGWDGLRLNWTAADQAYEHFII QVQEANKVEAARNLTVPGSLRAVDIPGLK AATPYTVSIYGVIQGYRTPVLSAEASTAS GLNDIFEAQKIEWHEGTHHHHHH | SEQ ID NO: 12 |

Example 2

Selection of Anti-TnC Antibodies from Generic Fab Libraries

Anti-TnC antibodies were selected from two different generic phage display libraries: DP88-4 (clone 18D4) and lambda-DP47 (clone 11C7).

Library Construction

The DP88-4 library was constructed on the basis of human germline genes using the V-domain pairing Vk1_5 (kappa light chain) and VH1_69 (heavy chain) comprising randomized sequence space in CDR3 of the light chain (L3, 3 different lengths) and CDR3 of the heavy chain (H3, 3 different lengths). Library generation was performed by assembly of 3 PCR-amplified fragments applying splicing by overlapping extension (SOE) PCR. Fragment 1 comprises the 5' end of the antibody gene including randomized L3, fragment 2 is a central constant fragment spanning from L3 to H3 whereas fragment 3 comprises randomized H3 and the 3' portion of the antibody gene. The following primer combinations were used to generate these library fragments for DP88-4 library: fragment 1 (forward primer LMB3 combined with reverse primers Vk1_5_L3r_S or Vk1_5_L3r_SY or Vk1_5_L3r_SPY), fragment 2 (forward primer RJH31 combined with reverse primer RJH32) and fragment 3 (forward primers DP88-v4-4 or DP88-v4-6 or DP88-v4-8 combined with reverse primer fdseqlong), respectively. PCR parameters for production of library fragments were 5 min initial denaturation at 94° C., 25 cycles of 1 min 94° C., 1 min 58° C., 1 min 72° C. and terminal elongation for 10 min at 72° C. For assembly PCR, using equimolar ratios of the gel-purified single fragments as template, parameters were 3 min initial denaturation at 94° C. and 5 cycles of 30 s 94° C., 1 min 58° C., 2 min 72° C. At this stage, outer primers (LMB3 and fdseqlong) were added and additional 20 cycles were performed prior to a terminal elongation for 10 min at 72° C. After assembly of sufficient amounts of full length randomized Fab constructs, they were digested NcoI/NheI and ligated into similarly treated acceptor phagemid vector. Purified ligations were used for ~60 transformations into electrocompetent E. coli TG1. Phagemid particles displaying the Fab library were rescued and purified by PEG/NaCl purification to be used for selections. These library construction steps were repeated three times to obtain a final library size of 4.4×10$^9$. Percentages of functional clones, as determined by C-terminal tag detection in dot blot, were 92.6% for the light chain and 93.7% for the heavy chain, respectively.

The lambda-DP47 library was constructed on the basis of human germline genes using the following V-domain pairings: V13_19 lambda light chain with VH3_23 heavy chain. The library was randomized in CDR3 of the light chain (L3) and CDR3 of the heavy chain (H3) and was assembled from 3 fragments by "splicing by overlapping extension" (SOE) PCR. Fragment 1 comprises the 5' end of the antibody gene including randomized L3, fragment 2 is a central constant fragment spanning from the end of L3 to the beginning of H3 whereas fragment 3 comprises randomized H3 and the 3' portion of the Fab fragment. The following primer combinations were used to generate library fragments for library: fragment 1 (LMB3—V1_3_19_L3r_V/V1_3_19_L3r_HV/V1_3_19_L3r_HLV), fragment 2 (RJH80-DP47CDR3_ba (mod)) and fragment 3 (DP47-v4-4/DP47-v4-6/DP47-v4-8—fdseqlong). PCR parameters for production of library fragments were 5 min initial denaturation at 94° C., 25 cycles of 60 sec 94° C., 60 sec 55° C., 60 sec 72° C. and terminal elongation for 10 min at 72° C. For assembly PCR, using equimolar ratios of the 3 fragments as template, parameters were 3 min initial denaturation at 94° C. and 5 cycles of 60 s 94° C., 60 sec 55° C., 120 sec 72° C. At this stage, outer primers were added and additional 20 cycles were performed prior to a terminal elongation for 10 min at 72° C.

After assembly of sufficient amounts of full length randomized Fab fragments, they were digested with NcoI/NheI alongside with similarly treated acceptor phagemid vector. 15 µg of Fab library insert were ligated with 13.3 µg of phagemid vector. Purified ligations were used for 60 transformations resulting in 1.5×10$^9$ transformants. Phagemid particles displaying the Fab library were rescued and purified by PEG/NaCl purification to be used for selections.

Phage Display Selections & ELISA Screening

Human GST-fused TNC fn5 A1234 BC fn6 as antigen for the phage display selections was expressed in *E. coli* and in vivo site-specifically biotinylated via co-expression of BirA biotin ligase at the avi-tag recognition sequence located at the C-terminus of the fusion protein (production of antigens according to Example 1, sequences derived from Table 4). This antigen comprises the human TnC extra splice domains A1, A2, A3, A4, B, and C, located between the two fibronectin type III domains 5 and 6. The phage display selections aimed at selecting binders to any of these extra splice domains and determine the domain specificity in a subsequent step by surface plasmon resonance using additional antigen constructs comprising fewer extra splice domains.

Selection rounds (biopanning) were performed in solution according to the following pattern: 1. Pre-clearing of ~10$^{12}$ phagemid particles with an unrelated GST-fusion protein that also carried an avi-tag and His6-tag similar to the TnC target antigen to deplete the libraries of antibodies recognizing the three different tags, 2. incubation of the pre-cleared phagemid particles in the supernatant with 100 nM biotinylated human GST-fused TNC fn5 A1234 BC fn6 for 0.5 hours in the presence of an unrelated non-biotinylated GST-fusion protein for further depletion of tag-binders in a total volume of 1 ml, 3. capture of biotinylated human GST-fused TNC fn5 A1234 BC fn6 and attached specifically binding phage by transfer to 4 wells of a neutravidin pre-coated microtiter plate for 10 minutes (in rounds 1 & 3), 4. washing of respective wells using 5× PBS/Tween20 and 5×PBS, 5. elution of phage particles by addition of 250 µl 100 mM TEA (triethylamine) per well for 10 minutes and neutralization by addition of 500 µl 1 M Tris/HCl pH 7.4 to the pooled eluates from 4 wells, 6. re-infection of log-phase *E. coli* TG1 cells with the supernatant of eluted phage particles, infection with helperphage VCSM13, incubation on a shaker at 30° C. over night and subsequent PEG/NaCl precipitation of phagemid particles to be used in the next selection round. Selections were carried out over 3 rounds using constant antigen concentrations of 100 nM. In round 2, in order to avoid enrichment of binders to neutravidin, capture of antigen:phage complexes was performed by addition of 5.4×10$^7$ streptavidin-coated magnetic beads. Specific binders were identified by ELISA after rounds 2 and 3 as follows: 100 µl of 100 nM biotinylated human GST-fused TNC fn5 A1234 BC fn6 were coated on neutravidin plates. Fab-containing bacterial supernatants were added and binding Fabs were detected via their Flag-tags using an anti-Flag/HRP secondary antibody. Clones exhibiting signals on human GST-fused TNC fn5 A1234 BC fn6 and being negative on an unrelated GST-fusion protein carrying the same tags as the target, were short-listed for further analyses. They were bacterially expressed in a 0.5 liter culture volume, affinity purified and further characterized by SPR-analysis using BioRad's ProteOn XPR36 biosensor to test cross-reactivity to murine TnC and to determine which extra splice domains the antibodies recognize.

SPR-Analysis Using BioRad's ProteOn XPR36 Biosensor

Affinities ($K_D$) of selected clones were measured by surface plasmon resonance (SPR) using a ProteOn XPR36 instrument (Biorad) at 25° C. with biotinylated human and murine TnC antigens immobilized on NLC chips by neutravidin capture. Immobilization of antigens (ligand): Recombinant antigens were diluted with PBST (10 mM phosphate, 150 mM sodium chloride pH 7.4, 0.005% Tween 20) to 10m/ml, then injected at 30 µl/minute in vertical orientation. Injection of analytes: For 'one-shot kinetics' measurements, injection direction was changed to horizontal orientation, two-fold dilution series of purified Fab were injected simultaneously along separate channels 1-5, with association times of 200 s, and dissociation times of 240 s, respectively. Buffer (PBST) was injected along the sixth channel to provide an "in-line" blank for referencing. Association rate constants ($k_{on}$) and dissociation rate constants ($k_{off}$) were calculated using a simple one-to-one Langmuir binding model in ProteOn Manager v3.1 software by simultaneously fitting the association and dissociation sensorgrams. The equilibrium dissociation constant ($K_D$) was calculated as the ratio $k_{off}/k_{on}$. Table 5 lists the equilibrium dissociation constants ($K_D$) of the two selected clones 18D4 and 11C7 for several TnC antigens differing in species and composition of the extra splice domains.

TABLE 5

Equilibrium dissociation constants ($K_D$) for clones 18D4 and 11C7

| antigen | clone 18D4 $K_D$ [nM] | clone 11C7 $K_D$ [nM] |
|---|---|---|
| GST huTNC fn5 A1234 BC fn6 B | 4.0 | 2.3 |
| GST huTNCfn5 mu A124 BC hu fn6 B | 11.2 | 1.9 |
| GST TNC hu fn5 B-C fn6 B | n.a. | 1.0 |
| GST huTNC fn5 A1234 fn6 B | 5.0 | n.a. |
| huTNC A4 B | 2.0 | n.a. |
| huTNC A1 B | 5.6 | n.a. |

TABLE 6

DNA sequence of generic phage-displayed DP88-4 library (Vk1_5/VH1_69) template used for PCRs

| Construct | Base pair sequence | SEQ ID NO |
|---|---|---|
| pRJH33 library template DP88-4 library; complete Fab coding region comprising PelB leader sequence + Vk1_5 kappa V-domain + CL constant domain for light chain and PelB + VH1_69 V-domain + CH1 constant domain for heavy chain) | ATGAAATACCTATTGCCTACGGCAGC CGCTGGATTGTTATTACTCGCGGCCC AGCCGGCCATGGCCGACATCCAGATG ACCCAGTCTCCTTCCACCCTGTCTGC ATCTGTAGGAGACCGTGTCACCATCA CTTGCCGTGCCAGTCAGAGTATTAGT AGCTGGTTGGCCTGGTATCAGCAGAA ACCAGGGAAAGCCCCTAAGCTCCTGA TCTATGATGCCTCCAGTTTGGAAAGT GGGGTCCCATCACGTTTCAGCGGCAG TGGATCCGGGACAGAATTCACTCTCA CCATCAGCAGCTTGCAGCCTGATGAT TTTGCAACTTATTACTGCCAACAGTA TAATAGTTATTCTACGTTTGGCCAGG GCACCAAAGTCGAGATCAAGCGTACG GTGGCTGCACCATCTGTCTTCATCTT CCCGCCATCTGATGAGCAGTTGAAAT CTGGAACTGCCTCTGTTGTGTGCCTG CTGAATAACTTCTATCCCAGAGAGGC CAAAGTACAGTGGAAGGTGGATAACG CCCTCCAATCGGGTAACTCCCAGGAG AGTGTCACAGAGCAGGACAGCAAGGA CAGCACCTACAGCCTCAGCAGCACCC TGACGCTGAGCAAAGCAGACTACGAG AAACACAAAGTCTACGCCTGCGAAGT CACCCATCAGGGCCTGAGCTCGCCCG TCACAAAGAGCTTCAACAGGGGAGAG TGTGGAGCCGCAGAACAAAAACTCAT CTCAGAAGAGGATCTGAATGGAGCCG CAGACTACAAGGACGACGACGACAAG GGTGCCGCATAATAAGGCGCGCCAAT TCTATTTCAAGGAGACAGTCATATGA AATACCTGCTGCCGACCGCTGCTGCT GGTCTGCTGCTCCTCGCTGCCCAGCC GGCGATGGCCCAGGTGCAATTGGTGC AGTCTGGGGCTGAGGTGAAGAAGCCT GGGTCCTCGGTGAAGGTCTCCTGCAA GGCCTCCGGAGGCACATTCAGCAGCT ACGCTATAAGCTGGGTGCGACAGGCC CCTGGACAAGGGCTCGAGTGGATGGG AGGGATCATCCCTATCTTTGGTACAG CAAACTACGCACAGAAGTTCCAGGGC AGGGTCACCATTACTGCAGACAAATC CACGAGCACAGCCTACATGGAGCTGA GCAGCCTGAGATCTGAGGACACCGCC GTGTATTACTGTGCAGAGACTATCCC AGGCGGTTACTATGTTATGGATGCCT GGGGCCAAGGGACCACCGTGACCGTC TCCTCAGCTAGCACCAAAGGCCCATC GGTCTTCCCCCTGGCACCCTCCTCCA AGAGCACCTCTGGGGGCACAGCGGCC CTGGGCTGCCTGGTCAAGGACTACTT CCCCGAACCGGTGACGGTGTCGTGGA ACTCAGGCGCCCTGACCAGCGGCGTG CACACCTTCCCGGCTGTCCTACAGTC CTCAGGACTCTACTCCCTCAGCAGCG TGGTGACCGTGCCCTCCAGCAGCTTG GGCACCCAGACCTACATCTGCAACGT GAATCACAAGCCCAGCAACACCAAAG TGGACAAGAAAGTTGAGCCCAAATCT TGTGACGCGGCCGCAAGCACTAGTGC CCATCACCATCACCATCACGCCGCGG CA | SEQ ID NO: 13 |

TABLE 7

Base pair sequence of DP88-4 library (Vk1_5/VH1_69) germline template

| Construct | Base pair sequence | SEQ ID NO |
|---|---|---|
| Fab light chain V1_5 | GACATCCAGATGACCCAGTCTCCTTCC ACCCTGTCTGCATCTGTAGGAGACCGT GTCACCATCACTTGCCGTGCCAGTCAG AGTATTAGTAGCTGGTTGGCCTGGTAT CAGCAGAAACCAGGGAAAGCCCCTAAG CTCCTGATCTATGATGCCTCCAGTTTG GAAAGTGGGGTCCCATCACGTTTCAGC GGCAGTGGATCCGGGACAGAATTCACT CTCACCATCAGCAGCTTGCAGCCTGAT GATTTTGCAACTTATTACTGCCAACAG TATAATAGTTATTCTACGTTTGGCCAG GGCACCAAAGTCGAGATCAAGCGTACG GTGGCTGCACCATCTGTCTTCATCTTC CCGCCATCTGATGAGCAGTTGAAATCT GGAACTGCCTCTGTTGTGTGCCTGCTG AATAACTTCTATCCCAGAGAGGCCAAA GTACAGTGGAAGGTGGATAACGCCCTC CAATCGGGTAACTCCCAGGAGAGTGTC ACAGAGCAGGACAGCAAGGACAGCACC TACAGCCTCAGCAGCACCCTGACGCTG AGCAAAGCAGACTACGAGAAACACAAA GTCTACGCCTGCGAAGTCACCCATCAG GGCCTGAGCTCGCCCGTCACAAAGAGC TTCAACAGGGGAGAGTGTGGAGCCGCA GAACAAAAACTCATCTCAGAAGAGGAT CTGAATGGAGCCGCAGACTACAAGGAC GACGACGACAAGGGTGCCGCA | SEQ ID NO: 14 |
| Fab heavy chain VH1_69 | CAGGTGCAATTGGTGCAGTCTGGGGCT GAGGTGAAGAAGCCTGGGTCCTCGGTG AAGGTCTCCTGCAAGGCCTCCGGAGGC ACATTCAGCAGCTACGCTATAAGCTGG GTGCGACAGGCCCCTGGACAAGGGCTC GAGTGGATGGGAGGGATCATCCCTATC TTTGGTACAGCAAACTACGCACAGAAG TTCCAGGGCAGGGTCACCATTACTGCA GACAAATCCACGAGCACAGCCTACATG GAGCTGAGCAGCCTGAGATCTGAGGAC ACCGCCGTGTATTACTGTGCAGAGACTA TCCCCAGGCGGTTACTATGTTATGGAT GCCTGGGGCCAAGGGACCACCGTGACC GTCTCCTCAGCTAGCACCAAAGGCCCA TCGGTCTTCCCCCTGGCACCCTCCTCC AAGAGCACCTCTGGGGGCACAGCGGCC CTGGGCTGCCTGGTCAAGGACTACTTC CCCGAACCGGTGACGGTGTCGTGGAAC TCAGGCGCCCTGACCAGCGGCGTGCAC ACCTTCCCGGCTGTCCTACAGTCCTCA GGACTCTACTCCCTCAGCAGCGTGGTG ACCGTGCCCTCCAGCAGCTTGGGCACC CAGACCTACATCTGCAACGTGAATCAC AAGCCCAGCAACACCAAAGTGGACAAG | SEQ ID NO: 15 |

TABLE 7-continued

Base pair sequence of DP88-4 library (Vk1_5/VH1_69) germline template

| Construct | Base pair sequence | SEQ ID NO |
|---|---|---|
| | AAAGTTGAGCCCAAATCTTGTGACGCG GCCGCAAGCACTAGTGCCCATCACCAT CACCATCACGCCGCGGCA | |

TABLE 8

Amino acid sequence of DP88-4 library (Vk1_5/VH1_69) germline template

| Construct | Base pair sequence | SEQ ID NO |
|---|---|---|
| Fab light chain Vk1_5 | DIQMTQSPSTLSASVGDRVTITCRASQSI SSWLAWYQQKPGKAPKLLIYDASSLESGV PSRFSGSGSGTEFTLTISSLQPDDFATYY CQQYNSYSTFGQGTKVEIKRTVAAPSVFI FPPSDEQLKSGTASVVCLLNNFYPREAKV QWKVDNALQSGNSQESVTEQDSKDSTYSL SSTLTLSKADYEKHKVYACEVTHQGLSSP VTKSFNRGECGAAEQKLISEEDLNGAADY KDDDDKGAA | SEQ ID NO: 16 |
| Fab heavy chain VH1_69 (DP88) | QVQLVQSGAEVKKPGSSVKVSCKASGGTF SSYAISWVRQAPGQGLEWMGGIIPIFGTA NYAQKFQGRVTITADKSTSTAYMELSSLR SEDTAVYYCARLSPGGYYVMDAWGQGTTV TVSSASTKGPSVFPLAPSSKSTSGGTAAL GCLVKDYFPEPVTVSWNSGALTSGVHTFP AVLQSSGLYSLSSVVTVPSSSLGTQTYIC NVNHKPSNTKVDKKVEPKSCDAAASTSAH HHHHHAAA | SEQ ID NO: 17 |

TABLE 9

Primer sequences used for generation of DP88-4 library (Vk1_5/VH1_69)

| Primer name | Primer sequence 5'-3' | SEQ ID NO |
|---|---|---|
| LMB3 | CAGGAAACAGCTATGACCATG ATTAC | SEQ ID NO: 76 |
| Vk1_5_L3r_S | CTCGACTTTGGTGCCCTGGCC AAACGT*SBAATA*CGAATTATA CTGTTGGCAGTAATAAGTTGC AAAATCAT | SEQ ID NO: 77 |
| Vk1_5_L3r_SY | CTCGACTTTGGTGCCCTGGCC AAACGT*MHRSGR*ATACGAATT ATACTGTTGGCAGTAATAAGT TGCAAAATCAT | SEQ ID NO: 78 |
| Vk1_5_L3r_SPY | CTCGACTTTGGTGCCCTGGCC AAACGT*MHHMSSSGR*ATACGA ATTATACTGTTGGCAGTAATA AGTTGCAAAATCAT | SEQ ID NO: 79 |
| RJH31 | ACGTTTGGCCAGGGCACCAAA GTCGAG | SEQ ID NO: 80 |
| RJH32 | TCTCGCACAGTAATACACGGC GGTGTCC | SEQ ID NO: 81 |
| DP88-v4-4 | GGACACCGCCGTGTATTACTG TGCGAGA-1-2-2-3-4-GAC- TAC-TGGGGCCAAGGGACCAC CGTGACCGTCTCC | SEQ ID NO: 82 |

TABLE 9-continued

Primer sequences used for generation of DP88-4 library (Vk1_5/VH1_69)

| Primer name | Primer sequence 5'-3' | SEQ ID NO |
|---|---|---|
| DP88-v4-6 | GGACACCGCCGTGTATTACTG TGCGAGA-1-2-2-2-2-3-4- GAC-TAC-TGGGGCCAAGGGA CCACCGTGACCGTCTCC | SEQ ID NO: 83 |
| DP88-v4-8 | GGACACCGCCGTGTATTACTG TGCGAGA-1-2-2-2-2-2-2- 3-4-GAC-TAC-TGGGGCCAA GGGACCACCGTGACCGTCTCC | SEQ ID NO: 84 |
| fdseqlong | GACGTTAGTAAATGAATTTTC TGTATGAGG | SEQ ID NO: 85 |

Underlined bases: 60% given sequence and 40% N; Bases in italics: 60% given sequence and 40% M.
1: G/D = 20%, E/V/S = 10%, A/P/R/L/T/Y = 5%;
2: G/Y/S = 15%, A/D/T/R/P/L/V/N/W/F/I/E = 4,6%;
3: G/A/Y = 20%, P/W/S/D/T = 8%;
4: F = 46%, L/M = 15%, G/I/Y = 8%.

TABLE 10

DNA sequence of generic phage-displayed lambda-DP47 library (Vl3_19/VH3_23) template used for PCRs

| Construct | Base pair sequence | SEQ ID NO |
|---|---|---|
| pRJH53 library template of lambda-DP47 library Vl3_19/VH3_23; complete Fab coding region comprising PelB leader sequence + Vl3_19 lambda V-domain + CL constant domain for light chain and PelB + VH3_23 V-domain + CH1 constant domain for heavy chain including tags | ATGAAATACCTATTGCCTACGGCAGCC GCTGGATTGTTATTACTCGCGGCCCAG CCGGCCATGGCCTCGTCTGAGCTGACT CAGGACCCTGCTGTGTCTGTGGCCTTG GGACAGACAGTCAGGATCACATGCCAA GGAGACAGCCTCAGAAGTTATTATGCA AGCTGGTACCAGCAGAAGCCAGGACAG GCCCCTGTACTTGTCATCTATGGTAAA AACAACCGGCCCTCAGGGATCCCAGAC CGATTCTCTGGCTCCAGCTCAGGAAAC ACAGCTTCCTTGACCATCACTGGGGCT CAGGCGGAAGATGAGGCTGACTATTAC TGTAACTCCCGTGATAGTAGCGGTAAT CATGTGGTATTCGGCGGAGGGACCAAG CTGACCGTCCTAGGACAACCCAAGCGT GCCCCCAGCGTGACCCTGTTCCCCCCC AGCAGCGAGGAATTGCAGGCCAACAAG GCCACCCTGGTCTGCCTGATCAGCGAC TTCTACCCAGGCGCCGTGACCGTGGCC TGGAAGGCCGACAGCAGCCCCGTGAAG GCCGGCGTGGAGACCACCACCCCCAGC AAGCAGAGCAACAACAAGTACGCCGCC AGCAGCTACCTGAGCCTGACCCCCGAG CAGTGGAAGAGCCACAGGTCCTACAGC TGCCAGGTGACCCACGAGGGCAGCACC GTGGAGAAAACCGTGGCCCCCACCGAG TGCAGCGGAGCCGCAGAACAAAAACTC ATCTCAGAAGAGGATCTGAATGGAGCC GCAGACTACAAGGACGACGACGACAAG GGTGCCCATAATAAGGCGCGCCAATTC TATTTCAAGGAGACAGTCATATGAAA TACCTGCTGCCGACCGCTGCTGCTGGT CTGCTGCTCCTCGCTGCCCAGCCGGCC ATGGCCGAGGTGCAATTGCTGGAGTCT GGGGGAGGCTTGGTACAGCCTGGGGGG TCCCTGAGACTCTCCTGTGCAGCCTCC GGATTCACCTTTAGCAGTTATGCCATG AGCTGGGTCCGCCAGGCTCCAGGGAAG GGGCTGGAGTGGGTCTCAGCTATTAGT GGTAGTGGTGGTAGCACATACTACGCA GACTCCGTGAAGGGCCGGTTCACCATC TCCAGAGACAATTCCAAGAACACGCTG | SEQ ID NO: 18 |

TABLE 10-continued

DNA sequence of generic phage-displayed lambda-DP47 library (Vl3_19/VH3_23) template used for PCRs

| Construct | Base pair sequence | SEQ ID NO |
|---|---|---|
| | TATCTGCAGATGAACAGCCTGAGAGCC<br>GAGGACACGGCCGTATATTACTGTGCG<br>AAACCGTTTCCGTATTTTGACTACTGG<br>GGCCAAGGAACCCTGGTCACCGTCTCG<br>AGTGCTAGCACCAAAGGCCCATCGGTC<br>TTCCCCCTGGCACCCTCCTCCAAGAGC<br>ACCTCTGGGGGCACAGCGGCCCTGGGC<br>TGCCTGGTCAAGGACTACTTCCCCGAA<br>CCGGTGACGGTGTCGTGGAACTCAGGC<br>GCCCTGACCAGCGGCGTGCACACCTTC<br>CCGGCTGTCCTACAGTCCTCAGGACTC<br>TACTCCCTCAGCAGCGTGGTGACCGTG<br>CCCTCCAGCAGCTTGGGCACCCAGACC<br>TACATCTGCAACGTGAATCACAAGCCC<br>AGCAACACCAAAGTGGACAAGAAAGTT<br>GAGCCCAAATCTTGTGACGCGGCCGCA<br>AGCACTAGTGCCCATCACCATCACCAT<br>CACGCCGCGGCA | |

TABLE 11

Base pair sequence of lambda-DP47 library (Vl3_19/VH3_23) germline template

| Construct | Base pair sequence | SEQ ID NO |
|---|---|---|
| Fab light chain V13_19 | TCGTCTGAGCTGACTCAGGACCCTGCT<br>GTGTCTGTGGCCTTGGGACAGACAGTC<br>AGGATCACATGCCAAGGAGACAGCCTC<br>AGAAGTTATTATGCAAGCTGGTACCAG<br>CAGAAGCCAGGACAGGCCCCTGTACTT<br>GTCATCTATGGTAAAAACAACCGGCCC<br>TCAGGGATCCCAGACCGATTCTCTGGC<br>TCCAGCTCAGGAAACACAGCTTCCTTG<br>ACCATCACTGGGGCTCAGGCGGAAGAT<br>GAGGCTGACTATTACTGTAACTCCCGT<br>GATAGTAGCGGTAATCATGTGGTATTC<br>GGCGGAGGGACCAAGCTGACCGTCCTA<br>GGACAACCCAAGGCTGCCCCCAGCGTG<br>ACCCTGTTCCCCCCCAGCAGCGAGGAA<br>TTGCAGGCCAACAAGGCCACCCTGGTC<br>TGCCTGATCAGCGACTTCTACCCAGGC<br>GCCGTGACCGTGGCCTGGAAGGCCGAC<br>AGCAGCCCCGTGAAGGCCGGCGTGGAG<br>ACCACCACCCCCAGCAAGCAGAGCAAC<br>AACAAGTACGCCGCCAGCAGCTACCTG<br>AGCCTGACCCCCGAGCAGTGGAAGAGC<br>CACAGGTCCTACAGCTGCCAGGTGACC<br>CACGAGGGCAGCACCGTGGAGAAAACC<br>GTGGCCCCCACCGAGTGCAGCGGAGCC<br>GCAGAACAAAACTCATCTCAGAAGAG<br>GATCTGAATGGAGCCGCAGACTACAAG<br>GACGACGACGACAAGGGTGCCGCA | SEQ ID NO: 19 |
| Fab heavy chain VH3_23 | GAGGTGCAATTGCTGGAGTCTGGGGGA<br>GGCTTGGTACAGCCTGGGGGGTCCCTG<br>AGACTCTCCTGTGCAGCCTCCGGATTC<br>ACCTTTAGCAGTTATGCCATGAGCTGG<br>GTCCGCCAGGCTCCAGGGAAGGGGCTG<br>GAGTGGGTCTCAGCTATTAGTGGTAGT<br>GGTGGTAGCACATACTACGCAGACTCC<br>GTGAAGGGCCGGTTCACCATCTCCAGA<br>GACAATTCCAAGAACACGCTGTATCTG<br>CAGATGAACAGCCTGAGAGCCGAGGAC | SEQ ID NO: 20 |

TABLE 11-continued

Base pair sequence of lambda-DP47 library (Vl3_19/VH3_23) germline template

| Construct | Base pair sequence | SEQ ID NO |
|---|---|---|
| | ACGGCCGTATATTACTGTGCGAAACCG<br>TTTCCGTATTTTGACTACTGGGGCCAA<br>GGAACCCTGGTCACCGTCTCGAGTGCT<br>AGCACCAAAGGCCCATCGGTCTTCCCC<br>CTGGCACCCTCCTCCAAGAGCACCTCT<br>GGGGGCACAGCGGCCCTGGGCTGCCTG<br>GTCAAGGACTACTTCCCCGAACCGGTG<br>ACGGTGTCGTGGAACTCAGGCGCCCTG<br>ACCAGCGGCGTGCACACCTTCCCGGCT<br>GTCCTACAGTCCTCAGGACTCTACTCC<br>CTCAGCAGCGTGGTGACCGTGCCCTCC<br>AGCAGCTTGGGCACCCAGACCTACATC<br>TGCAACGTGAATCACAAGCCCAGCAAC<br>ACCAAAGTGGACAAGAAAGTTGAGCCC<br>AAATCTTGTGACGCGGCCGCAAGCACT<br>AGTGCCCATCACCATCACCATCACGCC<br>GCGGCA | |

TABLE 12

Amino acid sequence of lambda-DP47 library (Vl3_19/VH3_23) germline template

| Construct | Base pair sequence | SEQ ID NO |
|---|---|---|
| Fab light chain V13_19 | SSELTQDPAVSVALGQTVRITCQGDSL<br>RSYYASWYQQKPGQAPVLVIYGKNNRP<br>SGIPDRFSGSSSGNTASLTITGAQAED<br>EADYYCNSRDSSGNHVVFGGGTKLTVL<br>GQPKAAPSVTLFPPSSEELQANKATLV<br>CLISDFYPGAVTVAWKADSSPVKAGVE<br>TTTPSKQSNNKYAASSYLSLTPEQWKS<br>HRSYSCQVTHEGSTVEKTVAPTECSGA<br>AEQKLISEEDLNGAADYKDDDDKGAA | SEQ ID NO: 21 |
| Fab heavy chain VH3_23 (DP47) | EVQLLESGGGLVQPGGSLRLSCAASGF<br>TFSSYAMSWVRQAPGKGLEWVSAISGS<br>GGSTYYADSVKGRFTISRDNSKNTLYL<br>QMNSLRAEDTAVYYCAKPFPYFDYWGQ<br>GTLVTVSSASTKGPSVFPLAPSSKSTS<br>GGTAALGCLVKDYFPEPVTVSWNSGAL<br>TSGVHTFPAVLQSSGLYSLSSVVTVPS<br>SSLGTQTYICNVNHKPSNTKVDKKVEP<br>KSCDAAASTSAHHHHHHAAA | SEQ ID NO: 22 |

TABLE 13

| Primer sequences used for generation of lambda-DP47 library (Vl3_19/VH3_23) | | |
|---|---|---|
| Primer name | Primer sequence 5'-3' | SEQ ID NO |
| LMB3 | CAGGAAACAGCTATGACCATGATTAC | SEQ ID NO: 76 |
| Vl_3_19_L3r_V | GGACGGTCAGCTTGGTCCCTCCGCCG<br>AATAC V***HV*** A***TT*** A***CC*** G***CT*** A***CT*** A***TC*** A***CG***<br>GGAGTTACAGTAATAGTCAGCCTCATCTTCCGC<br>underlined: 60% original base and 40% randomization as M<br>bold and italic: 60% original base and 40% randomization as N | SEQ ID NO: 86 |
| Vl_3_19_L3r_HV | GGACGGTCAGCTTGGTCCCTCCGCCGAATAC<br>C***MM*** A***TG*** A***TG*** A***CC*** G***CT*** A***CT*** A***TC*** A***CG***<br>GGAGTTACAGTAATAGTCAGCCTCATCTTCCGC<br>underlined: 60% original base and 40% randomization as M<br>bolded and italic: 60% original base and 40% randomization as N | SEQ ID NO: 87 |
| Vl_3_19_L3r_HLV | GGACGGTCAGCTTGGTCCCTCCGCCGAATAC<br>R***HM*** V***WG*** A***TG*** A***TT*** A***CC*** G***CT*** A***CT*** A***TC*** A***CG***<br>GGAGTTACAGTAATAGTCAGCCTCATCTTCCGC<br>underlined: 60% original base and 40% randomization as M<br>bolded and italic: 60% original base and 40% randomization as N | SEQ ID NO: 88 |
| RJH80 | TTCGGCGGAGGGACCAAGCTGACCGTCC | SEQ ID NO: 89 |
| DP47CDR3_ba (mod.) | CGCACAGTAATATACGGCCGTGTCC | SEQ ID NO: 90 |
| DP47-v4-4 | CGAGGACACGGCCGTATATTACTGTGCG-5-1-2-2-3-4-GAC-TAC-TGGGGCCAAGGAACCCTGGTCACCGTCTCG | SEQ ID NO: 91 |
| DP47-v4-6 | CGAGGACACGGCCGTATATTACTGTGCG-5-1-2-2-2-2-3-4-GAC-TAC-TGGGGCCAAGGAACCCTGGTCACCGTCTCG | SEQ ID NO: 92 |
| DP47-v4-8 | CGAGGACACGGCCGTATATTACTGTGCG-5-1-2-2-2-2-2-2-3-4-GAC-TAC-TGGGGCCAAGGAACCCTGGTCACCGTCTCG | SEQ ID NO: 93 |
| fdseqlong | GACGTTAGTAAATGAATTTTCTGTATGAGG | SEQ ID NO: 85 |

Trinucleotide mixtures in randomized primers:
1 (G/D = 20%, E/V/S = 10%, A/P/R/L/T/Y = 5%);
2 (G/Y/S = 15%, A/D/T/R/P/L/V/N/W/F/I/E = 4,6%);
3 (G/A/Y = 20, P/W/S/D/T = 8%);
4 (F = 46%, L/M = 15%, G/I/Y = 8%);
5 (K = 70%, R = 30%)

Example 3

Cloning of Variable Antibody Domains into Expression Vectors

The variable regions of heavy and light chain DNA sequences of the selected anti-TnC binders (Table 14 to Table 19) were subcloned in frame with either the constant heavy chain or the constant light chain of human IgG1. The antibodies have been prepared either as wild type human IgG1 backbone or as variant containing Pro329Gly, Leu234Ala and Leu235Ala mutations, which have been introduced to abrogate binding to Fc gamma receptors according to the method described in International Patent Appl. Publ. No. WO 2012/130831 A1.

The CDR sequences of the anti-TnC binder are shown in Table 16 to Table 19. The base pair and amino acid sequences of the anti-TnC IgGs are shown in Table 20 and Table 21. The base pair and amino acid sequences of the anti-TnC P319GLALA IgGs are shown in Table 22 and Table 23. All antibody-encoding sequences were cloned into an expression vector, which drives transcription of the insert with a chimeric MPSV promoter and contains a synthetic polyA signal sequence located at the 3' end of the CDS. In addition, the vector contains an EBV OriP sequence for episomal maintenance of the plasmid.

LCDR3 of clone 11C7 (NSINSTRNEV), as selected by phage display, contains a potential N-glycosylation site, i.e. NST, which can potentially be removed by amino acid substitutions to facilitate production of a homogeneous product. At the same time, binding to the target should be retained. N (position 1) could preferentially be substituted by Q, S or T. Alternatively, S (position 2) could be replaced by P. Alternatively, T (position 3) could be substituted preferentially by G or N or by any other proteinogenic amino acid except for S or C. Whichever substitution(s) would be the best, can be determined empirically by those skilled in the art.

TABLE 14

Variable region base pair sequences for phage-derived anti-TnC antibodies

| Clone | Chain | Base pair sequence | SEQ ID NO |
|---|---|---|---|
| 18D4 | VL | GACATCCAGATGACCCAGTCTCCATCCACCCTGTCTGCATCTGTAGGAGACCGTGTCACCATCACTTGCCGTGCCAGTCAGAGTATTAGTAGCTGGTTGGCCTGGTATCAGCAGAAACCAGGGAAAGCCCCTAAGCTCCTGATCTATGATGCCTCCAGTTTGGAAAGTGGGGTCCCATCACGTTTCAGCGGCAGTGGATCCGGGACAGAATTCACTCTCACCATCAGCAGCTTGCAGCCTGATGATTTTGCAACTTATTACTGCCAACAGAATAAGAAGTTTCCTTCGGGGACGTTTGGCCAGGGCACCAAAGTCGAGATCAAG | SEQ ID NO: 23 |
| | VH | CAGGTGCAATTGGTGCAGTCTGGGGCTGAGGTGAAGAAGCCTGGGTCCTCGGTGAAGGTCTCCTGCAAGGCCTCCGGAGGCACATTCAGCAGCTACGCTATAAGCTGGGTGCGACAGGCCCCTGGACAAGGGCTCGAGTGGATGGGAGGGATCATCCCTATCTTTGGTACAGCAAACTACGCACAGAAGTTCCAGGGCAGGGTCACCATTACTGCAGACAAATCCACGAGCACAGCCTACATGGAGCTGAGCAGCCTGAGATCTGAGGACACCGCCGTGTATTACTGTGCGAAAGGTAACTTCTACGGTGGTCTGGACTACTGGGGCCAAGGGACCACCGTGACCGTCTCCTCA | SEQ ID NO: 24 |
| 11C7 | VL | TCGTCTGAGCTGACTCAGGACCCTGCTGTGTCTGTGGCCTTGGGACAGACAGTCAGGGTCACATGCCAAGGAGACAGCCTCAGAAGTTATTATGCAAGCTGGTACCAGCAGAAGCCAGGACAGGCCCCTGTACTTGTCATCTATGGTAAAAACAACCGGCCCTCAGGGATCCCAGACCGATTCTCTGGCTCCAGCTCAGGAAACACAGCTTCCTTGACCATCACTGGGGCTCAGGCGGAAGATGAGGCTGACTATTACTGTAACTCCATTAATAGTACTCGTAATGAGGTATTCGGCGGAGGGACCAAGCTGACCGTCCTA | SEQ ID NO: 25 |
| | VH | GAGGTGCAATTGTTGGAGTCTGGGGGAGGCTTGGTACAGCCTGGGGGGTCCCTGAGACTCTCCTGTGCAGCCTCCGGATTCACCTTTAGCAGTTATGCCATGAGCTGGGTCCGCCAGGCTCCAGGGAAGGGGCTGGAGTGGGTCTCAGCTATTAGCGGTAGTGGTGGTAGCACATACTACGCAGACTCCGTGAAGGGCCGGTTCACCATCTCCAAAGACAATTCCAAGAACACGCTGTATCTGCAGATGAACAGCCTGAGAGCCGAGGACACGGCCGTATATTACTGTGCGAAAACTTCTCCGCGTGTTCCGCTGGACTACTGGGGCCAAGGAACCCTGGTCACCGTCTCGAGT | SEQ ID NO: 26 |

TABLE 15

Variable region polypeptide sequences for phage-derived anti-TnC antibodies

| Clone | Chain | Polypeptide sequence | |
|---|---|---|---|
| 18D4 | VL | DIQMTQSPSTLSASVGDRVTITCRASQSISSWLAWYQQKPGKAPKLLIYDASSLESGVPSRFSGSGSGTEFTLTISSLQPDDFATYYCQQNKKFPSGTFGQGTKVEIK | SEQ ID NO: 27 |
| | VH | QVQLVQSGAEVKKPGSSVKVSCKASGGTFSSYAISWVRQAPGQGLEWMGGIIPIFGTANYAQKFQGRVTITADKSTSTAYMELSSLRSEDTAVYYCAKGNFYGGLDYWGQGTTVTVSS | SEQ ID NO: 28 |

TABLE 15-continued

Variable region polypeptide sequences for phage-derived anti-TnC antibodies

| Clone | Chain | Polypeptide sequence | |
|---|---|---|---|
| 11C7 | VL | SSELTQDPAVSVALGQTVRVTCQGDSLRSYYASWYQQKPGQAPVLVIYGKNNRPSGIPDRFSGSSSGNTASLTITGAQAEDEADYYCNSINSTRNEVFGGGTKLTVL | SEQ ID NO: 29 |
| | VH | EVQLLESGGGLVQPGGSLRLSCAASGFTFSSYAMSWVRQAPGKGLEWVSAISGSGGSTYYADSVKGRFTISKDNSKNTLYLQMNSLRAEDTAVYYCAKTSPRVPLDYWGQGTLVTVSS | SEQ ID NO: 30 |

TABLE 16

CDR base pairs sequences of the anti-TnC antibody light chains

| clone | SEQ ID NO | LCDR1 | SEQ ID NO | LCDR2 | SEQ ID NO | LCDR3 |
|---|---|---|---|---|---|---|
| 18D4 | SEQ ID NO: 31 | CGTGCCAGTCAGAGTATTAGTAGCTGGTTGGCC | SEQ ID NO: 32 | GATGCCTCCAGTTTGGAAAGT | SEQ ID NO: 33 | CAACAGAATAAGAAGTTTCCTTCGGGACG |
| 11C7 | SEQ ID NO: 34 | CAAGGAGACAGCCTCAGAAGTTATTATGCAAGC | SEQ ID NO: 35 | GGTAAAAACAACCGGCCCTCA | SEQ ID NO: 36 | AACTCCATTAATAGTACTCGTAATGAGGTA |

TABLE 17

CDR polypeptides sequences of the anti-TnC antibody light chains

| clone | SEQ ID NO | LCDR1 | SEQ ID NO | LCDR2 | SEQ ID NO | LCDR3 |
|---|---|---|---|---|---|---|
| 18D4 | SEQ ID NO: 37 | RASQSISSWLA | SEQ ID NO: 38 | DASSLES | SEQ ID NO: 39 | QQNKKFPSGT |
| 11C7 | SEQ ID NO: 40 | QGDSLRSYYA | SEQ ID NO: 41 | GKNNRPS | SEQ ID NO: 42 | NSINSTRNEV |

TABLE 18

CDR base pairs sequences of the anti-TnC antibody heavy chains

| clone | SEQ ID NO | HCDR1 | SEQ ID NO | HCDR2 | SEQ ID NO | HCDR3 |
|---|---|---|---|---|---|---|
| 18D4 | SEQ ID NO: 43 | AGCTACGCTATAAGC | SEQ ID NO: 44 | GGGATCATCCCTATCTTTGGTACAGCAAAC | SEQ ID NO: 45 | GGTAACTTCTACGGTGGTCTGGACTAC |

TABLE 18-continued

CDR base pairs sequences of the anti-TnC antibody heavy chains

| clone | SEQ ID NO | HCDR1 | SEQ ID NO | HCDR2 | SEQ ID NO | HCDR3 |
|---|---|---|---|---|---|---|
| 11C7 | SEQ ID NO: 46 | GGATTCACCTTTAGCAGTTATGCCATGAGC | SEQ ID NO: 47 | GCTATTAGCGGTAGTGGTGGTAGCACATACTACGCAGACTCCGTGAAGGGC | SEQ ID NO: 48 | ACTTCTCCGCGTGTTCCGCTGGACTAC |

TABLE 19

CDR polypeptide sequences of the anti-TnC antibody heavy chains

| clone | SEQ ID NO | HCDR1 | SEQ ID NO | HCDR2 | SEQ ID NO | HCDR3 |
|---|---|---|---|---|---|---|
| 18D4 | SEQ ID NO: 49 | SYAIS | SEQ ID NO: 50 | GIIPIFGTANYAQKFQG | SEQ ID NO: 51 | GNFYGGLDY |
| 11C7 | SEQ ID NO: 52 | GFTFSSYAMS | SEQ ID NO: 53 | AISGSGGSTYYADSVKG | SEQ ID NO: 54 | TSPRVPLDY |

TABLE 20

Base pair sequences of anti-TnC clones in wild type human IgG1 format

| Clone | Chain | Base pair sequence | SEQ ID NO |
|---|---|---|---|
| 18D4 | Light chain | GACATCCAGATGACCCAGTCTCCATCCACCCTGTCTGCATCTGTAGGAGACCGTGTCACCATCACTTGCCGTGCCAGTCAGAGTATTAGTAGCTGGTTGGCCTGGTATCAGCAGAAACCAGGGAAAGCCCCTAAGCTCCTGATCTATGATGCCTCCAGTTTGGAAAGTGGGGTCCCATCACGTTTCAGCGGCAGTGGATCCGGGACAGAATTCACTCTCACCATCAGCAGCTTGCAGCCTGATGATTTTGCAACTTATTACTGCCAACAGAATAAGAAGTTTCCTTCGGGGACGTTTGGCCAGGGCACCAAAGTCGAGATCAAGCGTACGGTGGCTGCACCATCTGTCTTCATCTTCCCGCCATCTGATGAGCAGTTGAAATCTGGAACTGCCTCTGTTGTGTGCCTGCTGAATAACTTCTATCCCAGAGAGGCCAAAGTACAGTGGAAGGTGGATAACGCCCTCCAATCGGGTAACTCCCAGGAGAGTGTCACAGAGCAGGACAGCAAGGACAGCACCTACAGCCTCAGCAGCACCCTGACGCTGAGCAAAGCAGACTACGAGAAACACAAAGTCTACGCCTGCGAAGTCACCCATCAGGGCCTGAGCTCGCCCGTCACAAAGAGCTTCAACAGGGGAGAGTGT | SEQ ID NO: 55 |
| | Heavy chain | CAGGTGCAATTGGTGCAGTCTGGGGCTGAGGTGAAGAAGCCTGGGTCCTCGGTGAAGGTCTCCTGCAAGGCCTCCGGAGGCACATTCAGCAGCTACGCTATAAGCTGGGTGCGACAGGCCCCTGGACAAGGGCTCGAGTGGATGGGAGGGATCATCCCTATCTTTGGTACAGCAAACTACGCACAGAAGTTCCAGGGCAGGGTCACCATTACTGCAGACAAATCCACGAGCACAGCCTACATGGAGCTGAGCAGCCTGAGATCTGAGGACACCGCCGTGTATTACTGTGCAAAGGTAACTTCTACGGTGGTCTGGACTACTGGGGCCAAGGGACCACCGTGACCGTCTCCTCAGCTAGCACCAAGGGCCCATCGGTCTTCCCCCTGGCACCCTCCTCCAAGAGCACCTCTGGGGGCACAGCGGCCCTGGGCTGCCTGGTCAAGGACTACTTCCCCGAACCGGTGACGGTGTCGTGGAACTCAGGCGCCCTGACCAGCGGCGTGCACACCTTCCCGGCTGTCCTACAGTCCTCAGGACTCTACTCCCTCAGCAGCGTGGTGACCGTGCCCTCCAGCAGCTTGGGCACCCAGACCTACATCTGCAACGTGAATCACAAGCCCAGCAACACCAAGGTGGACAAGAAAGTTGAGCCCAAATCTTGTGACAAAACTCACACATGCCCACCGTGCCCAGCACCTGAACTCCTGGGGGGACCGTCAGTCTTCCTCTTCCCCCCAAAACCCAAGGACACCCTCATGATCTCCCGGACCCCTGAGGTCACATGCGTGGTGGTGGACGTGAGCCACGAAGACCCTGAGGTCAAGTTCAACTGGTACGTGGACGGCGTGGAGGTGCATAATGCCAAGACAAAGCCGCGGGAGGAGCAGTACAACAGCACGTACCGTGTGGTCAGCGTCCTCACCGTCCTGCACCAGGACTGGCTGAATGGCAAGGAGTACAAGTGCAAGGTCTCCAACAAAGCCCTCCCAGCCCCCATCGAGAAAAC | SEQ ID NO: 56 |

TABLE 20-continued

Base pair sequences of anti-TnC clones in wild type human IgG1 format

| Clone | Chain | Base pair sequence | SEQ ID NO |
|---|---|---|---|
| | | CATCTCCAAAGCCAAAGGGCAGCCCCGAGAACCACAG GTGTACACCCTGCCCCCATCCCGGGATGAGCTGACCA AGAACCAGGTCAGCCTGACCTGCCTGGTCAAAGGCTT CTATCCCAGCGACATCGCCGTGGAGTGGGAGAGCAAT GGGCAGCCGGAGAACAACTACAAGACCACGCCTCCCG TGCTGGACTCCGACGGCTCCTTCTTCCTCTACAGCAAG CTCACCGTGGACAAGAGCAGGTGGCAGCAGGGGAAC GTCTTCTCATGCTCCGTGATGCATGAGGCTCTGCACAA CCACTACACGCAGAAGAGCCTCTCCCTGTCTCCGGGTA AA | |
| 11C7 | Light chain | TCGTCTGAGCTGACTCAGGACCCTGCTGTGTCTGTGGC CTTGGGACAGACAGTCAGGGTCACATGCCAAGGAGAC AGCCTCAGAAGTTATTATGCAAGCTGGTACCAGCAGA AGCCAGGACAGGCCCCTGTACTTGTCATCTATGGTAA AAACAACCGGCCCTCAGGGATCCCAGACCGATTCTCT GGCTCCAGCTCAGGAAACACAGCTTCCTTGACCATCA CTGGGGCTCAGGCGGAAGATGAGGCTGACTATTACTG TAACTCCATTAATAGTACTCGTAATGAGGTATTCGGCG GAGGGACCAAGCTGACCGTCCTAGGTCAACCCAAGGC TGCCCCCAGCGTGACCCTGTTCCCCCCCAGCAGCGAG GAACTGCAGGCCAACAAGGCCACCCTGGTCTGCCTGA TCAGCGACTTCTACCCAGGCGCCGTGACCGTGGCCTG GAAGGCCGACAGCAGCCCCGTGAAGGCCGGCGTGGA GACCACCACCCCCAGCAAGCAGAGCAACAACAAGTAC GCCGCCAGCAGCTACCTGAGCCTGACCCCCGAGCAGT GGAAGAGCCACAGGTCCTACAGCTGCCAGGTGACCCA CGAGGGCAGCACCGTGGAGAAAACCGTGGCCCCCACC GAGTGCAGC | SEQ ID NO: 57 |
| | Heavy chain | GAGGTGCAATTGTTGGAGTCTGGGGGAGGCTTGGTAC AGCCTGGGGGGTCCCTGAGACTCTCCTGTGCAGCCTCC GGATTCACCTTTAGCAGTTATGCCATGAGCTGGGTCCG CCAGGCTCCAGGGAAGGGGCTGGAGTGGGTCTCAGCT ATTAGCGGTAGTGGTGGTAGCACATACTACGCAGACT CCGTGAAGGGCCGGTTCACCATCTCCAAAGACAATTC CAAGAACACGCTGTATCTGCAGATGAACAGCCTGAGA GCCGAGGACACGGCCGTATATTACTGTGCGAAAACTT CTCCGCGTGTTCCGCTGGACTACTGGGGCCAAGGAAC CCTGGTCACCGTCTCGAGTGCTAGCACCAAGGGCCCA TCGGTCTTCCCCCTGGCACCCTCCTCCAAGAGCACCTC TGGGGGCACAGCGGCCCTGGGCTGCCTGGTCAAGGAC TACTTCCCCGAACCGGTGACGGTGTCGTGGAACTCAG GCGCCCTGACCAGCGGCGTGCACACCTTCCCGGCTGTC CTACAGTCCTCAGGACTCTACTCCCTCAGCAGCGTGGT GACCGTGCCCTCCAGCAGCTTGGGCACCCAGACCTAC ATCTGCAACGTGAATCACAAGCCCAGCAACACCAAGG TGGACAAGAAAGTTGAGCCCAAATCTTGTGACAAAAC TCACACATGCCCACCGTGCCCAGCACCTGAACTCCTGG GGGGACCGTCAGTCTTCCTCTTCCCCCCAAAACCCAAG GACACCCTCATGATCTCCCGGACCCCTGAGGTCACATG CGTGGTGGTGGACGTGAGCCACGAAGACCCTGAGGTC AAGTTCAACTGGTACGTGGACGGCGTGGAGGTGCATA ATGCCAAGACAAAGCCGCGGGAGGAGCAGTACAACA GCACGTACCGTGTGGTCAGCGTCCTCACCGTCCTGCAC CAGGACTGGCTGAATGGCAAGGAGTACAAGTGCAAGG TCTCCAACAAAGCCCTCCCAGCCCCCATCGAGAAAAC CATCTCCAAAGCCAAAGGGCAGCCCCGAGAACCACAG GTGTACACCCTGCCCCCATCCCGGGATGAGCTGACCA AGAACCAGGTCAGCCTGACCTGCCTGGTCAAAGGCTT CTATCCCAGCGACATCGCCGTGGAGTGGGAGAGCAAT GGGCAGCCGGAGAACAACTACAAGACCACGCCTCCCG TGCTGGACTCCGACGGCTCCTTCTTCCTCTACAGCAAG CTCACCGTGGACAAGAGCAGGTGGCAGCAGGGGAAC GTCTTCTCATGCTCCGTGATGCATGAGGCTCTGCACAA CCACTACACGCAGAAGAGCCTCTCCCTGTCTCCGGGTA AA | SEQ ID NO: 58 |

TABLE 21

Polypeptide sequences of anti-TnC
clones in wild type human IgG1 format

| Clone | Chain | Polypeptide sequence | SEQ ID NO |
|---|---|---|---|
| 18D4 | Light chain | DIQMTQSPSTLSASVGDRVTITCRASQSISSWLAWYQQK PGKAPKLLIYDASSLESGVPSRFSGSGSGTEFTLTISSLQP DDFATYYCQQNKKFPSGTFGQGTKVEIKRTVAAPSVFIF PPSDEQLKSGTASVVCLLNNFYPREAKVQWKVDNALQ SGNSQESVTEQDSKDSTYSLSSTLTLSKADYEKHKVYA CEVTHQGLSSPVTKSFNRGEC | SEQ ID NO: 59 |
|  | Heavy chain | QVQLVQSGAEVKKPGSSVKVSCKASGGTFSSYAISWVR QAPGQGLEWMGGIIPIFGTANYAQKFQGRVTITADKSTS TAYMELSSLRSEDTAVYYCAKGNFYGGLDYWGQGTTV TVSSASTKGPSVFPLAPSSKSTSGGTAALGCLVKDYFPE PVTVSWNSGALTSGVHTFPAVLQSSGLYSLSSVVTVPSS SLGTQTYICNVNHKPSNTKVDKKVEPKSCDKTHTCPPC PAPELLGGPSVFLFPPKPKDTLMISRTPEVTCVVVDVSH EDPEVKFNWYVDGVEVHNAKTKPREEQYNSTYRVVSV LTVLHQDWLNGKEYKCKVSNKALPAPIEKTISKAKGQP REPQVYTLPPSRDELTKNQVSLTCLVKGFYPSDIAVEWE SNGQPENNYKTTPPVLDSDGSFFLYSKLTVDKSRWQQG NVFSCSVMHEALHNHYTQKSLSLSPGK | SEQ ID NO: 60 |
| 11C7 | Light chain | SSELTQDPAVSVALGQTVRVTCQGDSLRSYYASWYQQ KPGQAPVLVIYGKNNRPSGIPDRFSGSSSGNTASLTITGA QAEDEADYYCNSINSTRNEVFGGGTKLTVLGQPKAAPS VTLFPPSSEELQANKATLVCLISDFYPGAVTVAWKADSS PVKAGVETTTPSKQSNNKYAASSYLSLTPEQWKSHRSY SCQVTHEGSTVEKTVAPTECS | SEQ ID NO: 61 |
|  | Heavy chain | EVQLLESGGGLVQPGGSLRLSCAASGFTFSSYAMSWVR QAPGKGLEWVSAISGSGGSTYYADSVKGRFTISKDNSK NTLYLQMNSLRAEDTAVYYCAKTSPRVPLDYWGQGTL VTVSSASTKGPSVFPLAPSSKSTSGGTAALGCLVKDYFP EPVTVSWNSGALTSGVHTFPAVLQSSGLYSLSSVVTVPS SSLGTQTYICNVNHKPSNTKVDKKVEPKSCDKTHTCPP CPAPELLGGPSVFLFPPKPKDTLMISRTPEVTCVVVDVS HEDPEVKFNWYVDGVEVHNAKTKPREEQYNSTYRVVS VLTVLHQDWLNGKEYKCKVSNKALPAPIEKTISKAKGQ PREPQVYTLPPSRDELTKNQVSLTCLVKGFYPSDIAVEW ESNGQPENNYKTTPPVLDSDGSFFLYSKLTVDKSRWQQ GNVFSCSVMHEALHNHYTQKSLSLSPGK | SEQ ID NO: 62 |

TABLE 22

Base pair sequences of anti-TnC
clones in P329GLALA human IgG1 format

| Clone | Chain | Base pair sequence | SEQ ID NO |
|---|---|---|---|
| 18D4 | Light chain | See above | SEQ ID NO: 55 |
|  | Heavy chain PGLALA | CAGGTGCAATTGGTGCAGTCTGGGGCTGAGGTGAAG AAGCCTGGGTCCTCGGTGAAGGTCTCCTGCAAGGCC TCCGGAGGCACATTCAGCAGCTACGCTATAAGCTGG GTGCGACAGGCCCCTGGACAAGGGCTCGAGTGGATG GGAGGGATCATCCCTATCTTTGGTACAGCAAACTAC GCACAGAAGTTCCAGGGCAGGGTCACCATTACTGCA GACAAATCCACGAGCACAGCCTACATGGAGCTGAGC AGCCTGAGATCTGAGGACACCGCCGTGTATTACTGT GCGAAAGGTAACTTCTACGGTGGTCTGGACTACTGG GGCCAAGGGACCACCGTGACCGTCTCCTCAGCTAGC ACCAAGGGCCCATCGGTCTTCCCCCTGGCACCCTCCT CCAAGAGCACCTCTGGGGGCACAGCGGCCCTGGGCT GCCTGGTCAAGGACTACTTCCCCGAACCGGTGACGG TGTCGTGGAACTCAGGCGCCCTGACCAGCGGCGTGC ACACCTTCCCGGCTGTCCTACAGTCCTCAGGACTCTA CTCCCTCAGCAGCGTGGTGACCGTGCCCTCCAGCAG CTTGGGCACCCAGACCTACATCTGCAACGTGAATCA CAAGCCCAGCAACACCAAGGTGGACAAGAAAGTTG AGCCCAAATCTTGTGACAAAACTCACACATGCCCAC CGTGCCCAGCACCTGAAGCTGCAGGGGGACCGTCAG TCTTCCTCTTCCCCCCAAAACCCAAGGACACCCTCAT GATCTCCCGGACCCCTGAGGTCACATGCGTGGTGGT GGACGTGAGCCACGAAGACCCTGAGGTCAAGTTCAA CTGGTACGTGGACGGCGTGGAGGTGCATAATGCCAA GACAAAGCCGCGGGAGGAGCAGTACAACAGCACGT | SEQ ID NO: 63 |

TABLE 22-continued

Base pair sequences of anti-TnC
clones in P329GLALA human IgG1 format

| Clone | Chain | Base pair sequence | |
|---|---|---|---|
| | | ACCGTGTGGTCAGCGTCCTCACCGTCCTGCACCAGG<br>ACTGGCTGAATGGCAAGGAGTACAAGTGCAAGGTCT<br>CCAACAAAGCCCTCGGCGCCCCCATCGAGAAAACCA<br>TCTCCAAAGCCAAAGGGCAGCCCCGAGAACCACAGG<br>TGTACACCCTGCCCCCATCCCGGGATGAGCTGACCA<br>AGAACCAGGTCAGCCTGACCTGCCTGGTCAAAGGCT<br>TCTATCCCAGCGACATCGCCGTGGAGTGGGAGAGCA<br>ATGGGCAGCCGGAGAACAACTACAAGACCACGCCTC<br>CCGTGCTGGACTCCGACGGCTCCTTCTTCCTCTACAG<br>CAAGCTCACCGTGGACAAGAGCAGGTGGCAGCAGG<br>GGAACGTCTTCTCATGCTCCGTGATGCATGAGGCTCT<br>GCACAACCACTACACGCAGAAGAGCCTCTCCCTGTC<br>TCCGGGTAAA | |
| 11C7 | Light<br>chain | See above | SEQ ID NO: 57 |
| | Heavy<br>chain<br>PGLAL<br>A | GAGGTGCAATTGTTGGAGTCTGGGGGAGGCTTGGTA<br>CAGCCTGGGGGGTCCCTGAGACTCTCCTGTGCAGCC<br>TCCGGATTCACCTTTAGCAGTTATGCCATGAGCTGGG<br>TCCGCCAGGCTCCAGGGAAGGGGCTGGAGTGGGTCT<br>CAGCTATTAGCGGTAGTGGTGGTAGCACATACTACG<br>CAGACTCCGTGAAGGCCGGTTCACCATCTCCAAAG<br>ACAATTCCAAGAACACGCTGTATCTGCAGATGAACA<br>GCCTGAGAGCCGAGGACACGGCCGTATATTACTGTG<br>CGAAAACTTCTCCGCGTGTTCCGCTGGACTACTGGG<br>GCCAAGGAACCCTGGTCACCGTCTCGAGTGCTAGCA<br>CCAAGGGCCCATCGGTCTTCCCCCTGGCACCCTCCTC<br>AAGAGCACCTCTGGGGGCACAGCGGCCCTGGGCTG<br>CCTGGTCAAGGACTACTTCCCCGAACCGGTGACGGT<br>GTCGTGGAACTCAGGCGCCCTGACCAGCGGCGTGCA<br>CACCTTCCCGGCTGTCCTACAGTCCTCAGGACTCTAC<br>TCCCTCAGCAGCGTGGTGACCGTGCCCTCCAGCAGC<br>TTGGGCACCCAGACCTACATCTGCAACGTGAATCAC<br>AAGCCCAGCAACACCAAGGTGGACAAGAAAGTTGA<br>GCCCAAATCTTGTGACAAAACTCACACATGCCCACC<br>GTGCCCAGCACCTGAAGCTGCAGGGGGACCGTCAGT<br>CTTCCTCTTCCCCCCAAAACCCAAGGACACCCTCATG<br>ATCTCCCGGACCCCTGAGGTCACATGCGTGGTGGTG<br>GACGTGAGCCACGAAGACCCTGAGGTCAAGTTCAAC<br>TGGTACGTGGACGGCGTGGAGGTGCATAATGCCAAG<br>ACAAAGCCGCGGGAGGAGCAGTACAACAGCACGTA<br>CCGTGTGGTCAGCGTCCTCACCGTCCTGCACCAGGA<br>CTGGCTGAATGGCAAGGAGTACAAGTGCAAGGTCTC<br>CAACAAAGCCCTCGGCGCCCCCATCGAGAAAACCAT<br>CTCCAAAGCCAAAGGGCAGCCCCGAGAACCACAGGT<br>GTACACCCTGCCCCCATCCCGGGATGAGCTGACCAA<br>GAACCAGGTCAGCCTGACCTGCCTGGTCAAAGGCTT<br>CTATCCCAGCGACATCGCCGTGGAGTGGGAGAGCAA<br>TGGGCAGCCGGAGAACAACTACAAGACCACGCCTCC<br>CGTGCTGGACTCCGACGGCTCCTTCTTCCTCTACAGC<br>AAGCTCACCGTGGACAAGAGCAGGTGGCAGCAGGG<br>GAACGTCTTCTCATGCTCCGTGATGCATGAGGCTCTG<br>CACAACCACTACACGCAGAAGAGCCTCTCCCTGTCT<br>CCGGGTAAA | SEQ ID NO: 64 |

TABLE 23

Polypeptide sequences of anti-TnC
clones in P329GLALA human IgG1 format

| Clone | Chain | Polypeptide sequence | |
|---|---|---|---|
| 18D4 | Light<br>chain | See above | SEQ ID NO: 59 |
| | Heavy<br>chain | QVQLVQSGAEVKKPGSSVKVSCKASGGTFSSYAISWV<br>RQAPGQGLEWMGGIIPIFGTANYAQKFQGRVTITADKS<br>TSTAYMELSSLRSEDTAVYYCAKGNFYGGLDYWGQG<br>TTVTVSSASTKGPSVFPLAPSSKSTSGGTAALGCLVKD<br>YFPEPVTVSWNSGALTSGVHTFPAVLQSSGLYSLSSVV<br>TVPSSSLGTQTYICNVNHKPSNTKVDKKVEPKSCDKTH<br>TCPPCPAPEAAGGPSVFLFPPKPKDTLMISRTPEVTCVV | SEQ ID NO: 65 |

TABLE 23-continued

Polypeptide sequences of anti-TnC
clones in P329GLALA human IgG1 format

| Clone | Chain | Polypeptide sequence | |
|---|---|---|---|
| | | VDVSHEDPEVKFNWYVDGVEVHNAKTKPREEQYNST<br>YRVVSVLTVLHQDWLNGKEYKCKVSNKALGAPIEKTI<br>SKAKGQPREPQVYTLPPSRDELTKNQVSLTCLVKGFYP<br>SDIAVEWESNGQPENNYKTTPPVLDSDGSFFLYSKLTV<br>DKSRWQQGNVFSCSVMHEALHNHYTQKSLSLSPGK | |
| 11C7 | Light<br>chain | See above | SEQ ID NO: 61 |
| | Heavy<br>chain | EVQLLESGGGLVQPGGSLRLSCAASGFTFSSYAMSWV<br>RQAPGKGLEWVSAISGSGGSTYYADSVKGRFTISKDNS<br>KNTLYLQMNSLRAEDTAVYYCAKTSPRVPLDYWGQG<br>TLVTVSSASTKGPSVFPLAPSSKSTSGGTAALGCLVKD<br>YFPEPVTVSWNSGALTSGVHTFPAVLQSSGLYSLSSVV<br>TVPSSSLGTQTYICNVNHKPSNTKVDKKVEPKSCDKTH<br>TCPPCPAPEAAGGPSVFLFPPKPKDTLMISRTPEVTCVV<br>VDVSHEDPEVKFNWYVDGVEVHNAKTKPREEQYNST<br>YRVVSVLTVLHQDWLNGKEYKCKVSNKALGAPIEKTI<br>SKAKGQPREPQVYTLPPSRDELTKNQVSLTCLVKGFYP<br>SDIAVEWESNGQPENNYKTTPPVLDSDGSFFLYSKLTV<br>DKSRWQQGNVFSCSVMHEALHNHYTQKSLSLSPGK | SEQ ID NO: 66 |

Example 4

Purification of Anti-TnC IgGs

All genes were transiently expressed under control of a chimeric MPSV promoter consisting of the MPSV core promoter combined with the CMV promoter enhancer fragment. The expression vector also contains the oriP region for episomal replication in EBNA (Epstein Barr Virus Nuclear Antigen) containing host cells. The anti-TnC IgGs were produced by co-transfecting HEK293-EBNA cells with the mammalian expression vectors using polyethylenimine. The cells were transfected with the corresponding expression vectors in a 1:1 ratio ("vector HC": "vector HLC").

For a 200 mL production in 500 mL shake flasks, 250 million HEK293 EBNA cells were seeded 24 hours before transfection in Excell media with supplements. For transfection, the cells were centrifuged for 5 minutes at 210×g, and supernatant was replaced by pre-warmed CD-CHO medium. Expression vectors were mixed in 20 mL CD-CHO medium to a final amount of 200m DNA. After addition of 540 µL PEI (1 mg/mL), the solution was vortexed for 15 seconds and incubated for 10 minutes at room temperature. Afterwards, cells were mixed with the DNA/PEI solution, transferred to a 500 mL shake flask and incubated for 3 hours at 37° C. in an incubator with a 5% $CO_2$ atmosphere and shaking at 165 rpm. After the incubation, 160 mL Excell medium with supplements was added and cells were cultured for 24 hours. At this point the valproic acid concentration is 1 mM (the media comprises additionally g/L PepSoy and 6 mM L-Glutamine). 24 hours after transfection the cells are supplement with an amino acid and glucose feed at 12% final volume (24 mL) and 3 g/L glucose (1.2 mL from 500 g/L stock). After culturing for 7 days, the cell supernatant was collected by centrifugation for 45 minutes at 2000-3000×g. The solution was sterile filtered (0.22 µm filter), supplemented with sodium azide to a final concentration of 0.01% (w/v), and kept at 4° C.

Purification of anti-TnC IgGs from cell culture supernatants was carried out by affinity chromatography using MabSelectSure. The protein was concentrated and filtered prior to loading on a HiLoad Superdex 200 column (GE Healthcare) equilibrated with 20 mM Histidine, 140 mM NaCl, 0.01% Tween-20 solution of pH 6.0.

For affinity chromatography, the supernatant was loaded on a ProtA MabSelect Sure column (CV=6 mL, GE Healthcare) equilibrated with 36 mL 20 mM Sodium Citrate, 20 mM Sodium Phosphate, pH 7.5. Unbound protein was removed by washing with 6-10 column volumes of a buffer containing 20 mM Sodium Citrate, 20 mM Sodium Phosphate, pH 7.5. The bound protein was eluted using a linear pH-gradient of 15 CVs of sodium chloride (from 20 to 100%) of 20 mM Sodium Citrate, 100 mM Sodium Chloride, 100 mM Glycine, 0.01% (v/v) Tween-20, pH 3.0. The column was then washed with 4 column volumes of a solution containing 20 mM Sodium Citrate, 100 mM Sodium Chloride, 100 mM Glycine, 0.01% (v/v) Tween-20, pH 3.0 followed by a re-equilibration step.

The pH of the collected fractions was adjusted by adding 1/10 (v/v) of 0.5 M $Na_2HPO_4$, pH 8.0. The protein was concentrated and filtered prior to loading on a HiLoad Superdex 200 column (GE Healthcare) equilibrated with 20 mM Histidine, 140 mM NaCl, pH 6.0, 0.01% Tween20.

The protein concentration of purified IgGs was determined by measuring the OD at 280 nm, using the molar extinction coefficient calculated on the basis of the amino acid sequence. Purity and molecular weight of the IgGs were analyzed by CE-SDS in the presence and absence of a reducing agent (Invitrogen, USA) using a LabChipGXII (Caliper). The aggregate content of the purified protein was analyzed using a TSKgel G3000 SW XL analytical size-exclusion column (Tosoh) equilibrated in a 25 mM K2HPO4, 125 mM NaCl, 200 mM L-Arginine Monohydrocloride, 0.02% (w/v) NaN3, pH 6.7 running buffer at 25° C. (Table 25).

TABLE 25

Biochemical analysis of anti-TnC IgG1

| Clone | Yield<br>[mg/l] | Monomer<br>[%] |
|---|---|---|
| a-TnC(18D4)<br>huIgG1 | 6.8 | 98.3 |

TABLE 25-continued

Biochemical analysis of anti-TnC IgG1

| Clone | Yield [mg/l] | Monomer [%] |
|---|---|---|
| a-TnC(18D4) P329GLALA huIgG1 | 26.7 | 100 |

Example 5

Surface Plasmon Resonance (TnC Binding)

Binding of the anti-TnC IgGs 18D4, 11C7 and the Fab fragment of anti-TnC 18D4 to human, murine and cynomolgus TnC (antigens according to Table 4) was assessed by surface plasmon resonance (SPR). All SPR experiments were performed on a Biacore T200 at 25° C. with HBS-EP as running buffer (0.01 M HEPES pH 7.4, 0.15 M NaCl, 3 mM EDTA, 0.005% Surfactant P20, Biacore, Freiburg/Germany). A 20 µg/ml stock solution of biotinylated human, murine or cynomolgus TnC was injected on a SA chip, with the aim to immobilize up to 100 RU using the immobilization wizard function. Final immobilization levels were between 79-400 RU.

The anti-TnC IgGs 18D4 (PGLALA and wtFc), 11C7 (rb IgG) and 18D4 Fab fragment were then immediately passed over the chip surface at a concentration ranging from 0.02-12.5 nM (IgGs) and 0.02-50 nM (Fab fragment) with a flow rate of 30 µl/min for 180 s followed by a dissociation step of 180 s. An additional dissociation step of 1800 s was performed for the highest concentration of IgG. After each step the surface was regenerated following two sequential injections of 10 mM glycine pH2.1 for 60 s. Bulk refractive index differences were corrected for by subtracting the response obtained in a reference flow cell without TNC. Affinity and avidity were calculated using the Langmuir 1:1 kinetic model. However, as the $K_D$ for the 1:1 fitting of bivalent interactions is an apparent value only, it should only be used for comparisons.

TABLE 26

KD values and species cross-reactivity

| Construct | hu TNC KD (nM) | cyno TNC KD (nM) | mu TNC KD (nM) |
|---|---|---|---|
| 18D4 IgG wt Fc | 0.093 | 0.036 | 0.061 |
| 18D4 IgG PG/LALA | 0.032 | 0.011 | 0.030 |
| 11C7 rb IgG | 0.029 | nd | nd |
| 18D4 Fab fragment | 1.44 | 6.69 | 6.5 |

The anti-TnC binder 18D4 cross-reacts with mouse and cynomolgus TnC with similar avidity in the pM range. Monovalent binding of the 18D4 Fab fragment to TnC results in a $K_D$ in the low nM range. Anti-TNC binder 11C7 also binds human TnC in the pM range. Species cross-reactivity could not be assessed for binder 11C7 due to absence of the C domain in murine and cynomolgus TNC constructs used in this Biacore experiment (Table 26).

Thermal Stability

The thermal stability was monitored by Static Light Scattering (SLS) and by measuring the intrinsic protein fluorescence in response to applied temperature stress. 30 µg of filtered protein sample with a protein concentration of 1 mg/ml was applied in duplicate to an Optim 2 instrument (Avacta Analytical Ltd). The temperature was ramped from 25 to 85° C. at 0.1° C./min, with the radius and total scattering intensity being collected. For determination of intrinsic protein fluorescence the sample was excited at 266 nm and emission was collected between 275 nm and 460 nm.

TABLE 27

Thermal stability

| Construct | Tagg (° C.) |
|---|---|
| 18D4 IgG PGLALA | 62 |
| 18D4 IgG wtFc | 62 |

Both IgGs have an aggregation temperature of 62° C. (Table 27).

Example 6

Results of TnC Staining in LS174T xenograft Derived Tumor Tissue and Human Tissue Array Anti-TnC clones 18D4 and 11C7 as rabbit IgG antibodies were tested in LS174T xenograft derived tumor tissue and human tissue array for detection of TnC with an immunohistochemistry technique.

The LS174T colorectal carcinoma frozen tumor samples were sectioned in a Cryostat at 12 µm thickness, mounted on superfrost slides (Thermo Scientific, Germany). Frozen samples of human tissue array including paired normal and tumor samples were purchased from Biochain (San Francisco, USA). Tissue sections were allowed to thaw for 30 minutes. Slides were washed in PBS, fixed in cold acetone for 10 minutes and an incubation step with 0.03% hydrogen peroxidase in water was performed to block the endogeneous peroxidase. The sections were then incubated for 1 h with 5% goat serum in PBS followed by overnight incubation with 0.5 µg/ml anti-TnC clone 18D4 or 11C7 or an isotype control antibody (Serotec, Germany) at 4° C. Afterwards, the sections were washed with PBS three times for 5 minutes each and developed using the peroxidase Rabbit Vectastain ABC kit following the manufacturers' instructions (PK-6101, Vector laboratories, Calif., USA). Slides were then dehydrated in increasing concentration of ethanol and incubated 2 minutes in Xylene. One drop of Permount mounting medium (Fischer Chemical, Germany) was added to the sections and coverslip. Images were obtained with Olympus scanner VS120 (Olympus, Germany) and analyzed.

Figure 2:
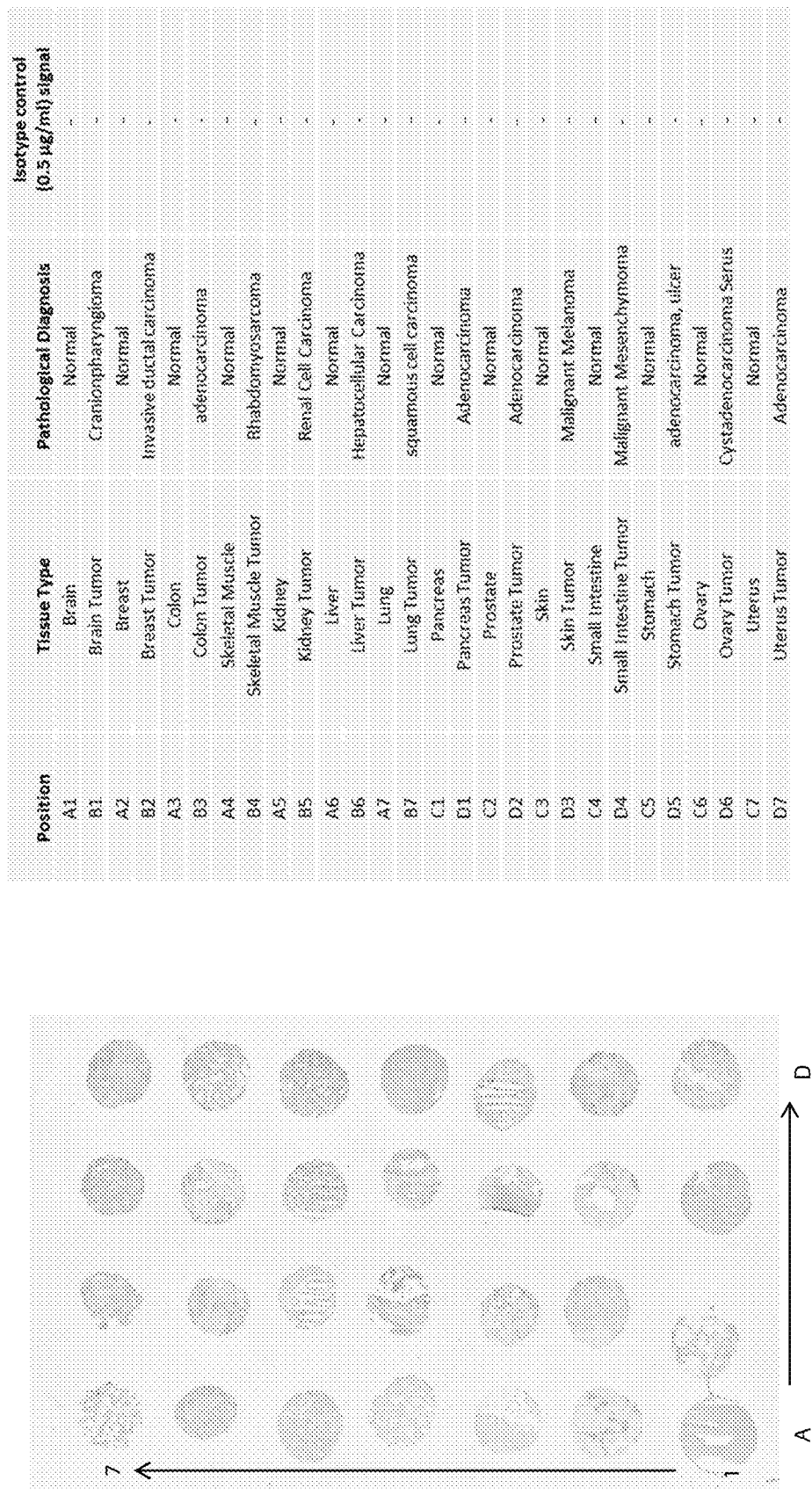
FIG. 2 shows the results of the immunohistological staining in human tumor array with a rabbit isotype control. Negative isotype control signal in all tissues tested validates the specificity of the technique.
Figure 3:
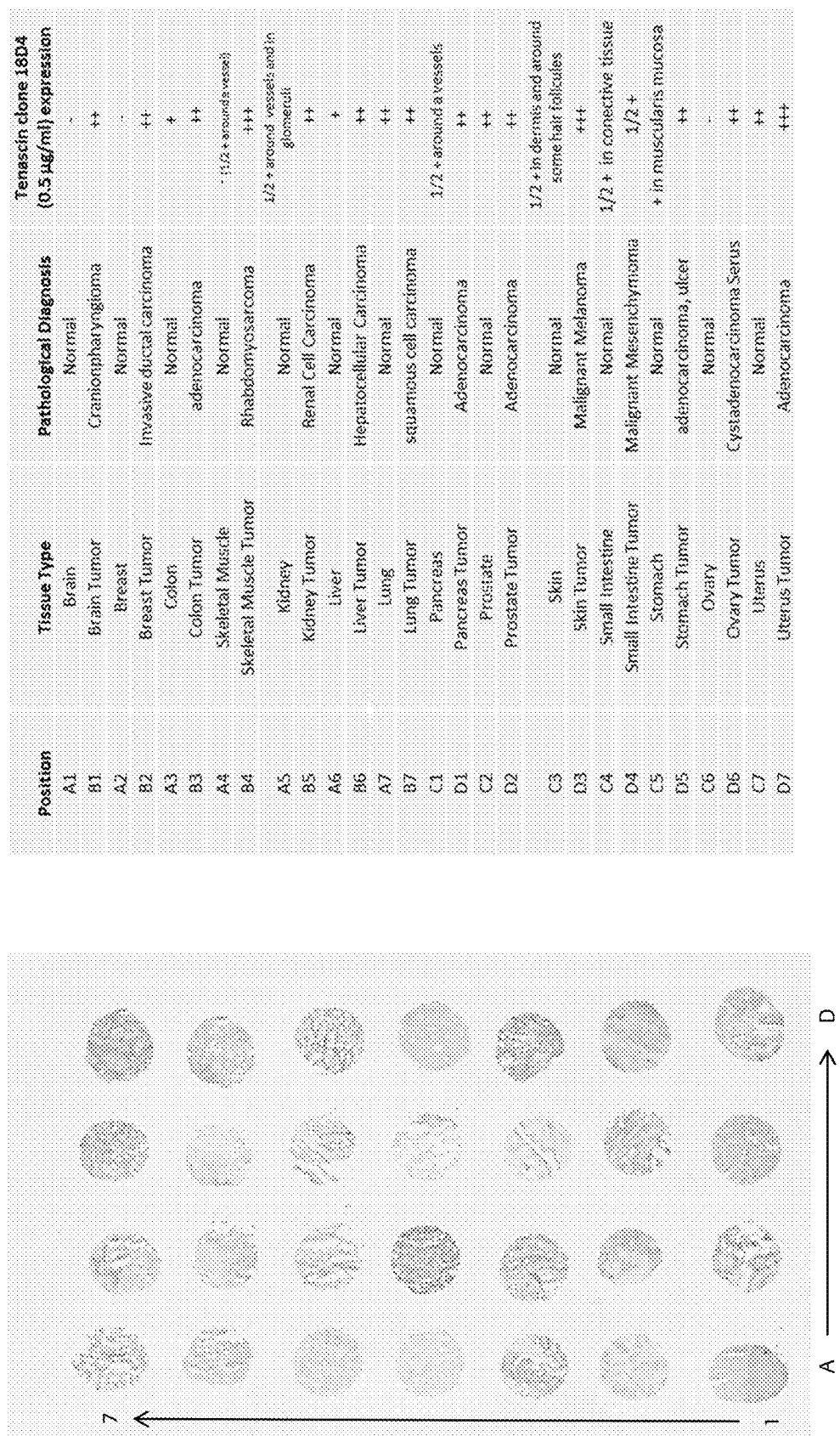
FIG. 3 shows the results of the immunohistological staining in human tumor array with anti-TnC clone 18D4. The pattern of staining corresponds to specific TnC stroma fibers. The TnC staining is expressed at higher levels in most tumor tissues compared to control normal pair tissue.
Figure 4:
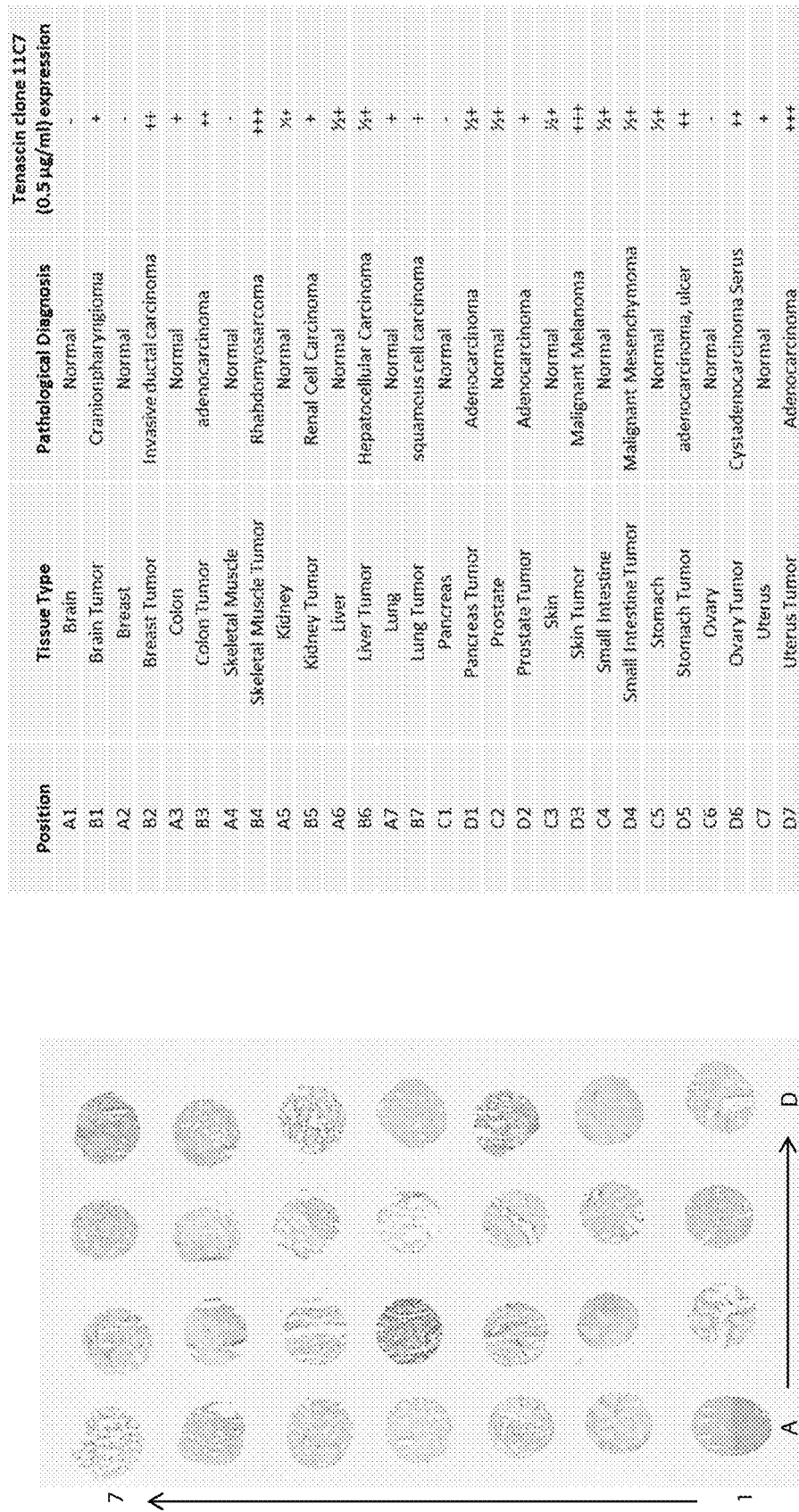
FIG. 4 shows the results of the immunohistological staining in human tumor array with anti-TnC clone 11C7. The pattern of staining corresponds to specific TnC stroma fibers. The TnC staining is expressed at higher levels in most tumor tissues compared to control normal pair tissue.

The pattern of histological staining in LS174T xenografts tumors corresponds to specific TnC stroma fibers (FIG. 1). The TnC staining, for both clones 18D4 and 11C7, is overall expressed with moderate intensity. Negative isotype control signal validates the specificity of the technique. Specificity of the staining is validated by negative isotype control singals in the corresponding histological staining in with a rabbit isotype control (FIG. 2). Histological staining in human tumor array with anti-TnC clone 18D4 corresponds to specific TnC stroma fibers. The TnC staining is expressed at higher levels in most tumor tissues compared to control normal pair tissue (FIG. 3). Histological staining in human tumor array with anti-TnC clone 11C7 corresponds to specific TnC stroma fibers. The TnC staining is expressed at higher levels in most tumor tissues compared to control normal pair tissue (FIG. 4).

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An antibody that specifically binds to Tenascin-C (TnC), wherein said antibody comprises:
   (i) a heavy chain variable region comprising a heavy chain CDR1 of SEQ ID NO: 49, a heavy chain CDR2 of SEQ ID NO: 50 and a heavy chain CDR3 of SEQ ID NO:51; and a light chain variable region comprising a light chain CDR1 of SEQ ID NO: 37, a light chain CDR2 of SEQ ID NO: 38 and a light chain CDR3 of SEQ ID NO: 39; or
   (ii) a heavy chain variable region comprising a heavy chain CDR1 of SEQ ID NO: 52, a heavy chain CDR2 of SEQ ID NO: 53 and a heavy chain CDR3 of SEQ ID NO: 54; and a light chain variable region comprising a light chain CDR1 of SEQ ID NO: 40, a light chain CDR2 of SEQ ID NO:41 and a light chain CDR3 of SEQ ID NO: 42; wherein said antibody has cross-species reactivity.

2. The antibody of claim 1, wherein said antibody comprises a heavy chain variable region comprising
   (a) the heavy chain CDR1 of SEQ ID NO: 49;
   (b) the heavy chain CDR2 of SEQ ID NO: 50;
   (c) the heavy chain CDR3 of SEQ ID NO: 51,
   and a light chain variable region comprising
   (a) the light chain CDR1 of SEQ ID NO: 37;
   (b) the light chain CDR2 of SEQ ID NO: 38, and
   (c) the light chain CDR3 of SEQ ID NO: 39.

3. The antibody of claim 1, wherein said antibody comprises a heavy chain variable region comprising
   (a) the heavy chain CDR1 of SEQ ID NO: 52;
   (b) the heavy chain CDR2 of SEQ ID NO: 53;
   (c) the heavy chain CDR3 of SEQ ID NO: 54,
   and a light chain variable region comprising
   (a) the light chain CDR1 of SEQ ID NO: 40;
   (b) the light chain CDR2 of SEQ ID NO: 41, and
   (c) the light chain CDR3 of SEQ ID NO: 42.

4. The antibody of claim 1, wherein said antibody comprises a heavy chain variable region comprising an amino acid sequence of SEQ ID NO: 28 and a light chain variable region comprising an amino acid sequence of SEQ ID NO: 27.

5. The antibody of claim 1, wherein said antibody comprises a heavy chain variable region comprising an amino acid sequence of SEQ ID NO: 30 and a light chain variable region comprising an amino acid sequence of SEQ ID NO: 29.

6. The antibody of claim 1, wherein said antibody comprises an Fc region or a region equivalent to the Fc region of an immunoglobulin.

7. The antibody of claim 1, wherein said Fc region is an IgG1 Fc region.

8. The antibody of claim 1, wherein said antibody is a human antibody.

9. The antibody of claim 1, wherein said antibody has an improved affinity.

10. The antibody of claim 1, wherein said antibody binds to at least one of human, mouse and cynomolgus TnC with a $K_D$ value lower than about 2 nM.

11. The antibody of claim 1, wherein the antibody binds to human, mouse and cynomolgus TnC.

12. The antibody of claim 1, wherein said antibody binds to the target antigen from all indicated species with similar affinity.

13. The antibody of claim 12, wherein said antibody binds to the target antigen from all indicated species with similar affinity, in particular within a $K_D$ range of a factor of 10.

14. The antibody of claim 1, wherein the antibody is a multispecific antibody.

15. The antibody of claim 1, wherein the antibody is a bispecific antibody.

16. A pharmaceutical formulation comprising an antibody that specifically binds to Tenascin-C (TnC), wherein said antibody comprises:
   (i) a heavy chain variable region comprising a heavy chain CDR1 of SEQ ID NO: 49, a heavy chain CDR2 of SEQ ID NO: 50 and a heavy chain CDR3 of SEQ ID NO:51; and a light chain variable region comprising a light chain CDR1 of SEQ ID NO: 37, a light chain CDR2 of SEQ ID NO: 38 and a light chain CDR3 of SEQ ID NO: 39; or
   (ii) a heavy chain variable region comprising a heavy chain CDR1 of SEQ ID NO: 52, a heavy chain CDR2 of SEQ ID NO: 53 and a heavy chain CDR3 of SEQ ID NO: 54; and a light chain variable region comprising a light chain CDR1 of SEQ ID NO: 40, a light chain CDR2 of SEQ ID NO:41 and a light chain CDR3 of SEQ ID NO: 42; wherein said antibody has cross-species reactivity.

17. The antibody of claim 1 for use as a medicament.

18. A method of treating an individual having a disease characterized by expression of TnC, the method comprising administering to a patient in need thereof an antibody that specifically binds to Tenascin-C (TnC), wherein said antibody comprises:
   (i) a heavy chain variable region comprising a heavy chain CDR1 of SEQ ID NO: 49, a heavy chain CDR2 of SEQ ID NO: 50 and a heavy chain CDR3 of SEQ ID NO:51; and a light chain variable region comprising a light chain CDR1 of SEQ ID NO: 37, a light chain CDR2 of SEQ ID NO: 38 and a light chain CDR3 of SEQ ID NO: 39; or
   (ii) a heavy chain variable region comprising a heavy chain CDR1 of SEQ ID NO: 52, a heavy chain CDR2 of SEQ ID NO: 53 and a heavy chain CDR3 of SEQ ID NO: 54; and a light chain variable region comprising a light chain CDR1 of SEQ ID NO: 40, a light chain CDR2 of SEQ ID NO:41 and a light chain CDR3 of SEQ ID NO: 42; wherein said antibody has cross-species reactivity.

19. The method of claim 18, wherein said disease is cancer.

20. The method of manufacturing an antibody that specifically binds to Tenascin-C (TnC) for treating cancer, wherein said antibody comprises:
   (i) a heavy chain variable region comprising a heavy chain CDR1 of SEQ ID NO: 49, a heavy chain CDR2 of SEQ ID NO: 50 and a heavy chain CDR3 of SEQ ID NO:51; and a light chain variable region comprising a light chain CDR1 of SEQ ID NO: 37, a light chain CDR2 of SEQ ID NO: 38 and a light chain CDR3 of SEQ ID NO: 39; or (ii) a heavy chain variable region comprising a heavy chain CDR1 of SEQ ID NO: 52, a heavy chain CDR2 of SEQ ID NO: 53 and a heavy chain CDR3 of SEQ ID NO: 54; and a light chain variable region comprising a light chain CDR1 of SEQ ID NO: 40, a light chain CDR2 of SEQ ID NO:41 and a light chain CDR3 of SEQ ID NO: 42; wherein said antibody has cross-species reactivity.

21. The method of claim 20 wherein the antibody is for inducing lysis of a tumor cell or a stromal cell of a tumor.

22. A method of treating an individual having a disease characterized by TnC expression, comprising administering to the individual an effective amount of the antibody of claim 1, or the pharmaceutical formulation of claim 16.

23. The method of claim 22, wherein said disease is cancer.

24. The method of claim 18 wherein the antibody is for inducing lysis of a tumor cell or a stromal cell of a tumor.

* * * * *